(12) United States Patent
Chang et al.

(10) Patent No.: US 11,965,208 B2
(45) Date of Patent: Apr. 23, 2024

(54) METHODS OF ASSOCIATING PHENOTYPICAL DATA AND SINGLE CELL SEQUENCING DATA

(71) Applicant: Becton, Dickinson and Company, Franklin Lakes, NJ (US)

(72) Inventors: Christina Chang, San Jose, CA (US); Sixing Li, San Jose, CA (US)

(73) Assignee: Becton, Dickinson And Company, Franklin Lakes, NJ (US)

(*) Notice: Subject to any disclaimer, the term of this patent is extended or adjusted under 35 U.S.C. 154(b) by 105 days.

(21) Appl. No.: 16/849,191

(22) Filed: Apr. 15, 2020

(65) Prior Publication Data

US 2020/0332351 A1    Oct. 22, 2020

Related U.S. Application Data

(60) Provisional application No. 62/836,504, filed on Apr. 19, 2019.

(51) Int. Cl.
  *C12Q 1/6837* (2018.01)
  *C12Q 1/6827* (2018.01)
  *C12Q 1/6858* (2018.01)

(52) U.S. Cl.
  CPC ......... *C12Q 1/6837* (2013.01); *C12Q 1/6827* (2013.01); *C12Q 1/6858* (2013.01); *C12Q 2600/156* (2013.01); *C12Q 2600/16* (2013.01)

(58) Field of Classification Search
  CPC ............ C12Q 1/6804; C12Q 2537/143; C12Q 2563/159; C12Q 2563/179; C12Q 1/6837; C12Q 1/6827; C12Q 2600/16
  See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchick et al. |
| 5,962,272 A | 10/1999 | Chenchick et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |

(Continued)

FOREIGN PATENT DOCUMENTS

| | | |
|---|---|---|
| DE | 102008025656 | 12/2009 |
| EP | 0 799 897 | 10/1997 |

(Continued)

OTHER PUBLICATIONS

Achim et al., May 2015, High-throughput spatial mapping of single-cell RNA-seq data to tissue of origin. Nature Biotechnology, 33(5):503-511.

Agasti et al., Nov. 14, 2012 Photocleavable DNA barcode-antibody conjugates allow sensitive and multiplexed protein analysis in single cell, J Am Chem Soc., 134(45);18499-19502.

Algae, Wikipedia.org, accessed Mar. 4, 2016, 20 pp.

Alkan et al., Oct. 2009, Personalized copy number and segmental duplication maps using next-generation sequencing. Nat Genet., 41(10):1061-1067.

(Continued)

*Primary Examiner* — Sahana S Kaup
(74) *Attorney, Agent, or Firm* — KNOBBE, MARTENS, OLSON & BEAR, LLP

(57) ABSTRACT

Disclosed herein include systems, methods, compositions, and kits for associating single cell sequencing data with phenotypic data and/or agent exposure. In some embodiments, cell indexing oligonucleotides comprising cell indexing sequences are associated with cells. In some embodiments, synthetic particles are associated with stochastic labels comprising cell indexing sequences. Sequential hybridizing and imaging of probes annealing to a cell indexing sequence can generate a spatial index. The spatial index can be employed to identify of the partition from which a sequenced nucleic acid target molecule originated.

30 Claims, 13 Drawing Sheets

(56) References Cited

U.S. PATENT DOCUMENTS

| | | |
|---|---|---|
| 6,197,554 B1 | 3/2001 | Lin et al. |
| 6,235,475 B1 | 5/2001 | Brenner et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,531,283 B1 | 3/2003 | Kingsmore et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,486,628 B2 | 7/2013 | Loeffert |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 | 2/2017 | Fan et al. |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,708,659 B2 | 7/2017 | Fodor et al. |
| 9,787,810 B1 | 8/2017 | Fodor et al. |
| 9,816,137 B2 | 11/2017 | Fodor et al. |
| 9,845,502 B2 | 12/2017 | Fodor et al. |
| 9,951,386 B2 | 4/2018 | Hindson et al. |
| 10,030,267 B2 | 7/2018 | Hindson et al. |
| 10,041,116 B2 | 8/2018 | Hindson et al. |
| 10,059,991 B2 | 8/2018 | Fodor et al. |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0168665 A1 | 11/2002 | Okawa |
| 2002/0192687 A1 | 12/2002 | Mirkin et al. |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0142344 A1 | 7/2004 | Bazan et al. |
| 2004/0146901 A1 | 7/2004 | Morris et al. |
| 2004/0157243 A1 | 8/2004 | Huang et al. |
| 2004/0253593 A1 | 12/2004 | Cai |
| 2004/0259118 A1 | 12/2004 | Macevicz |
| 2005/0019776 A1 | 1/2005 | Callow et al. |
| 2005/0053952 A1 | 3/2005 | Hong et al. |
| 2005/0105077 A1 | 5/2005 | Padmanabhan |
| 2005/0170373 A1 | 8/2005 | Monforte |
| 2005/0250147 A1 | 11/2005 | Macevicz |
| 2005/0287548 A1 | 12/2005 | Bao |
| 2006/0002824 A1 | 1/2006 | Chang et al. |
| 2006/0024690 A1 | 2/2006 | Kao |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2006/0280352 A1 | 12/2006 | Muschler |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0105090 A1 | 5/2007 | Cassidy et al. |
| 2007/0117121 A1 | 5/2007 | Hutchison |
| 2007/0117134 A1 | 5/2007 | Kou |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2008/0064042 A1 | 3/2008 | Bazan et al. |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0293164 A1 | 11/2008 | Gaylord et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |

(56) References Cited

U.S. PATENT DOCUMENTS

| | | |
|---|---|---|
| 2010/0120630 A1 | 5/2010 | Huang et al. |
| 2010/0136544 A1 | 6/2010 | Agresti et al. |
| 2010/0136702 A1 | 6/2010 | Bazan et al. |
| 2010/0159533 A1 | 6/2010 | Lipson et al. |
| 2010/0255471 A1 | 10/2010 | Clarke |
| 2010/0267028 A1 | 10/2010 | Pasche |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0256549 A1 | 10/2011 | Gaylord et al. |
| 2011/0294689 A1 | 12/2011 | Namsaraev |
| 2012/0010091 A1 | 1/2012 | Linnarson |
| 2012/0014977 A1 | 1/2012 | Furihata et al. |
| 2012/0028828 A1 | 2/2012 | Gaylord et al. |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0231972 A1 | 9/2012 | Golyshin et al. |
| 2012/0252012 A1 | 10/2012 | Armougom et al. |
| 2012/0252986 A1 | 10/2012 | Liu et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0190193 A1 | 7/2013 | Bazan et al. |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0057799 A1 | 2/2014 | Johnson |
| 2014/0147860 A1 | 5/2014 | Kaduchak |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0066385 A1 | 3/2015 | Schnall-Levin et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0267251 A1* | 9/2015 | Cai ................ G02B 21/06 506/9 |
| 2015/0298091 A1 | 10/2015 | Weitz |
| 2015/0299784 A1* | 10/2015 | Fan ................ C12Q 1/6881 506/4 |
| 2015/0307874 A1 | 10/2015 | Jaitin |
| 2015/0376609 A1 | 12/2015 | Hindson et al. |
| 2016/0025735 A1 | 1/2016 | Gaylord et al. |
| 2016/0026758 A1 | 1/2016 | Jabara et al. |
| 2016/0122753 A1 | 5/2016 | Mikkelsen |
| 2016/0208322 A1 | 7/2016 | Anderson et al. |
| 2016/0244828 A1 | 8/2016 | Mason |
| 2016/0257993 A1 | 9/2016 | Fu et al. |
| 2016/0289669 A1 | 10/2016 | Fan et al. |
| 2016/0289740 A1* | 10/2016 | Fu .................. C12Q 1/6806 |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 12/2016 | Fodor et al. |
| 2016/0376648 A1 | 12/2016 | Fodor et al. |
| 2017/0073730 A1 | 3/2017 | Betts et al. |
| 2017/0154421 A1 | 6/2017 | Fu et al. |
| 2017/0192013 A1 | 7/2017 | Agresti |
| 2017/0275669 A1 | 9/2017 | Weissleder et al. |
| 2017/0314067 A1 | 11/2017 | Shum et al. |
| 2018/0088112 A1 | 3/2018 | Fan et al. |
| 2018/0251825 A1 | 9/2018 | Stoeckius et al. |
| 2018/0267036 A1 | 9/2018 | Fan et al. |
| 2018/0346969 A1 | 12/2018 | Chang et al. |
| 2018/0346970 A1 | 12/2018 | Chang et al. |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 036 989 | 3/2009 |
| EP | 2 623 613 | 8/2013 |
| EP | 2 805 769 | 11/2014 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/059355 | 8/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 06/137932 | 12/2006 |
| WO | WO 07/087310 | 8/2007 |
| WO | WO 07/087312 | 8/2007 |
| WO | WO 07/147079 | 12/2007 |
| WO | WO 08/057163 | 5/2008 |
| WO | WO 08/096318 | 8/2008 |
| WO | WO 08/150432 | 12/2008 |
| WO | WO 09/148560 | 12/2009 |
| WO | WO 09/152928 | 12/2009 |
| WO | WO 10/030818 | 3/2010 |
| WO | WO 10/059820 | 5/2010 |

(56) References Cited

FOREIGN PATENT DOCUMENTS

| | | |
|---|---|---|
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/041802 | 4/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/099896 | 7/2012 |
| WO | WO 12/108864 | 8/2012 |
| WO | WO-2012106385 A2 * 8/2012 ........... C12Q 1/6806 | |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/156744 | 11/2012 |
| WO | WO 12/162267 | 11/2012 |
| WO | WO 13/019075 | 2/2013 |
| WO | WO 13/070990 | 5/2013 |
| WO | WO 13/117595 | 8/2013 |
| WO | WO 13/130674 | 9/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/065756 | 5/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/200767 | 12/2014 |
| WO | WO 14/201273 | 12/2014 |
| WO | WO 14/204939 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/200869 | 12/2015 |
| WO | WO 16/044227 | 3/2016 |
| WO | WO 16/118915 | 7/2016 |
| WO | WO 16/138500 | 9/2016 |
| WO | WO 16/149418 | 9/2016 |
| WO | WO 16/160844 | 10/2016 |
| WO | WO 17/079593 | 5/2017 |
| WO | WO-2017075265 A1 * 5/2017 ........... C12Q 1/6811 | |
| WO | WO 18/058073 | 3/2018 |
| WO | WO 18/175458 | 9/2018 |

OTHER PUBLICATIONS

Anderson, Feb. 11, 2014, Study describes RNA sequencing applications for molecular indexing methods, genomeweb.com, 5 pp.
Ansorge, 2009, Next-generation DNA sequencing techniques. New Biotechnology, 25(4):195-203.
Applied Biosystems, Apr. 2008, SOLID™ System Barcoding, Application Note, 4 pp.
Archaea, Wikipedia.org, accessed May 11, 2016, 26 pp.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Baek, 2009, Development of hydrogel TentaGel shell-core beads for ultra-high throughput solution phase screening of encoded OBOC combinatorial small molecule libraries, J Comb Chem, 11(1):91-102 and supporting information.
BD Life Sciences, 2018, BD AbSeq antibody-oligo conjugates,, www.bg.com/genomics, 2 pp.
BD Life Sciences, 2018, BD AbSeq on the BD Rhapsody system: exploraiton of single-cell gene regulation by simulatenous digital mRNA and protein quantification, www.bg.com/genomics, 7 pp.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bogdanova et al., Jan. 2008, Normalization of full-length enriched cDNA, Molecular Biosystems, 4(3):205-212.
Bonaldo et al., Sep. 1996, Normalization and subtraction: two approaches to facilitate gene discovery. Genome Res., 6(9):791-806.
Bontoux et al, "Integrating whole transcriptome assays on a lab-on-a-chip for single cell gene profiling", Lab on a Chip, (2008) vol. 8, No. 3, pp. 443-450.
Brady et al., "Construction of cDNA libraries form single cells", Methods in Enzymology, Academic Press, US, (1993) vol. 225, doi:10.1016/0076-6879(93)25039-5, ISSN 0076-6879, pp. 611-623.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing, 19(3):1-12.
Buschmann et al., Aug. 7, 2014, Enhancing the detection of barcoded reads in high throughput DNA sequencing DNA by controlling the false discovery rate, BMC Bioinformatics, 15(1):264.
Butkus, Feb. 6, 2014, Cellular research set to launch first gene expression platform using 'molecular indexing' technology, genomeweb.com, 5 pp.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number including telomeres and mitochondria, assayed using next-generation sequencing. BMC Genomics, 11:244. doi: 10.1186/1471-2164-11-244.

(56) References Cited

OTHER PUBLICATIONS

Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Clontech Laboratories, Inc., May 15, 2007, Super Smart™ PCR cDNA Synthesis Kit User Manual, 39 pp.
Cloonan et al., "Stem cell transcriptome profiling via massive-scale mRNA sequencing", Nature Methods, (Jul. 2008) vol. 5, No. 7, pp. 613-619.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cotten et al., Jul. 21, 2011, Selection of proteins with desired properties from natural proteome libraries using mRNA display, Nature Protocols, 6(8):1163-1182.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Custom Antibody Services, Precision Antibody, accessed Apr. 16, 2014, 2 pp.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
Day et al., 1991, Immobilization of polynucleotides on magnetic particles, Biochem. J., 278:735-740.
De Saizieu et al., 1998, Bacterial transcript imaging by hybridization of total RNA to oligonucleotide arrays. Nature Biotechnology, 16:45-48.
Di Carlo et al., Dec. 1, 2008, Dynamic single-cell analysis for quantitative biology, Analytical Chemistry, 78(23):7918-7925.
Dirks et al., Oct. 26, 2004, Triggered amplification by hybridization chain reaction., Proc Natl Acad Sci U S A, 101(43), 15275-15278.
Eberwine et al., "Analysis of gene expression in single live neurons", Proc. Natl. Acad. Sci. USA, (Apr. 1992) vol. 89, No. 7, pp. 3010-3014.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Feb. 6, 2015, Combinatorial labeling of single cells for gene expression cytometry. Science, 347(6222):1258367-8.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fish, Wikipedia.org, accessed Nov. 2, 2014, 11 pp.
Flanigon et al., Jan. 1, 2013, Multiplex protein detection with DNA readout via mass spectrometry, New Biotechnology, 30(2):153-158.
Fox-Walsh et al., Oct. 2011, A multiplex RNA-seq strategy to profile poly(A+) RNA: application to analysis of transcription response and 3' end formation., Genomics, 98(4),266-271.
Fu et al., Feb. 4, 2014, Molecular indexing enables quantitative targeted RNA sequencing and reveals poor efficiencies in standard library preparations, PNAS, 111(5):1891-1896.
Fu et al., Marcy 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Fungus, Wikipedia.org, accessed Jun. 3, 2013, 28 pp.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Gong et al., Jan. 20, 2016, Simple method to prepare oligonucleotide-conjugated antibodies and its application in multiplex protein detection in single cells, Bioconjugate Chemistry, 27(1):217-225.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Han et al. Dec. 15, 2010, An approach to multiplexing an immunosorbent assay with antibody-oligonucleotide conjugates, Bioconjugate Chem., 21(12):2190-2196.
Harbers, "The current status of cDNA cloning", Genomics, (2008) vol. 91, No. 3, pp. 232-242.
Harrington et al., 2009, Cross-sectional characterization of HIV-1 env compartmentalization in cerebrospinal fluid over the full disease course, AIDS, 23(8) 907-915.
Hartmann, "Gene expression profiling of single cells on large-scale oligonucleotide arrays", Nucleic Acids Research, (Oct. 2006) vol. 34, No. 21, p. e143.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Holcomb et al., Jul. 2016, Abstract 1853: Single-cell multiplexed profiling of protein-level changes induced by EGFR inhibitor gefitinib, Cancer Research, p. 1853.

(56) References Cited

OTHER PUBLICATIONS

Hollas et al., 2003, A stochastic approach to count RNA molecules using DNA sequencing methods. Lecture Notes in Computer Science, 2812:55-62.
How many species of bacteria are there? Wisegeek.org, accessed Jan. 21, 2014, 2 pp.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., "Highly multiplexed and strand specific single-cell RNA 5' end sequencing", Nature Protocols, (2012) vol. 7, No. 5, pp. 813-828.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Jiang et al., 2011, Synthetic spike-in standards for RNA-seq experiments, Genome Research, 21(9):1543-1551.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Karrer et al., "In situ isolation of mRNA from individual plant cells: creation of cell-specific cDNA libraries.", Proc. Natl. Acad. Sci. USA, (Apr. 1995) vol. 92, No. 9, pp. 3814-3818.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kiresebom et al., 2011, Stimuli-responsive polymers in the 21$^{st}$ century: elaborated architecture to achieve high sensitivity, fast response, and robust behavior, Journal of Polymer Science: Part B: Polymer Physics, 49:173-178.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.

Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kozlov et al., Jan. 2008, A high-complexity, multiplexed solution-phase assay for profiling protease activity on microarrays, Combinatorial Chemistry and High Throughput Screening, 11(1):24-35.
Kurimoto et al, "Global single-cell cDNA amplification to provide a template for representative high-density oligonucleotide microarray analysis", Nature Protocols, (2007) vol. 2, No. 3, pp. 739-752.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Lass-Napiorkowska et al., Apr. 3, 2012, Detection methodology based on target molecule-induced sequence-specific binding to a single-stranded oligonucleotides, Analytical Chemistry, 84(7):3382-3389.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
List of sequenced bacterial genomes, Wikipedia.org, accessed Jan. 24, 2014, 57 pp.
Liu et al., Single-cell transcriptome sequencing: recent advances and remaining challenges, F1000Research 2016, 5(F1000 Faculty Rev): 182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.
Makrigiorgos et al., Sep. 2002, A PCR-Based amplification method retaining quantities difference between two complex genomes. Nature Biotech, 20(9):936-939.
Mammal, Wikipedia.org, accessed Sep. 22, 2011, 16 pp.
Marcus et al., 2006, Microfluidic single-cell mRNA isolation and analysis, Ana. Chem. 78:3084-3089.
Mardis, "Next-generation DNA sequencing methods", Annu. Rev. Genomics Hum. Genet., (2008) vol. 9, pp. 387-402.
Marguerat et al, "Next-generation sequencing: applications beyond genomes", Biochemical Society Transactions, (2008) vol. 36, No. 5, pp. 1091-1096.
Margulies et al., Sep. 15, 2005 Genome sequencing in microfabricated high-density picolitre reactors, Nature, 437:376-380.

(56) References Cited

OTHER PUBLICATIONS

Martinez et al., Jul. 2012, A microfluidic approach to encapsulate living cells in uniform alginate hydrogel microparticles, Macromol. Biosci, 12(7):946-951.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Meyer et al., "Parallel tagged sequencing on the 454 platform", Nature Protocols, (2008) vol. 3, No. 2, pp. 267-278.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.
Murinae, Wikipedia.org, accessed Mar. 18, 2013, 21 pp.
Nadai et al., 2008, Protocol for nearly full-length sequencing of HIV-1 RNA from plasma, PLoS One, 3(1):e1420.
Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Patanjali et al., Mar. 1991, Construction of a uniform-abundance (normalized) CNDA library, Proceedings of the National Academy of Sciences, 88(5):1943-1947.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Perez-Rentero et al., 2012, Synthesis of oligonucleotides carrying thiol groups using a simple reagent derived from threoninol, Molecules, 17:10026-10045.
Peterson et al., Jun. 2017, Multiplexed quantification of proteins and transcripts in single cells, Nature Biotechnology, 10 pp.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Plant, Wikipedia.org, accessed Aug. 28, 2015, 14 pp.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Poole et al., 2007, Measuring global gene expression in polyploidy; a cautionary note from allohexaploid wheat, Funct. Integr Genomics, 7:207-219.
Protozoa, Wikipedia.org, accessed May 11, 2016, 10 pp.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Robinson et al., 2010, A scaling normalization method for differential expression analysis of RNA-seq data, Genome Biology, 11:R25.
Roche Diagnostics GmbH, 2006, Genome Sequencer 20 System: First to the Finish (product brochure), 40 pp.
Sano et al., Oct. 2, 1992, Immuno-PCR: very sensitive antigen detection by means of specific antibody-DNA conjugates, Science 258:120-122.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shahi et al., Mar. 14, 2017, Abseq: ultrahigh-throughput single cell protein profiling with droplet microfluidic barcoding, Scientific Reports, 12 pp.
Shalek et al., Jun. 13, 2013, Single-cell transcriptomics reveals bimodality in expression and splicing in immune cells. Nature. 498(7453):236-240.
Shendure et al., "Next-generation DNA sequencing", Nature Biotechnology, (Oct. 2008) vol. 26, No. 10, pp. 1135-1145.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.
Smith et al., 2010, Highly-multiplexed barcode sequencing: an efficient method for parallel analysis of pooled samples. Nucleic Acids Research, 38(13):e142.
Solomatin et al., 2009, Methods of site-specific labling of NRA with fluorescent dyes, Methods in Enzymology, vol. 469, 22 pp.
Sommer et al., Nov. 16, 1989, Minimal homology requirements for PCR primers, Nucleic Acids Research, 17(16):6749.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Stoeckius et al., Mar. 2, 2017, Large-scale simultaneous measurement of epitopes and transcriptomes in single cells, 27 pp.
Stratagene 1998 Catalog, Gene Characterization Kits, p. 39.

(56) References Cited

OTHER PUBLICATIONS

Subkhankulova et al., "Comparative evaluation of linear and exponential amplification techniques for expression profiling at the single cell level", Genome Biology, (Mar. 2006) vol. 7, No. R18, pp. 1-16.
Takahashi et al., Mar. 2006, Novel technique of quantitative nested real-time PCR assay for mycobacterium tuberculosis DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Tang et al, "RNA-Seq analysis to capture the transcriptome landscape of a single cell", Nature Protocols, (2010) vol. 5, No. 3, pp. 516-535.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Ullal et al., Jan. 15, 2014, Cancer cell profiling by barcoding allows multiplexed protein analysis in fine needle aspirates, Sci Transl Med., 6(219), 22 pp.
Van Buggenum et al., 2016, A covalent and cleavable antibody-DNA conjugation strategy for sensitive protein detection via immuno-PCR, Nature, Scientific Reports, 12 pp.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Virus, Wikipedia.org, accessed Nov. 24, 2012, 34 pp.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., Jul. 2007, Combining gold nanoparticles with real-time immune-PCR for analysis of HIV p24 antigens, Proceedings of ICBBE 2007, IEEE, Piscataway, NJ, pp. 1198-1201.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weibrecht et al., Jan. 2010, Proximity ligation assays; recent addition to the proteomics toolbox, Expert Review of Proteo, Future Drugs Ltd., London, GB, 7(3):401-409.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zalipsky, Mar. 1995, Bioconjugate Chemistry, 6:150-165.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
Zhou et al., Jan. 2012, Photocleavable peptide-oligonucleotide conjugates for protein kinase assays, by MALDI-TOF MS, Molecular Biosystems, 8(9):2395.
Zhu et al., "Reverse transcriptase template switching: a SMART approach for full-length cDNA library construction.", BioTechniques, (Apr. 2001) vol. 30, No. 4, pp. 892-897.
Office Action dated Sep. 8, 2017 in U.S. Appl. No. 15/046,225.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office Action dated Jan. 9, 2018 in U.S. Appl. No. 15/217,896.
Office Action dated Jan. 12, 2018 in U.S. Appl. No. 15/217,886.
Office Action dated Oct. 11, 2016 in U.S. Appl. No. 15/224,460.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.

(56) References Cited

OTHER PUBLICATIONS

Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.
Office Action dated Jun. 7, 2017 in U.S. Appl. No. 14/381,488.
International Search Report and Written Opinion dated Sep. 6, 2013 in PCT/US13/028103.
Examination Report No. 1 for standard patent application, dated Oct. 24, 2017, Australian patent application No. 2013226081.
Office Action dated Feb. 17, 2017 in Canadian patent application No. 2,865,575.
Office Action dated Jun. 6, 2016 in Chinese patent application No. 201380022187.9.
Office Action dated Dec. 27, 2016 in Chinese patent application No. 201380022187.9.
Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Final Decision dated Aug. 30, 2017 in Japanese patent application No. 2014-558975.
Search Report and Written Opinion dated Mar. 1, 2016 in Singapore patent application No. 11201405274W.
Written Opinion dated May 26, 2017 in Singapore patent application No. 11201405274W.
International search report and written opinion dated Aug. 16, 2013 for PCT/US2013/027891.
Extended European Search Report dated Dec. 14, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US/14/053301.
Examination Report dated Apr. 10, 2017 in European patent application No. 14761937.3.
Examination Report dated Oct. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
Examination Report dated Jan. 3, 2018 in GB patent application No. 1609740.4.
Third Party Observation dated Jun. 14, 2018 in Japanese patent application No. 2016-537867.
Official Action dated Jul. 30, 2018 in Japanese patent application No. 2016-537867.
Office Action dated May 13, 2016 in U.S. Appl. No. 14/508,911.
Office Action dated Mar. 24, 2017 in U.S. Appl. No. 15/409,355.
Office Action dated Oct. 16, 2017 in U.S. Appl. No. 15/409,355.
International search report and written opinion dated Dec. 19, 2014 for PCT Application No. US2014/059542.
International Search Report and Written Opinion dated Jun. 20, 2016 in PCT/US16/14612.
Office Action dated Jan. 19, 2017 in U.S. Appl. No. 15/055,445.
Office Action dated Nov. 1, 2017 in U.S. Appl. No. 15/667,125.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
Office Action dated Sep. 8, 2017 in U.S. Appl. No. 15/134,967.
International Search Report and Written Opinion dated Sep. 28, 2016 in PCT/US16/028694.
International Search Report and Written Opinion dated Sep. 27, 2016 in PCT/US16/034473.
Office Action dated Jan. 7, 2020 in U.S. Appl. No. 15/574,122.
Office Action dated Jul. 14, 2020 in U.S. Appl. No. 15/574,122.
International Search Report and Written Opinion dated Jan. 31, 2017 in PCT/US16/050694.
International Search Report and Written Opinion dated Sep. 8, 2017 in PCT/US2017/030097.
International Search Report and Written Opinion dated Aug. 7, 2017 in PCT/US2017/034576.
International Search Report and Written Opinion dated Mar. 20, 2018 in application No. PCT/US2017/053331.
International Search Report and Written Opinion dated Jul. 16, 2018 in application No. PCT/US2018/024602.
Office Action dated Nov. 26, 2018 in U.S. Appl. No. 15/937,713.
Pre-interview communication dated Nov. 27, 2018 in U.S. Appl. No. 16/012,635.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
Statement of Opposition of Strawman Limited filed against European Patent No. EP2414548B1 on Jul. 19, 2016.
Statement of Opposition filed against European Patent No. EP2414548B1 on Jul. 26, 2016.
Statement of Opposition filed against European Patent No. EP2414548B1 on Jul. 21, 2016.
Submission dated Jan. 15, 2018 by Strawman Limited in preparation for upcoming oral proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 16, 2018 for U.S. Appl. No. 15/847,752.
Third-Party Pre-Issuance Submission filed on Jun. 6, 2018 for U.S. Appl. No. 15/847,752.
Third-Party Pre-Issuance Submission filed on May 21, 2018 for U.S. Appl. No. 15/847,752.
International Search Report and Written Opinion dated Jul. 21, 2020 in application No. PCT/US2020/028212.

* cited by examiner

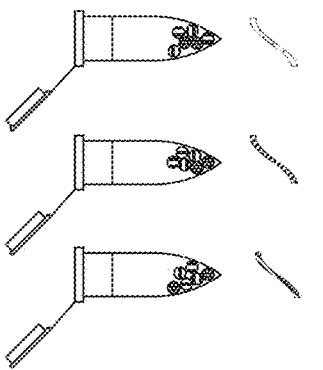
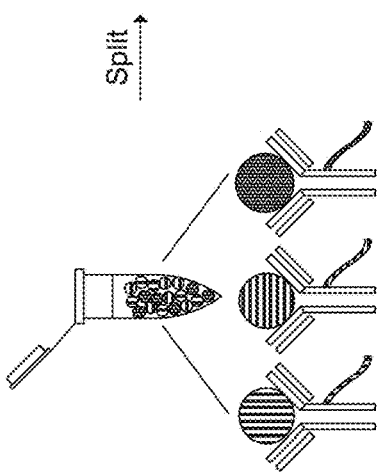
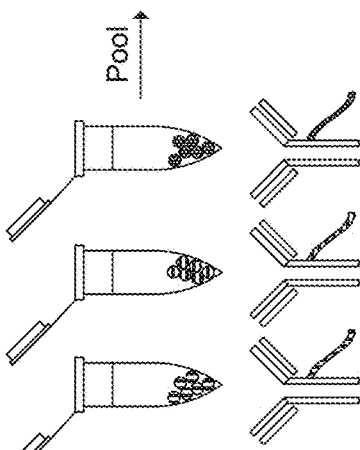
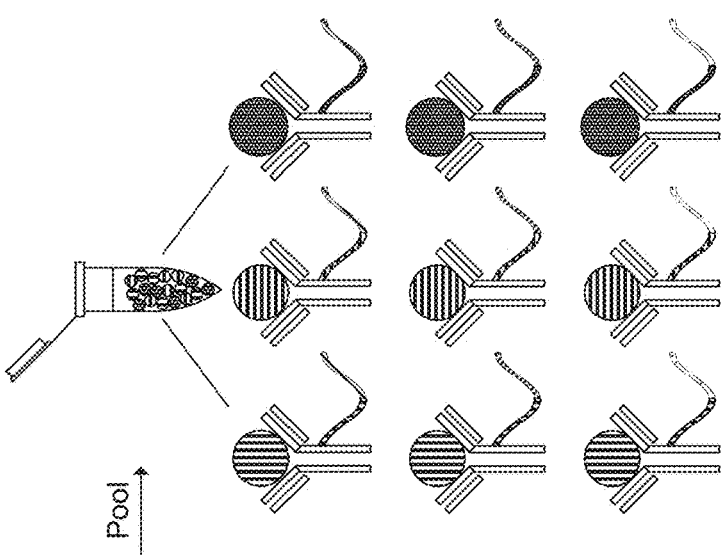
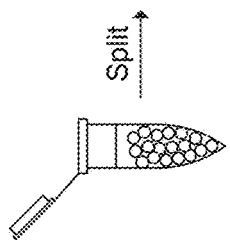
FIG. 6

FIG. 10A 95mer oligo design.
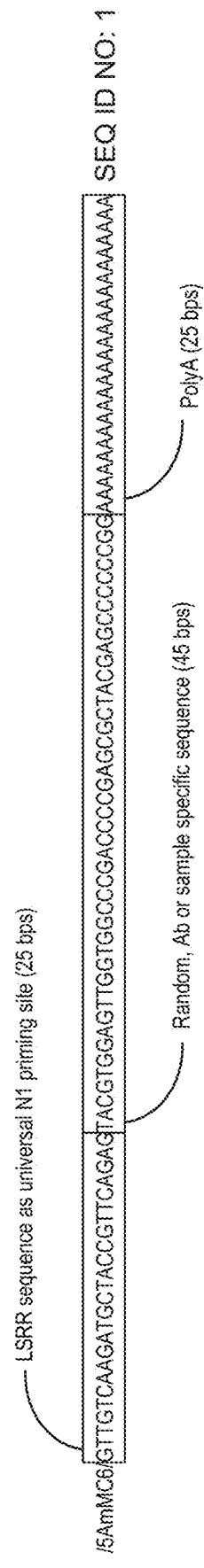
FIG. 10B 200mer oligo design. Targeted amplification scheme (nested specific).
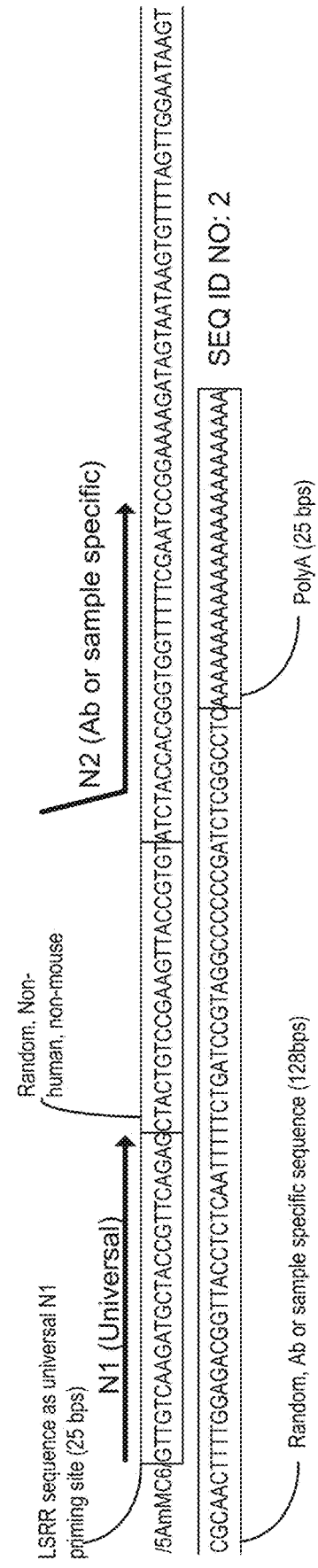

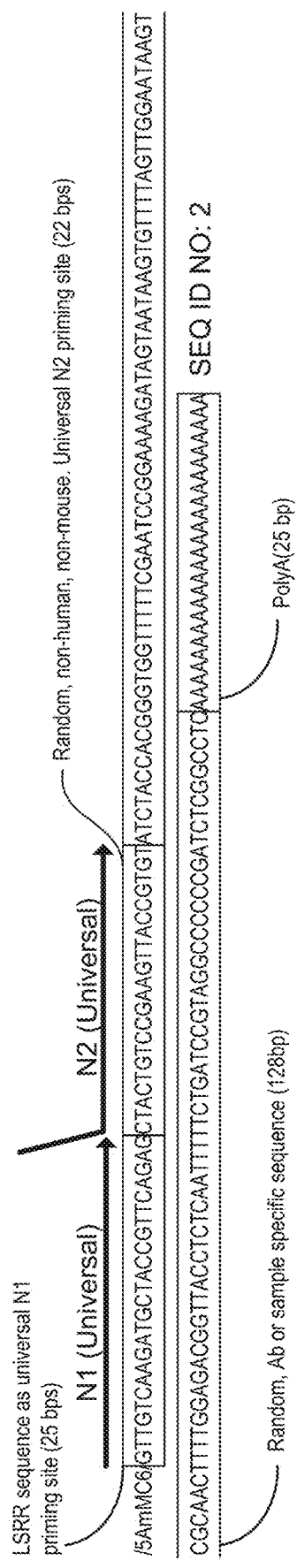
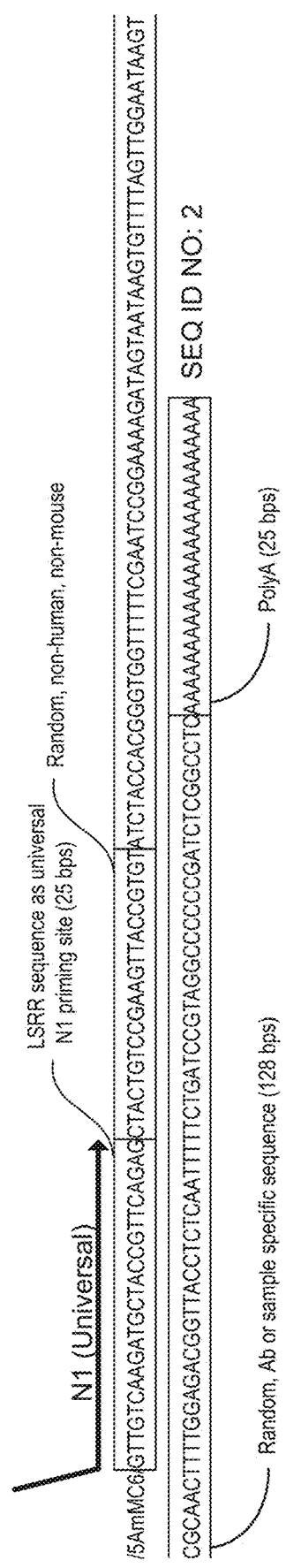

METHODS OF ASSOCIATING PHENOTYPICAL DATA AND SINGLE CELL SEQUENCING DATA

RELATED APPLICATIONS

The present application claims priority under 35 U.S.C. § 119(e) to U.S. Provisional Application No. 62/836,504, filed on Apr. 19, 2019. The content of this related application is herein expressly incorporated by reference in its entirety.

BACKGROUND

Field

The present disclosure relates generally to the field of molecular biology, for example linking single cell sequencing data (e.g., expression profiling) with phenotypic data and/or drug exposure.

Description of the Related Art

Current technology allows measurement of gene expression of single cells in a massively parallel manner (e.g., >10000 cells) by attaching cell specific oligonucleotide barcodes to poly(A) mRNA molecules from individual cells as each of the cells is co-localized with a barcoded reagent bead in a compartment. Current single-cell multiomics workflows also possess the capacity for capturing phenotypic data (e.g., imaging data) of single cells. Furthermore, as disclosed herein, single cells can be exposed different concentrations and/or different types of one or more agents. There is a need for systems and methods for associating single cell sequencing data with phenotypic data and/or agent exposure.

SUMMARY

Disclosed herein include methods for labeling a plurality of cells with cell indexing oligonucleotides. In some embodiments, the method comprises: (a) associating cells in each first partition of a plurality of first partitions with a cellular component-binding reagent of a plurality of cellular component-binding reagents, wherein each of the cells comprises one or more cellular component targets, wherein the cellular component-binding reagent is associated with a first indexing oligonucleotide with a first cell indexing subsequence, wherein two cellular component-binding reagents of the plurality of cellular component-binding reagents are associated with first indexing oligonucleotides with different first cell indexing subsequences, and wherein the cellular component-binding reagent is capable of specifically binding to the one or more cellular component targets, thereby generating cells associated with the first cell indexing subsequence, in each first partition of the plurality of first partitions, via the cellular component-binding reagent the first indexing oligonucleotide with the first cell indexing subsequence is associated with, wherein the cells in two first partitions of the plurality of first partitions are associated with different first cell indexing subsequences. The method can comprise (b) pooling the cells associated with the cellular component-binding reagents in each first partition of the plurality of first partitions. The method can comprise (c) distributing the pooled cells into a plurality of second partitions. The method can comprise (d) associating the pooled cells in each second partition of the plurality of second partitions with a second indexing oligonucleotide of a plurality of second indexing oligonucleotides with a second cell indexing subsequence, wherein the second indexing oligonucleotides of the plurality of second indexing oligonucleotides in two second partitions of the plurality of second partitions comprise different second cell indexing subsequences, thereby generating cells associated with the second cell indexing subsequence, in each second partition of the plurality of second partitions, wherein the cells in two second partitions of the plurality of second partitions are associated with different second cell indexing subsequences. The method can comprise (e) generating cells associated with the cellular component-binding reagent in each second partition of the plurality of second partitions associated with a cell indexing oligonucleotide, wherein the cell indexing sequence of the cell indexing oligonucleotide comprises the first cell indexing subsequence and the second cell indexing subsequence of the second cell indexing oligonucleotide associated with the second partition of the plurality of second partitions, via the cellular component-binding reagent associated with the first indexing oligonucleotide with the first cell indexing subsequence associated with each of the cells in the second partition.

In some embodiments, the method comprises, after step (e): (f) pooling the cells associated with the cellular component-binding reagents in each second partition of the plurality of second partitions. In some embodiments, the method comprises, prior to step (a): distributing cellular component-binding reagents of the plurality of cellular component-binding reagents into the plurality of first partitions. In some embodiments, the method comprises pooling the cells associated with the cellular component-binding reagent in each first partition of the plurality of first partitions. In some embodiments, the method comprises removing unbound first indexing oligonucleotides. In some embodiments, the first indexing oligonucleotide comprises a linker, and wherein the cellular component-binding reagent is associated with the first indexing oligonucleotide via the linker. In some embodiments, the first indexing oligonucleotide is a single-stranded oligonucleotide. In some embodiments, the 5' end of the first indexing oligonucleotide comprises the linker. In some embodiments, the second indexing oligonucleotide is a single-stranded oligonucleotide. In some embodiments, the first indexing oligonucleotide comprises a first linker sequence. In some embodiments, the second indexing oligonucleotide comprises a complementary sequence of the first linker sequence. In some embodiments, the generating comprises hybridizing the first linker sequence of the first indexing oligonucleotide to the complementary sequence of the first linker sequence of the second indexing oligonucleotide, thereby generating a hybridized indexing oligonucleotide. In some embodiments, the generating comprises extending the first indexing oligonucleotide of the hybridized indexing oligonucleotide, thereby generating the first cell indexing oligonucleotide comprising the first cell indexing sequence and the second cell indexing sequence. In some embodiments, the extending comprises extending the first indexing oligonucleotide of the hybridized indexing oligonucleotide using a DNA polymerase, a reverse transcriptase, or any combination thereof. In some embodiments, the DNA polymerase is a Klenow large fragment.

In some embodiments, the first indexing oligonucleotide is hybridized to a first complementary indexing oligonucleotide. In some embodiments, the first complementary indexing oligonucleotide comprises a first linker sequence, wherein the second indexing oligonucleotide comprises a complementary sequence of the first linker sequence, and wherein the generating comprises hybridizing the first linker sequence of the first complementary indexing oligonucleotide to the complementary sequence of the first linker sequence of the second indexing oligonucleotide, thereby generating a hybridized indexing oligonucleotide. In some embodiments, the second indexing oligonucleotide is hybridized to a second complementary indexing oligonucleotide. In some embodiments, the first indexing oligonucleotide comprises a first linker sequence, wherein the second complementary indexing oligonucleotide comprises a complementary sequence of the first linker sequence, and wherein the generating comprises hybridizing the first linker sequence of the first indexing oligonucleotide to the complementary sequence of the first linker sequence of the second complementary indexing oligonucleotide, thereby generating a hybridized indexing oligonucleotide. In some embodiments, the first linker sequence comprises a first restriction site recognized by a first restriction enzyme, wherein the second indexing oligonucleotide comprises a second restriction site recognized by a second restriction enzyme, and wherein the first and second restriction sites comprise different restriction sites. In some embodiments, the method comprises ligating the first indexing oligonucleotide with the second indexing oligonucleotide.

In some embodiments, the method comprises removing the first complementary indexing oligonucleotide or the second complementary indexing oligonucleotide. In some embodiments, the removing comprises contacting the hybridized indexing oligonucleotide with an enzyme with 5' to 3' exonuclease activity. In some embodiments, the enzyme with 5' to 3' exonuclease activity is Lamba exonuclease.

In some embodiments, the method comprises performing steps (c), (d), (e), and (f) for n times, wherein n is a positive integer greater than 1. In some embodiments, the nth indexing oligonucleotide comprises an (n−1)th linker sequence and a target sequence. In some embodiments, the target sequence comprises a poly(A) sequence. In some embodiments, the cell indexing oligonucleotide comprises cell indexing subsequence$_1$-linker sequence-cell indexing subsequence$_2$-linker sequence$_2$- . . . cell indexing subsequence$_{n-1}$-linker sequence$_n$-cell indexing subsequence$_n$-target sequence. In some embodiments, two of the linker sequences are identical. In some embodiments, all linker sequences are identical. In some embodiments, two of the linker sequences are different. In some embodiments, all linker sequences are different. In some embodiments, the second indexing oligonucleotide comprises a second linker sequence. In some embodiments, step (b) comprises removing unbound cellular component-binding reagents.

In some embodiments, the plurality of the first partitions and the plurality of the second partitions comprise an identical number of partitions. In some embodiments, two pluralities of partitions comprise an identical number of partitions. In some embodiments, each of the pluralities of partitions comprises an identical number of partitions. In some embodiments, the plurality of the first partitions and the plurality of the second partitions comprise different numbers of partitions. In some embodiments, two pluralities of partitions comprise different numbers of partitions. In some embodiments, each of the pluralities of partitions comprises different numbers of partitions. In some embodiments, two pluralities of partitions comprise different numbers of partitions.

In some embodiments, the cell indexing sequence of the cell indexing oligonucleotide comprises n cell indexing subsequences. In some embodiments, n is an integer from 2 to 20. In some embodiments, linker sequences are about 1 nucleotide to about 50 nucleotides in length. In some embodiments, cell indexing subsequences are about 1 nucleotide to about 50 nucleotides in length. In some embodiments, the linker comprises a chemical group. In some embodiments, the chemical group is reversibly attached to the first indexing oligonucleotide. In some embodiments, the cellular component-binding reagent comprises a chemical group. In some embodiments, the chemical group comprises a UV photocleavable group, a streptavidin, a biotin, an amine, a disulfide linkage, or any combination thereof. In some embodiments, the linker comprises a 5' amine. In some embodiments, the linker comprises a carbon chain. In some embodiments, the carbon chain comprises 2-30 carbons.

In some embodiments, the first indexing oligonucleotide is covalently attached to the cellular component-binding reagent. In some embodiments, the first indexing oligonucleotide is conjugated to the cellular component-binding reagent. In some embodiments, first indexing oligonucleotide is conjugated to the cellular component-binding reagent through a chemical group selected from the group consisting of a UV photocleavable group, a streptavidin, a biotin, an amine, and a combination thereof. In some embodiments, the first indexing oligonucleotide is non-covalently attached to the cellular component-binding reagent. In some embodiments, the first indexing oligonucleotide is configured to be detachable from the cellular component-binding reagent. In some embodiments, the cellular component binding reagent comprises an antibody, a tetramer, an aptamer, a protein scaffold, or a combination thereof. In some embodiments, the cellular component binding reagent comprises a protein binding reagent. In some embodiments, the protein binding reagent is an antibody. In some embodiments, the antibody comprises an immunoglobulin G (IgG), a F(ab') fragment, a F(ab')$_2$ fragment, a combination thereof, or a fragment thereof.

In some embodiments, each cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences. In some embodiments, the method comprises determining the cell indexing sequences. In some embodiments, the cell indexing oligonucleotide is associated with a spatial index. In some embodiments, the method comprises determining the spatial index using n pluralities of probes. In some embodiments, determining the spatial index comprises sequentially hybridizing and imaging the n pluralities of probes annealing to the n cell indexing subsequences. In some embodiments, the n pluralities of probes comprise one or more detectable moieties, wherein imaging comprises detecting the one or more detectable moieties. In some embodiments, the detectable moieties of the probes comprise fluorescent labels, wherein sequential hybridization and imaging comprises sequential hybridization and fluorescent imaging. In some embodiments, the method comprises determining the cell indexing sequence from the spatial index. In some embodiments, the cell indexing oligonucleotide comprises two cell indexing subsequences, wherein the cell indexing subsequences anneal to different probes. In some embodiments, the method comprises partitioning the plurality of cells associated with one or more unique cell indexing oligonucleotides. In some embodiments, partitioning the plurality of cells associated with one or more unique cell indexing oligonucleotides comprises partitioning the plurality of cells associated with one or more unique cell indexing oligonucleotides to a plurality of partitions, wherein a partition of the plurality of partitions comprises the single cell from the plurality of cells associated with one or more unique cell indexing oligonucleotides.

In some embodiments, the method comprises dissociating the cell indexing oligonucleotide from the cellular component-binding reagent. In some embodiments, dissociating the cell indexing oligonucleotide comprises detaching the cell indexing oligonucleotide from the cellular component-binding reagent by UV photocleaving, chemical treatment, heating, enzyme treatment, or any combination thereof. In some embodiments, the dissociating occurs after stochastically labeling the cell indexing oligonucleotide. In some embodiments, the dissociating occurs before stochastically labeling the cell indexing oligonucleotide. In some embodiments, the target sequence comprises a sequence complementary to a capture sequence of a stochastic label configured to capture the sequence of the cell indexing oligonucleotide.

Disclosed herein include methods for generating a spatial index. In some embodiments, the method comprises: (a) contacting a cell indexing oligonucleotide with a plurality of first probes, wherein one or more of the probes of the plurality of first probes comprise a detectable moiety, or precursor thereof, wherein the cell indexing oligonucleotide comprises a series of n cell indexing subsequences, wherein n is an integer greater than 1, and wherein probes selectively anneal to cell indexing subsequences with complementary sequences; (b) removing unannealed probes; (c) imaging the cell indexing oligonucleotide, wherein imaging comprises detecting a signal of the detectable moiety; (d) removing the annealed probes and/or the detectable moieties thereof; and (e) repeating the steps (a)-(d) for a total of n cycles, wherein each nth cycle comprises contacting a plurality of nth probes with the cell indexing oligonucleotide, whereby a spatial index is generated for the cell indexing oligonucleotide, wherein the spatial index comprises a series of n signals and/or absence of signals detected in the n cycles.

In some embodiments, each nth cell indexing subsequence of the series of n cell indexing subsequences is selected from p unique cell indexing subsequences, wherein p is an integer greater than 1. In some embodiments, during each nth cycle a plurality of nth probes selectively anneal to the nth position of the series of n cell indexing subsequences. In some embodiments, each plurality of nth probes comprises p unique probes, wherein unique probes selectively anneal to different cell indexing subsequences, and wherein p is an integer greater than 1. In some embodiments, m probes of the p unique probes comprise a detectable moiety, or precursor thereof, wherein m is an integer greater than 1, and wherein m is p−1. In some embodiments, the absence of signal during an imaging step is due to annealing of a probe that does not comprise a detectable moiety.

In some embodiments, each plurality of nth probes comprises m unique probes, wherein unique probes selectively anneal to different cell indexing subsequences, wherein m is an integer greater than 1, and wherein m is p−1. In some embodiments, the m unique probes comprise a detectable moiety, or precursor thereof. In some embodiments, during each cycle of the n cycles, one unique cell indexing subsequence of the p unique cell indexing subsequences is not annealed by a probe. In some embodiments, the absence of signal during an imaging step is due the absence of annealing of a probe to a cell indexing subsequence.

In some embodiments, the cell indexing oligonucleotide comprises a cell indexing sequence, wherein the cell indexing sequence of the cell indexing oligonucleotide comprises the n cell indexing subsequences. In some embodiments, the cell indexing oligonucleotide is associated with a synthetic particle. In some embodiments, the synthetic particle comprises a plurality of stochastic labels, wherein the stochastic labels are oligonucleotides, and wherein a stochastic label comprises the cell indexing oligonucleotide. In some embodiments, the synthetic particle comprises a plurality of stochastic labels, wherein the stochastic labels are oligonucleotides, and wherein a stochastic label comprises the cell indexing sequence. In some embodiments, the stochastic label comprises a cellular label. In some embodiments, the cellular label comprises the cell indexing sequence.

In some embodiments, a unique cell indexing subsequence occurs at only one position within the series of n cell indexing subsequences. In some embodiments, the series of n cell indexing subsequences are linked in a tandem manner. In some embodiments, the series of n cell indexing subsequences comprise one or more linker sequences separating two or more cell indexing subsequences. In some embodiments, the total number of unique probes is $n*p$. In some embodiments, the total number of unique probes is $n*m$. In some embodiments, the total number of unique cell indexing subsequences is $n*p$.

In some embodiments, the cell indexing oligonucleotide is single-stranded. In some embodiments, the method comprises rendering the cell indexing oligonucleotide single-stranded prior to contacting with the first plurality of probes. In some embodiments, imaging comprises optical microscopy, fluorescence microscopy, confocal microscopy, electron microscopy, or any combination thereof. In some embodiments, removing the unannealed probes comprises washing the cell indexing oligonucleotide with a washing buffer. In some embodiments, the selective annealing is performed under stringent hybridization conditions. In some embodiments, the stringent hybridization conditions allow annealing to occur if sequence complementary is greater than 90%. In some embodiments, the ratio of cell indexing oligonucleotide to probe during the contacting step is about 100:1 to about 1:1. In some embodiments, the ratio of cell indexing oligonucleotide to probe during the contacting step is about 1:1 to about 1:100.

In some embodiments, the sequence of each probe is known, wherein the detectable moiety of each probe is known, wherein the identity of the series of n cell indexing subsequences is not known, and wherein the selective annealing of an nth probe to the nth cell indexing subsequence of the series of n cell indexing subsequences identifies the nth cell indexing subsequence. In some embodiments, the identity of the n cell indexing subsequences is unknown before the method is performed. In some embodiments, the identity of the n cell indexing subsequences is unknown prior to placement of the cell indexing oligonucleotide in a partition. In some embodiments, generating the spatial index of the cell indexing oligonucleotide enables a determination of the n cell indexing subsequences of the cell indexing oligonucleotide. In some embodiments, generating the spatial index of the cell indexing oligonucleotide enables a determination of the cell indexing sequence of the cell indexing oligonucleotide. In some embodiments, the detectable moiety, or precursor thereof, of the m probes is selected from a set of m spectrally distinct moieties. In some embodiments, the set of m spectrally distinct moieties is identical for each of nth plurality of probes.

In some embodiments, the probe comprises an oligonucleotide. In some embodiments, the oligonucleotide comprises a DNA, a RNA, a morpholino, a locked nucleic acid (LNA), a peptide nucleic acid (PNA), a DNA, an LNA/PNA chimera, an LNA/DNA chimera, a PNA/DNA chimera, or any combination thereof. In some embodiments, the m probes comprise a single detectable moiety, or precursor thereof. In some embodiments, the single detectable moieties of each of the m probes are spectrally-distinct detectable moieties. In some embodiments, the m probes each comprise a plurality of detectable moieties, or precursors thereof. In some embodiments, the m probes comprises a first detectable moiety and second detectable moiety, and wherein the first detectable moiety and the second detectable moiety are selected from a group comprising two or more spectrally-distinct detectable moieties. In some embodiments, the detectable moiety comprises an optical moiety, a luminescent moiety, an electrochemically active moiety, a nanoparticle, or a combination thereof. In some embodiments, the luminescent moiety comprises a chemiluminescent moiety, an electroluminescent moiety, a photoluminescent moiety, or a combination thereof. In some embodiments, the photoluminescent moiety comprises a fluorescent moiety, a phosphorescent moiety, or a combination thereof. In some embodiments, the fluorescent moiety comprises a fluorescent dye. In some embodiments, the nanoparticle comprises a quantum dot. In some embodiments, the method comprises performing a reaction to convert the detectable moiety precursor into the detectable moiety.

In some embodiments, removing the annealed probes and/or the detectable moieties thereof comprises removing the detectable moiety. In some embodiments, removing the detectable moiety comprises photobleaching. In some embodiments, the detectable moiety is attached to the probe via a linker. In some embodiments, the linker comprises a restriction site, and wherein removing the detectable moiety comprises addition of a restriction enzyme. In some embodiments, the detectable moiety and the probe are connected through a cleavable linkage selected from the group consisting of a chemically cleavable linkage, a photocleavable linkage, an acid labile linker, a heat sensitive linkage, an enzymatically cleavable linkage, or any combination thereof. In some embodiments, removing the annealed probes and/or the detectable moieties thereof comprises removing the annealed probe. In some embodiments, removing the annealed probe comprises heating. In some embodiments, removing the annealed probe comprises the addition an exonuclease. In some embodiments, the exonuclease comprises 3' to 5' exonuclease activity and wherein the 5' end of the cell indexing oligonucleotide is associated with a synthetic particle or a cellular component-binding reagent. In some embodiments, the exonuclease comprises 5' to 3' exonuclease activity and wherein the 3' end of the cell indexing oligonucleotide is associated with a synthetic particle or a cellular component-binding reagent.

In some embodiments, the number of unique spatial indices that can be generated is equal to or less than $(1+m)^n$. In some embodiments, p is an integer from 2 to 15. In some embodiments, m is an integer from 2 to 15. In some embodiments, n is an integer from 2 to 15. In some embodiments, n is 4, and wherein m is 9 or 10. In some embodiments, n is 5, and wherein m is 6, 7, 8, 9 or 10. In some embodiments, n is 6, and wherein m is 4, 5, 6, 7, 8, or 9. In some embodiments, n is 7, and wherein m is 3, 4, 5, 6, or 7. In some embodiments, n is 8, and wherein m is 3, 4, or 5. In some embodiments, n is 9, and wherein m is 2, 3, or 4. In some embodiments, n is 10, and wherein m is 2 or 3. In some embodiments, p is m+1.

In some embodiments, the method is multiplexed. In some embodiments, the method comprises generating a spatial index of a plurality of unique cell indexing oligonucleotides. In some embodiments, each unique cell indexing oligonucleotide of the plurality of unique cell indexing oligonucleotides is contacted with probes in spatial isolation from the other unique cell indexing oligonucleotides. In some embodiments, the method comprises, prior to step (a), partitioning a plurality of unique cell indexing oligonucleotides to a plurality of partitions, wherein a partition of the plurality of partitions comprises one or more copies of a single unique cell indexing oligonucleotide. In some embodiments, the plurality of partitions comprises microwells of a microwell array. In some embodiments, the plurality of partitions comprises a plurality of droplets. In some embodiments, the cell indexing sequences of unique cell indexing oligonucleotides are different. In some embodiments, spatial indices of unique cell indexing oligonucleotides are different. In some embodiments, the method comprises generating a spatial index of at least 96 unique cell indexing oligonucleotides. In some embodiments, the method comprises generating a spatial index of at least 1,000 unique cell indexing oligonucleotides. In some embodiments, the method comprises generating a spatial index of at least 10,000 unique cell indexing oligonucleotides. In some embodiments, the plurality of partitions are imaged sequentially. In some embodiments, the plurality of partitions are imaged simultaneously.

In some embodiments, a unique cell indexing oligonucleotide is associated with a particle. In some embodiments, the particle is a cell. In some embodiments, the particle is a synthetic particle. In some embodiments, the synthetic particle is a bead. In some embodiments, the bead is selected from the group comprising silica gel beads, controlled pore glass beads, magnetic beads, Dynabeads, Sephadex/Sepharose beads, cellulose beads, polystyrene beads, or any combination thereof.

In some embodiments, two or more partitions of the plurality of partitions comprise a single cell. In some embodiments, two or more partitions of the plurality of partitions comprise a single bead. In some embodiments, the single cell is associated with one or more unique cell indexing oligonucleotides, wherein the one or more cell indexing oligonucleotides associated with the same cell comprise the same cell indexing sequence, and wherein the one or more cell indexing oligonucleotides associated with cells in different partitions comprise different cell indexing sequences. In some embodiments, the single bead is associated with one or more unique cell indexing oligonucleotides, wherein the one or more cell indexing oligonucleotides associated with the single bead comprise the same cell indexing sequence, and wherein the one or more cell indexing oligonucleotides associated with beads in different partitions comprise different cell indexing sequences. In some embodiments, two or more partitions of the plurality of partitions comprise a single bead and a single cell, wherein the single bead is associated with one or more unique cell indexing oligonucleotides, wherein the one or more cell indexing oligonucleotides associated with the single bead comprise the same cell indexing sequence, and wherein the one or more cell indexing oligonucleotides associated with beads in different partitions comprise different cell indexing sequences. In some embodiments, two or more partitions of the plurality of partitions comprise a single bead and a single cell, wherein the single cell is associated with one or more unique cell indexing oligonucleotides, wherein the one or more cell indexing oligonucleotides associated with the same cell comprise the same cell indexing sequence, and wherein the one or more cell indexing oligonucleotides associated with cells in different partitions comprise different cell indexing sequences.

Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (c) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (d) determining the spatial location of each nucleic acid target molecule by associating the cellular label of the partition and the cell indexing sequence of the partition, wherein the spatial location comprises the identity of the partition from which the nucleic acid target molecule originated.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) obtaining phenotypic data for each single cell; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the phenotypic data and the sequencing data of each single cell by associating the cellular label of the partition and the cell indexing sequence for each nucleic acid target molecule.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the agent exposure and the sequencing data of each single cell by associating the cellular label of the partition and the cell indexing sequence for each nucleic acid target molecule.

Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) stochastically labeling the nucleic acid target molecules using the plurality of stochastic labels to generate a plurality of stochastically labeled nucleic acid target molecules; (c) obtaining the sequencing data of the plurality of stochastically labeled nucleic acid target molecules, wherein obtaining the sequencing data comprises sequencing at least a portion of the cell indexing sequence; and (d) determining the spatial location of each nucleic acid target based on the cell indexing sequence, wherein the spatial location comprises the identity of the partition from which the nucleic acid target molecule originated.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) obtaining phenotypic data for each single cell; (c) stochastically labeling the nucleic acid target molecules using the plurality of stochastic labels to generate a plurality of stochastically labeled nucleic acid target molecules; (d) obtaining the sequencing data of the plurality of stochastically labeled nucleic acid target molecules, wherein obtaining the sequencing data comprises sequencing at least a portion of the cell indexing sequence; and (e) associating the phenotypic data and the sequencing data of each single cell based on the cell indexing sequence.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the nucleic acid target molecules using the plurality of stochastic labels to generate a plurality of stochastically labeled nucleic acid target molecules; (d) obtaining the sequencing data of the plurality of stochastically labeled nucleic acid target molecules, wherein obtaining the sequencing data comprises sequencing at least a portion of the cell indexing sequence; and (e) associating the agent exposure and the sequencing data of each single cell based on the cell indexing sequence.

In some embodiments, the method comprises: i) obtaining phenotypic data for each single cell; and ii) associating the phenotypic data and the sequencing data of each single cell based on the cell indexing sequence. In some embodiments, the method comprises: i) generating the spatial index of the unique cell indexing oligonucleotide of each partition to identify the spatial index of each partition; and ii) determining the cell indexing sequence of each partition based on the spatial index of each partition. In some embodiments, the method comprises: i) generating the spatial index of the cell indexing sequence of each partition to identify the spatial index of each partition; and ii) determining the cell indexing sequence of each partition based on the spatial index of each partition.

In some embodiments, the plurality of stochastic labels are associated with a synthetic particle, and wherein each partition comprises a single synthetic particle. In some embodiments, each of the plurality of stochastic labels comprises a molecular label sequence, wherein molecular label sequences of at least two stochastic labels of the plurality of stochastic labels comprise different molecule label sequences. In some embodiments, each synthetic particle is associated with one or more unique cellular labels, wherein the one or more unique cellular labels associated with the same synthetic particle comprise the same sequence, and wherein the one or more unique cellular labels associated with different synthetic particles comprise different sequences. In some embodiments, each of the plurality of stochastic labels comprises a target nucleic acid binding region, wherein the target nucleic acid binding region comprises a sequence selected from the group consisting of a gene-specific sequence, an oligo-dT sequence, a random multimer, and any combination thereof. In some embodiments, the stochastic labels and/or cell indexing oligonucleotides are immobilized on the synthetic particle, partially immobilized on the synthetic particle, enclosed in the synthetic particle, partially enclosed in the synthetic particle, or a combination thereof. In some embodiments, the synthetic particle comprises silica gel, controlled pore glass, Wang resin, Merrifield resin, a Dynabead, a Sephadex bead, a Sepharose bead, a cellulose bead, polystyrene bead, or any combination thereof. In some embodiments, the synthetic particle comprises a material selected from the group consisting of polydimethylsiloxane (PDMS), polystyrene, glass, polypropylene, agarose, gelatin, hydrogel, a paramagnetic material, ceramic, plastic, glass, methylstyrene, acrylic polymer, titanium, latex, cellulose, nylon, silicone, and any combination thereof. In some embodiments, the synthetic particle comprises a hydrogel bead, a magnetic bead, or a combination thereof. In some embodiments, the synthetic particle is solid or semi-solid. In some embodiments, the synthetic particle is disruptable. In some embodiments, the synthetic particle comprises a bead.

In some embodiments, the synthetic particles are partitioned prior to the single cells. In some embodiments, the single cells are partitioned prior to the synthetic particles. In some embodiments, the method comprises lysing said single cells, thereby releasing nucleic acid target molecules from said cells. In some embodiments, stochastically labeling the cell indexing oligonucleotides comprises: i) contacting the plurality of stochastic labels with the cell indexing oligonucleotides to generate stochastic labels hybridized to the cell indexing oligonucleotides; and ii) extending the stochastic labels hybridized to the cell indexing oligonucleotides to generate the plurality of stochastically labeled cell indexing oligonucleotides. In some embodiments, stochastically labeling the nucleic acid target molecules comprises: i) contacting the plurality of stochastic labels with the nucleic acid target molecules to generate stochastic labels hybridized to the nucleic acid target molecules; and ii) extending the stochastic labels hybridized to the nucleic acid target molecules to generate the plurality of stochastically labeled cell nucleic acid target molecules. In some embodiments, extending the stochastic labels comprises extending the stochastic labels using a DNA polymerase and/or a reverse transcriptase.

In some embodiments, obtaining the sequencing data comprises sequencing at least a portion of the molecular label sequence, at least a portion of the cell indexing sequence, at least a portion of the cellular label, or any combination thereof. In some embodiments, the cell indexing oligonucleotide comprises a target sequence complementary to a capture sequence of a stochastic label configured to capture the sequence of the cell indexing oligonucleotide. In some embodiments, the plurality of nucleic acid target molecules comprise ribonucleic acids (RNAs), messenger RNAs (mRNAs), microRNAs, small interfering RNAs (siRNAs), RNA degradation products, RNAs each comprising a poly(A) tail, and any combination thereof. In some embodiments, obtaining the sequencing data comprises one or more of genome sequencing, exome sequencing, targeted DNA sequencing, targeted RNA sequencing, whole transcriptome RNA sequencing, ChIP-Seq, miRNA-seq, lincRNA-seq, methylation-seq, or any combination thereof. In some embodiments, the nucleic acid target molecules comprise binding reagent oligonucleotides associated with a cellular component-binding reagent capable of specifically binding to at least one cellular component target, and wherein the number of unique molecular label sequences associated with a unique identifier sequence of the antibody oligonucleotide in the sequencing data indicates the number of copies of the at least one cellular component target in the single cell. In some embodiments, the nucleic acid target molecules comprise sample indexing oligonucleotides, and wherein the sample indexing sequence of sample indexing oligonucleotide identifies the sample origin of the single cell.

In some embodiments, the plurality of single cells comprises more than 1000 cells. In some embodiments, the plurality of single cells comprises more than 10,000 cells. In some embodiments, the plurality of single cells comprise cells from a tissue or organ. In some embodiments, the plurality of single cells comprise cells from a thymus, white blood cells, red blood cells, liver cells, spleen cells, lung cells, heart cells, brain cells, skin cells, pancreas cells, stomach cells, cells from the oral cavity, cells from the nasal cavity, colon cells, small intestine cells, kidney cells, cells from a gland, brain cells, neural cells, glial cells, eye cells, reproductive organ cells, bladder cells, gamete cells, human cells, fetal cells, amniotic cells, or any combination thereof. In some embodiments, the plurality of single cells comprise plant cells, fungi cells, bacterial cells, prokaryotic cells, eukaryotic cells, unicellular cells, multi-cellular cells, immune cells, or any combination thereof. In some embodiments, the cells selected from the group consisting of T cells, B cells, monocytes, macrophages, neutrophils, dendritic cells, natural killer cells, fibroblasts, stromal cells, stem cells, progenitor cells, tumor cells, tumor stem cells, tumor infiltrating lymphocytes, and combinations thereof.

In some embodiments, the plurality of partitions comprises a plurality of droplets. In some embodiments, the plurality of partitions comprises microwells of a microwell array. In some embodiments, the micro-well array comprises at least 100 micro-wells, wherein each micro-well has a volume ranging from about 1,000 m$^3$ to about 786,000 µm$^3$. In some embodiments, the micro-well array comprises at least 10,000 micro-wells.

In some embodiments, the cellular label comprises the cell indexing sequence. In some embodiments, a portion of the cellular label comprises the cell indexing sequence. In some embodiments, the cellular label comprises all of the n cell indexing subsequences. In some embodiments, the cellular label comprises a portion of the cell indexing sequence. In some embodiments, the cellular label comprises one or more cell indexing subsequences of the n cell indexing subsequences of the cell indexing sequence. In some embodiments, the number of unique spatial indices is equal to or greater than the number of unique cellular label sequences. In some embodiments, generating the spatial index is performed prior to the partitioning of the cells. In some embodiments, generating the spatial index is performed after the partitioning of the cells. In some embodiments, generating the spatial index is performed by the user. In some embodiments, generating the spatial index is performed by the manufacturer.

In some embodiments, the cell indexing oligonucleotide is associated with a cell through a cellular component binding reagent. In some embodiments, the cell indexing oligonucleotide is configured to be detachable from the cellular component-binding reagent. In some embodiments, the method comprises dissociating the cell indexing oligonucleotide from the cellular component-binding reagent. In some embodiments, dissociating the cell indexing oligonucleotide comprises detaching the cell indexing oligonucleotide from the cellular component-binding reagent by UV photocleaving, chemical treatment, heating, enzyme treatment, or any combination thereof. In some embodiments, the dissociating occurs after stochastically labeling the cell indexing oligonucleotide. In some embodiments, the dissociating occurs before stochastically labeling the cell indexing oligonucleotide. In some embodiments, the sequence of the cell indexing oligonucleotide complementary to the capture sequence comprises a poly(dA) region.

In some embodiments, associating the agent exposure comprises identifying the one or more agents each single cell was exposed to and concentrations thereof. In some embodiments, conducting agent exposure comprises exposing two or more single cells to different agents. In some embodiments, conducting agent exposure comprises exposing two or more single cells to different concentrations of the same agent. In some embodiments, the method comprises inducing the release of an agent covalently attached to one or more inner surfaces of the micro-wells to initiate agent exposure. In some embodiments, a plurality of the micro-wells comprise an agent covalently attached to one or more inner surfaces of the micro-wells. In some embodiments, a plurality of the micro-wells comprise different amounts of the agent covalently attached to one or more inner surfaces of the micro-wells. In some embodiments, a plurality of the micro-wells comprise different agents covalently attached to one or more inner surfaces of the micro-wells. In some embodiments, the covalent attachment comprises the use of one or more cleavable linkers to enable release of the agent. In some embodiments, the one or more cleavable linkers comprise acid-labile linkers, base-labile linkers, photocleavable linkers, enzyme-cleavable linkers, or any combination thereof. In some embodiments, upon release, the agent contacts the single cell in the micro-well. In some embodiments, at least two the micro-wells of the array comprise different amounts of the same agent covalently attached to one or more inner surfaces of the micro-wells. In some embodiments, at least two the micro-wells of the array comprise different agents covalently attached to one or more inner surfaces of the micro-wells. In some embodiments, the concentration of the agent in the plurality of micro-wells is non-uniform.

In some embodiments, the agent comprises one or more components. In some embodiments, the agent comprises one or more of a chemical agent, a pharmaceutical, small molecule, a biologic, a CRISPR single-guide RNA (sgRNA), a small interfering RNA (siRNA), CRISPR RNA (crRNA), a small hairpin RNA (shRNA), a microRNA (miRNA), a piwi-interacting RNA (piRNA), an antisense oligonucleotide, a peptide or peptidomimetic inhibitor, an aptamer, an antibody, an intrabody, or any combination thereof. In some embodiments, the agent comprises one or more of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR component system or component thereof, DNA, RNA, artificial nucleic acids, a nanoparticle, an oligonucleotide aptamer, a peptide aptamer, or any combination thereof.

In some embodiments, the agent possesses at least one effector activity selected from the group consisting of: modulating a biological activity, binding a regulatory protein, modulating enzymatic activity, modulating substrate binding, modulating receptor activation, modulating protein stability/degradation, modulating transcript stability/degradation, and any combination thereof. In some embodiments, the agent comprises an infectious agent. In some embodiments, the agent comprises an anti-infectious agent. In some embodiments, the agent comprises a mixture of an infectious agent and an anti-infectious agent. In some embodiments, the infectious agent comprises a virus, a bacterium, a fungus, a protozoal parasite, or any combination thereof. In some embodiments, an anti-infectious agent comprises an anti-bacterial agent, an anti-fungal agent, an anti-parasitic agent, an anti-viral agent, or any combination thereof.

In some embodiments, the agent comprises a cytotoxic agent. In some embodiments, the cytotoxic agent is selected from the group consisting of a chemotherapeutic agent, a biologic agent, a toxin, a radioactive isotope, or any combination thereof. In some embodiments, the agent comprises a non-active component of a therapeutic. In some embodiments, the non-active component of a therapeutic comprises an excipient, carrier, diluent, vehicle, adjuvant, empty vector, or any combination thereof. In some embodiments, the agent comprises an expression vector, wherein the expression vector encodes one or more of the following: an mRNA, an antisense nucleic acid molecule, a RNAi molecule, a shRNA, a mature miRNA, a pre-miRNA, a pri-miRNA, an anti-miRNA, a ribozyme, any combination thereof.

In some embodiments, the single cells comprise a recombinant expression vector. In some embodiments, the recombinant expression vector comprises an inducible promoter, and wherein the expression of one or more of the following are under the control of said inducible promoter: an mRNA, an antisense nucleic acid molecule, a RNAi molecule, a shRNA, a mature miRNA, a pre-miRNA, a pri-miRNA, an anti-miRNA, a ribozyme, any combination thereof. In some embodiments, the agent is a dose-dependent inducer of the inducible promoter. In some embodiments, the dose-dependent inducer comprises tetracycline, pristinamycin, macrolide, ecdysone, mifepristone, or any combination thereof.

In some embodiments, the agent modulates the expression of one or more target biomarkers. In some embodiments, the agent modulates the activity of one or more target biomarkers. In some embodiments, the method comprises deriving an estimation of a concentration of the agent each cell was exposed to based on the determination of the partition of origin of each cell. In some embodiments, the method comprises correlation analysis of the estimated concentration of the agent each cell was exposed to and the RNA and/or DNA expression profiles of said cells. In some embodiments, the correlation analysis identifies one or more of the following: candidate therapeutic agents, candidate doses of candidate therapeutic agents, and cellular targets of candidate therapeutic agents. In some embodiments, one or more single cells of the plurality of single cells lack exposure to the one or more agents.

In some embodiments, obtaining phenotypic data for each single cell comprises imaging of each single cell. In some embodiments, imaging of each single cell yields imaging data. In some embodiments, imaging data comprises phenotypic data. In some embodiments, imaging comprises microscopy, time-lapse imaging microscopy, fluorescence microscopy, multi-photon microscopy, quantitative phase microscopy, surface enhanced Raman spectroscopy, videography, manual visual analysis, automated visual analysis, or any combination thereof. In some embodiments, the microscopy is confocal microscopy. In some embodiments, the microscopy is fluorescence microscopy. In some embodiments, the microscopy is quantitative microscopy. In some embodiments, imaging is performed at one or more time points. In some embodiments, the imaging occurs at sequential intervals for a period of time. In some embodiments, the period of time ranges from about 1 minute to about 24 hours. In some embodiments, the sequential intervals range from about 1 second to about 10 minutes. In some embodiments, imaging is performed before and/or after conducting agent exposure. In some embodiments, the phenotypic effects of the one or more agents are determined by imaging of the single cells. In some embodiments, the plurality of partitions are imaged sequentially. In some embodiments, the plurality of partitions are imaged simultaneously. In some embodiments, the plurality of partitions are imaged continuously.

In some embodiments, the plurality of single cells are derived from a tissue sample. In some embodiments, the plurality of single cells comprise a plurality of cell types. In some embodiments, the phenotypic data elucidates the identity of each cell type. In some embodiments, the single cells comprise a tagged endogenous protein. In some embodiments, the tagged endogenous protein is a fluorescent protein, a luminescent protein, a photoactivatable protein, a FLAG tag, a SNAP tag, a Halo tag, or any combination thereof. In some embodiments, the fluorescent protein is selected from the group comprising green fluorescent protein (GFP), blue fluorescent protein, cyan fluorescent protein, yellow fluorescent protein or red fluorescent protein. In some embodiments, phenotypic data comprises measurement of one or more of the localization, expression intensity, and persistence of expression of the tagged endogenous protein. In some embodiments, phenotypic data comprises measurement of cell death, and wherein the cell death is evaluated by detecting apoptosis markers. In some embodiments, one or more single cells are labeled with a reporter molecule.

In some embodiments, phenotypic data comprises measurement of a dynamic behavior of the single cells as a function of time. In some embodiments, the dynamic behavior comprises cellular activation, cellular inhibition, protein secretion, microvesicle secretion, exosome secretion, microparticle secretion, metabolite secretion, small molecule secretion, proton secretion, protein expression, or any combination thereof. In some embodiments, the phenotypic data comprises measurement of cellular activation, cellular inhibition, cellular interaction, protein expression, protein secretion, metabolite secretion, changes in lipid profiles, microvesicle secretion, exosome secretion, microparticle secretion, changes in cellular mass, cellular proliferation, changes in cellular morphology, motility, cell death, cell cytotoxicity, cell lysis, cell membrane polarization, establishment of a synapse, dynamic trafficking of proteins, granule polarization, calcium activation, metabolic changes, small molecule secretion, proton secretion, or any combination thereof.

In some embodiments, the phenotypic data comprises measurement of one or more cellular attributes. In some embodiments, the cellular attributes comprise physical attributes, morphological attributes, intracellular attributes, biochemical attributes, or any combination thereof. In some embodiments, physical attributes comprise cell size, volume, conductivity, low and high angle scatter, density, or any combination thereof. In some embodiments, morphological attributes comprise one or more of: cell shape, area, size, and lobularity; nucleus shape area, size, and lobularity; mitochondria shape, area, size, and lobularity; and ratio of nuclear volume to cell volume. In some embodiments, intracellular attributes comprise nucleus centroid/cell centroid distance, nucleus lobe centroid distance, distribution of proteins with the cells, distribution of organelles within the cells, or any combination thereof. In some embodiments, biochemical attributes comprise expression level of cellular proteins, cell surface proteins, cytoplasmic proteins, nuclear proteins, cellular nucleic acids, cell surface nucleic acids, cytoplasmic nucleic acids, nuclear nucleic acids, cellular carbohydrates, cell surface carbohydrates, cytoplasmic carbohydrates, nuclear carbohydrates, or any combination thereof. In some embodiments, the phenotypic data comprises measurement of one or more cellular features indicating cell proliferation, stress pathways, organelle function, cell cycle state, morphology, apoptosis, DNA damage, metabolism, signal transduction, cell differentiation, or any combination thereof.

In some embodiments, the cellular features indicating cell proliferation comprise nuclear count, cell count, total cell mass, total DNA, the phosphorylation state of cell cycle regulatory proteins, the post-translational modification state of any protein involved in cell growth or division, or any combination thereof. In some embodiments, the cellular features indicating stress pathway activation comprise transcription factor activation of NF-κB, AP1, ATF2, MSK1, CREB, or NFAT, and kinase activation of p38, JNK, ERK, RSK90, MEK, or any combination thereof. In some embodiments, the cellular features indicating organelle function comprise cytoskeletal organization, mitochondrial mass or membrane potential, peroxisome mass, golgi organization, plasma membrane permeability, or any combination thereof. In some embodiments, the cellular features indicating cell cycle state comprise DNA content, Histone H3 phosphorylation state, Rb phosporylation state, cyclin B1 (CDKI) biosynthesis, cyclin DI (CDK4, 6) biosynthesis, cyclin E (CDK2) biosynthesis, or any combination thereof. In some embodiments, the cellular features indicating apoptosis comprise nuclear size and shape, DNA content and degradation, caspase activation, phosphatidyl-expression, Bax translocation, or any combination thereof. In some embodiments, the cellular features indicating DNA damage comprise repair protein (APE) expression, tumor suppressor (p53, Rb) expression, oxidative activity (8-oxoguanine), transcription activity (Oct1), or any combination thereof. In some embodiments, the cellular features indicating metabolism comprise cAMP concentration, P-glycoprotein activity or CYP450 induction/inhibition, the concentration of an added substance, or any combination thereof. In some embodiments, the cellular features indicating signal transduction comprise Ca++ ion concentration, (pH) expression of a protein, activation of a protein, modification of a protein, translocation of a protein, interaction between proteins known to be associated with a specific pathway, or any combination thereof. In some embodiments, the cellular features indicating cell differentiation comprise expression of a tissue specific protein, exhibiting a tissue specific morphology, or any combination thereof.

Disclosed herein include probe compositions. In some embodiments, the probe compositions comprise n pluralities of probes, wherein n is an integer greater than 1, wherein the probes selectively anneal to the cell indexing subsequences of cell indexing oligonucleotides with complementary sequences, wherein each plurality of probes comprises m unique probes, wherein m is an integer greater than 1, wherein unique probes selectively anneal to different cell indexing subsequences, and wherein the probes comprise a detectable moiety, or precursor thereof.

Disclosed herein include probe compositions. In some embodiments, the probe compositions comprise n pluralities of probes, wherein n is an integer greater than 1, wherein the probes selectively anneal to the cell indexing subsequences of cell indexing oligonucleotides with complementary sequences, wherein each plurality of probes comprises p unique probes, wherein p is an integer greater than 1, wherein unique probes selectively anneal to different cell indexing subsequences, wherein m probes of the p unique probes comprise a detectable moiety, or precursor thereof, wherein m is an integer greater than 1, and wherein m is p−1.

Disclosed herein include cell indexing oligonucleotide compositions. In some embodiments, the cell indexing oligonucleotide compositions comprise a plurality of cell indexing oligonucleotides, wherein the plurality of cell indexing oligonucleotides comprises at least 2 unique cell indexing oligonucleotides, wherein a cell indexing oligonucleotide comprises a cell indexing sequence, wherein a cell indexing sequence comprises n cell indexing subsequences, wherein n is an integer greater than 1, wherein each nth cell indexing subsequence is selected from p unique cell indexing subsequences, wherein p is an integer greater than 1, wherein two unique cell indexing oligonucleotides comprise different cell indexing sequences. The cell indexing oligonucleotide compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include cell compositions. The cell compositions can comprise a cell, wherein one or more copies of a unique cell indexing oligonucleotide are associated with the cell, wherein the unique cell indexing oligonucleotide is selected from a plurality of cell indexing oligonucleotides comprising at least 100 unique cell indexing oligonucleotides, wherein the cell indexing oligonucleotide comprises a cell indexing sequence, wherein the cell indexing sequence comprises n cell indexing subsequences, wherein n is an integer greater than 1. The cell compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include cell compositions. The cell compositions can comprise a plurality of cells, wherein each single cell is associated with one or more unique cell indexing oligonucleotides, wherein the one or more unique cell indexing oligonucleotides associated with the same cell comprise the same cell indexing sequence, wherein the one or more unique cell indexing oligonucleotides associated with different cells comprise different cell indexing sequences, wherein the cell indexing sequence comprises n cell indexing subsequences, wherein n is an integer greater than 1. The cell compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

In some embodiments, one or more of the n cell indexing subsequences are separated by a linker sequence. In some embodiments, the cell indexing oligonucleotides comprises cell indexing subsequence$_1$-linker sequence$_1$-cell indexing subsequence$_2$-linker sequence$_2$- . . . cell indexing subsequence$_{n-1}$-linker sequence$_n$-cell indexing subsequence$_n$-target sequence. In some embodiments, the cell indexing oligonucleotide comprises a linker, and wherein a cellular component-binding reagent is associated with the cell indexing oligonucleotide via the linker. In some embodiments, the linker comprises a chemical group. In some embodiments, the chemical group is reversibly attached to the first indexing oligonucleotide. In some embodiments, the cellular component-binding reagent comprises a chemical group. In some embodiments, the chemical group comprises a UV photocleavable group, a streptavidin, a biotin, an amine, a disulfide linkage, or any combination thereof.

In some embodiments, the linker comprises a 5' amine. In some embodiments, the linker comprises a carbon chain. In some embodiments, the carbon chain comprises 2-30 carbons. In some embodiments, the cell indexing oligonucleotide is covalently attached to the cellular component-binding reagent. In some embodiments, the cell indexing oligonucleotide is conjugated to the cellular component-binding reagent. In some embodiments, the cell indexing oligonucleotide is conjugated to the cellular component-binding reagent through a chemical group selected from the group consisting of a UV photocleavable group, a streptavidin, a biotin, an amine, and a combination thereof. In some embodiments, the cell indexing oligonucleotide is non-covalently attached to the cellular component-binding reagent. In some embodiments, the cell indexing oligonucleotide is configured to be detachable from the cellular component-binding reagent. In some embodiments, the cell indexing oligonucleotide is associated with a cell via the cellular component binding reagent. In some embodiments, each cell is partitioned to a plurality of partitions, and wherein a partition comprises a single cell. In some embodiments, the plurality of partitions comprises microwells of a microwell array.

Disclosed herein include synthetic particle compositions. The composition can comprise a synthetic particle, wherein the synthetic particle can comprise a plurality of stochastic labels, wherein the stochastic labels comprise a cell indexing sequence, wherein the cell indexing sequence is selected from a plurality of cell indexing sequences comprising at least 100 unique cell indexing sequences, wherein the cell indexing sequence comprises n cell indexing subsequences, wherein n is an integer greater than 1. The synthetic particle composition can comprise n pluralities of probes, wherein probes can selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include synthetic particle compositions. The composition can comprise a plurality of synthetic particles. The plurality of synthetic particle can comprise a plurality of stochastic labels, wherein the stochastic labels comprise a cell indexing sequence, wherein the stochastic labels associated with the same synthetic particle comprise the same cell indexing sequence, wherein the stochastic labels associated with different synthetic particles comprise different cell indexing sequences, wherein the cell indexing sequence comprises n cell indexing subsequences, wherein n is an integer greater than 1. The synthetic particle composition can comprise n pluralities of probes, wherein probes can selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include micro-well array compositions. A micro-well array can comprise at least 100 micro-wells, wherein each micro-well has a volume ranging from about 1,000 $\mu m^3$ to about 786,000 $\mu m^3$, wherein a plurality of the micro-wells comprise a single synthetic particle from a plurality of synthetic particles, wherein each synthetic particle comprises a plurality of stochastic labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, wherein the cell indexing sequence comprises n cell indexing subsequences, wherein n is an integer greater than 1. The micro-well array compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include cartridge compositions. A cartridge can comprise at least one of: an inlet port, an outlet port, a pump, a valve, a vent, a reservoir, a sample collection chamber, a temperature control apparatus, or any combination thereof, wherein the cartridge comprises a micro-well array, wherein the micro-well array comprises at least 100 micro-wells, wherein each micro-well has a volume ranging from about 1,000 m³ to about 786,000 µm³, wherein a plurality of the micro-wells comprise a single synthetic particle from a plurality of synthetic particles, wherein each synthetic particle comprises a plurality of stochastic labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, wherein the cell indexing sequence comprises n cell indexing subsequences, wherein n is an integer greater than 1. The cartridge composition can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

In some embodiments, the stochastic labels comprise a cellular label, wherein stochastic labels associated with the same synthetic particle comprise the same cellular label, and wherein stochastic labels associated with different synthetic particles comprise different cellular labels. In some embodiments, the cellular label comprises the cell indexing sequence. In some embodiments, a portion of the cellular label comprises the cell indexing sequence. In some embodiments, the cellular label comprises all of the n cell indexing subsequences. In some embodiments, the cellular label comprises a portion of the cell indexing sequence. In some embodiments, the cellular label comprises one or more cell indexing subsequences of the n cell indexing subsequences of the cell indexing sequence. In some embodiments, each nth cell indexing subsequence is selected from p unique cell indexing subsequences, wherein p is an integer greater than 1.

In some embodiments, the cell indexing sequence is associated with a spatial index. In some embodiments, determining the spatial index comprises sequentially hybridizing and imaging n pluralities of probes annealing to the n cell indexing subsequences for n cycles. In some embodiments, the n pluralities of probes comprise one or more detectable moieties, wherein imaging comprises detecting the one or more detectable moieties. In some embodiments, the detectable moieties of the probes comprise fluorescent labels, wherein sequential hybridization and imaging comprises sequential hybridization and fluorescent imaging. In some embodiments, the spatial index comprises a series of n signals and/or absence of signals detected in the n cycles. In some embodiments, p is an integer from 2 to 15. In some embodiments, n is an integer from 2 to 15. In some embodiments, the plurality of cell indexing sequences comprises at least 1,000 unique cell indexing sequences. In some embodiments, the plurality of cell indexing sequences comprises at least 10,000 unique cell indexing sequences. In some embodiments, the plurality of cell indexing sequences comprises at least 100,000 unique cell indexing sequences.

In some embodiments, each synthetic particle has been partitioned to a plurality of partitions, wherein a partition comprises a single synthetic particle, and wherein the spatial index of the unique cell indexing sequence associated with each synthetic particle has been elucidated by generating the spatial index. In some embodiments, said generating the spatial index was performed in the plurality of partitions. In some embodiments, the composition comprises a spatial index lookup table. In some embodiments, the spatial index lookup table identifies the cell indexing sequence associated with each synthetic particle in the plurality of partitions. In some embodiments, association of the cellular label and the cell indexing sequence during sequencing identifies the micro-well of origin of each sequenced nucleic acid target molecule. In some embodiments, the cellular label comprises the cell indexing sequence, and wherein the sequencing of the cellular label identifies the micro-well of origin of each sequenced nucleic acid target molecule. In some embodiments, the composition comprises a buffer. In some embodiments, the composition comprises a cartridge. In some embodiments, the composition comprises one or more reagents for a reverse transcription reaction. In some embodiments, the composition comprises one or more reagents for an amplification reaction.

BRIEF DESCRIPTION OF THE DRAWINGS

FIG. 6 shows non-limiting schematic illustration of a method of labeling a plurality of cells with cell indexing oligonucleotides by a combinatorial split-pool synthesis approach.

FIGS. 10A-10D show non-limiting exemplary designs of oligonucleotides for determining protein expression and gene expression simultaneously and for sample indexing.

DETAILED DESCRIPTION

Figure 1:
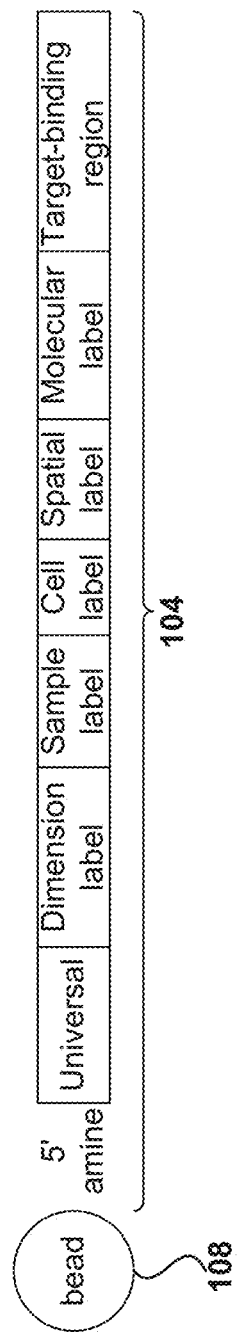
FIG. 1 illustrates a non-limiting exemplary stochastic barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding such as the Precise™ assay (Cellular Research, Inc. (Palo Alto, CA)) can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular labels on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular labels, and the numbers of mRNA molecules.

Methods for determining mRNA expression profiles of single cells can be performed in a massively parallel manner. For example, the Precise™ assay can be used to determine the mRNA expression profiles of more than 10000 cells simultaneously. The number of single cells (e.g., 100s or 1000s of singles) for analysis per sample can be lower than the capacity of the current single cell technology. Pooling of cells from different samples enables improved utilization of the capacity of the current single technology, thus lowering reagents wasted and the cost of single cell analysis.

Disclosed herein include methods for labeling a plurality of cells with cell indexing oligonucleotides. In some embodiments, the method comprises: (a) associating cells in each first partition of a plurality of first partitions with a cellular component-binding reagent of a plurality of cellular component-binding reagents, wherein each of the cells comprises one or more cellular component targets, wherein the cellular component-binding reagent is associated with a first indexing oligonucleotide with a first cell indexing subsequence, wherein two cellular component-binding reagents of the plurality of cellular component-binding reagents are associated with first indexing oligonucleotides with different first cell indexing subsequences, and wherein the cellular component-binding reagent is capable of specifically binding to the one or more cellular component targets, thereby generating cells associated with the first cell indexing subsequence, in each first partition of the plurality of first partitions, via the cellular component-binding reagent the first indexing oligonucleotide with the first cell indexing subsequence is associated with, wherein the cells in two first partitions of the plurality of first partitions are associated with different first cell indexing subsequences. The method can comprise (b) pooling the cells associated with the cellular component-binding reagents in each first partition of the plurality of first partitions. The method can comprise (c) distributing the pooled cells into a plurality of second partitions. The method can comprise (d) associating the pooled cells in each second partition of the plurality of second partitions with a second indexing oligonucleotide of a plurality of second indexing oligonucleotides with a second cell indexing subsequence, wherein the second indexing oligonucleotides of the plurality of second indexing oligonucleotides in two second partitions of the plurality of second partitions comprise different second cell indexing subsequences, thereby generating cells associated with the second cell indexing subsequence, in each second partition of the plurality of second partitions, wherein the cells in two second partitions of the plurality of second partitions are associated with different second cell indexing subsequences. The method can comprise (e) generating cells associated with the cellular component-binding reagent in each second partition of the plurality of second partitions associated with a cell indexing oligonucleotide, wherein the cell indexing sequence of the cell indexing oligonucleotide comprises the first cell indexing subsequence and the second cell indexing subsequence of the second cell indexing oligonucleotide associated with the second partition of the plurality of second partitions, via the cellular component-binding reagent associated with the first indexing oligonucleotide with the first cell indexing subsequence associated with each of the cells in the second partition.

Disclosed herein include methods for generating a spatial index. In some embodiments, the method comprises: (a) contacting a cell indexing oligonucleotide with a plurality of first probes, wherein one or more of the probes of the plurality of first probes comprise a detectable moiety, or precursor thereof, wherein the cell indexing oligonucleotide comprises a series of n cell indexing subsequences, wherein n is an integer greater than 1, and wherein probes selectively anneal to cell indexing subsequences with complementary sequences; (b) removing unannealed probes; (c) imaging the cell indexing oligonucleotide, wherein imaging comprises detecting a signal of the detectable moiety; (d) removing the annealed probes and/or the detectable moieties thereof; and (e) repeating the steps (a)-(d) for a total of n cycles, wherein each nth cycle comprises contacting a plurality of nth probes with the cell indexing oligonucleotide, whereby a spatial index is generated for the cell indexing oligonucleotide, wherein the spatial index comprises a series of n signals and/or absence of signals detected in the n cycles.

Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (c) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (d) determining the spatial location of each nucleic acid target molecule by associating the cellular label of the partition and the cell indexing sequence of the partition, wherein the spatial location comprises the identity of the partition from which the nucleic acid target molecule originated.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) obtaining phenotypic data for each single cell; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the phenotypic data and the sequencing data of each single cell by associating the cellular label of the partition and the cell indexing sequence for each nucleic acid target molecule.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the agent exposure and the sequencing data of each single cell by associating the cellular label of the partition and the cell indexing sequence for each nucleic acid target molecule.

Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) stochastically labeling the nucleic acid target molecules using the plurality of stochastic labels to generate a plurality of stochastically labeled nucleic acid target molecules; (c) obtaining the sequencing data of the plurality of stochastically labeled nucleic acid target molecules, wherein obtaining the sequencing data comprises sequencing at least a portion of the cell indexing sequence; and (d) determining the spatial location of each nucleic acid target based on the cell indexing sequence, wherein the spatial location comprises the identity of the partition from which the nucleic acid target molecule originated.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) obtaining phenotypic data for each single cell; (c) stochastically labeling the nucleic acid target molecules using the plurality of stochastic labels to generate a plurality of stochastically labeled nucleic acid target molecules; (d) obtaining the sequencing data of the plurality of stochastically labeled nucleic acid target molecules, wherein obtaining the sequencing data comprises sequencing at least a portion of the cell indexing sequence; and (e) associating the phenotypic data and the sequencing data of each single cell based on the cell indexing sequence.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the nucleic acid target molecules using the plurality of stochastic labels to generate a plurality of stochastically labeled nucleic acid target molecules; (d) obtaining the sequencing data of the plurality of stochastically labeled nucleic acid target molecules, wherein obtaining the sequencing data comprises sequencing at least a portion of the cell indexing sequence; and (e) associating the agent exposure and the sequencing data of each single cell based on the cell indexing sequence.

Disclosed herein include probe compositions. In some embodiments, the probe compositions comprise n pluralities of probes, wherein n is an integer greater than 1, wherein the probes selectively anneal to the cell indexing subsequences of cell indexing oligonucleotides with complementary sequences, wherein each plurality of probes comprises m unique probes, wherein m is an integer greater than 1, wherein unique probes selectively anneal to different cell indexing subsequences, and wherein the probes comprise a detectable moiety, or precursor thereof.

Disclosed herein include probe compositions. In some embodiments, the probe compositions comprise n pluralities of probes, wherein n is an integer greater than 1, wherein the probes selectively anneal to the cell indexing subsequences of cell indexing oligonucleotides with complementary sequences, wherein each plurality of probes comprises p unique probes, wherein p is an integer greater than 1, wherein unique probes selectively anneal to different cell indexing subsequences, wherein m probes of the p unique probes comprise a detectable moiety, or precursor thereof, wherein m is an integer greater than 1, and wherein m is p−1.

Disclosed herein include cell indexing oligonucleotide compositions. In some embodiments, the cell indexing oligonucleotide compositions comprise a plurality of cell indexing oligonucleotides, wherein the plurality of cell indexing oligonucleotides comprises at least 2 unique cell indexing oligonucleotides, wherein a cell indexing oligonucleotide comprises a cell indexing sequence, wherein a cell indexing sequence comprises n cell indexing subsequences, wherein n is an integer greater than 1, wherein each nth cell indexing subsequence is selected from p unique cell indexing subsequences, wherein p is an integer greater than 1, wherein two unique cell indexing oligonucleotides comprise different cell indexing sequences. The cell indexing oligonucleotide compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include cell compositions. The cell compositions can comprise a cell, wherein one or more copies of a unique cell indexing oligonucleotide are associated with the cell, wherein the unique cell indexing oligonucleotide is selected from a plurality of cell indexing oligonucleotides comprising at least 100 unique cell indexing oligonucleotides, wherein the cell indexing oligonucleotide comprises a cell indexing sequence, wherein the cell indexing sequence comprises n cell indexing subsequences, wherein n is an integer greater than 1. The cell compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include cell compositions. The cell compositions can comprise a plurality of cells, wherein each single cell is associated with one or more unique cell indexing oligonucleotides, wherein the one or more unique cell indexing oligonucleotides associated with the same cell comprise the same cell indexing sequence, wherein the one or more unique cell indexing oligonucleotides associated with different cells comprise different cell indexing sequences, wherein the cell indexing sequence comprises n cell indexing subsequences, wherein n is an integer greater than 1. The cell compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include synthetic particle compositions. The composition can comprise a synthetic particle, wherein the synthetic particle can comprise a plurality of stochastic labels, wherein the stochastic labels comprise a cell indexing sequence, wherein the cell indexing sequence is selected from a plurality of cell indexing sequences comprising at least 100 unique cell indexing sequences, wherein the cell indexing sequence comprises n cell indexing subsequences, wherein n is an integer greater than 1. The synthetic particle composition can comprise n pluralities of probes, wherein probes can selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include synthetic particle compositions. The composition can comprise a plurality of synthetic particles. The plurality of synthetic particle can comprise a plurality of stochastic labels, wherein the stochastic labels comprise a cell indexing sequence, wherein the stochastic labels associated with the same synthetic particle comprise the same cell indexing sequence, wherein the stochastic labels associated with different synthetic particles comprise different cell indexing sequences, wherein the cell indexing sequence comprises n cell indexing subsequences, wherein n is an integer greater than 1. The synthetic particle composition can comprise n pluralities of probes, wherein probes can selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include micro-well array compositions. A micro-well array can comprise at least 100 micro-wells, wherein each micro-well has a volume ranging from about 1,000 $\mu m^3$ to about 786,000 $\mu m^3$, wherein a plurality of the micro-wells comprise a single synthetic particle from a plurality of synthetic particles, wherein each synthetic particle comprises a plurality of stochastic labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, wherein the cell indexing sequence comprises n cell indexing subsequences, wherein n is an integer greater than 1. The micro-well array compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Disclosed herein include cartridge compositions. A cartridge can comprise at least one of: an inlet port, an outlet port, a pump, a valve, a vent, a reservoir, a sample collection chamber, a temperature control apparatus, or any combination thereof, wherein the cartridge comprises a micro-well array, wherein the micro-well array comprises at least 100 micro-wells, wherein each micro-well has a volume ranging from about 1,000 $m^3$ to about 786,000 $\mu m^3$, wherein a plurality of the micro-wells comprise a single synthetic particle from a plurality of synthetic particles, wherein each synthetic particle comprises a plurality of stochastic labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, wherein the cell indexing sequence comprises n cell indexing subsequences, wherein n is an integer greater than 1. The cartridge composition can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein, an antibody can be a full-length (e.g., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

In some embodiments, an antibody is a functional antibody fragment. For example, an antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (for example, CD8, CD34, and CD45), and therapeutic antibodies.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2': 4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* LI.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Barcodes

Barcoding, such as stochastic barcoding, has been described in, for example, Fu et al., *Proc Natl Acad Sci U.S.A.*, 2011 May 31, 108(22):9026-31; U.S. Patent Application Publication No. US2011/0160078; Fan et al., *Science*, 2015 Feb. 6, 347(6222):1258367; US Patent Application Publication No. US2015/0299784; and PCT Application Publication No. WO2015/031691; the content of each of these, including any supporting or supplemental information or material, is incorporated herein by reference in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5'amine that may link the barcode to a solid support 108. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., A well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For stochastic barcoding using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
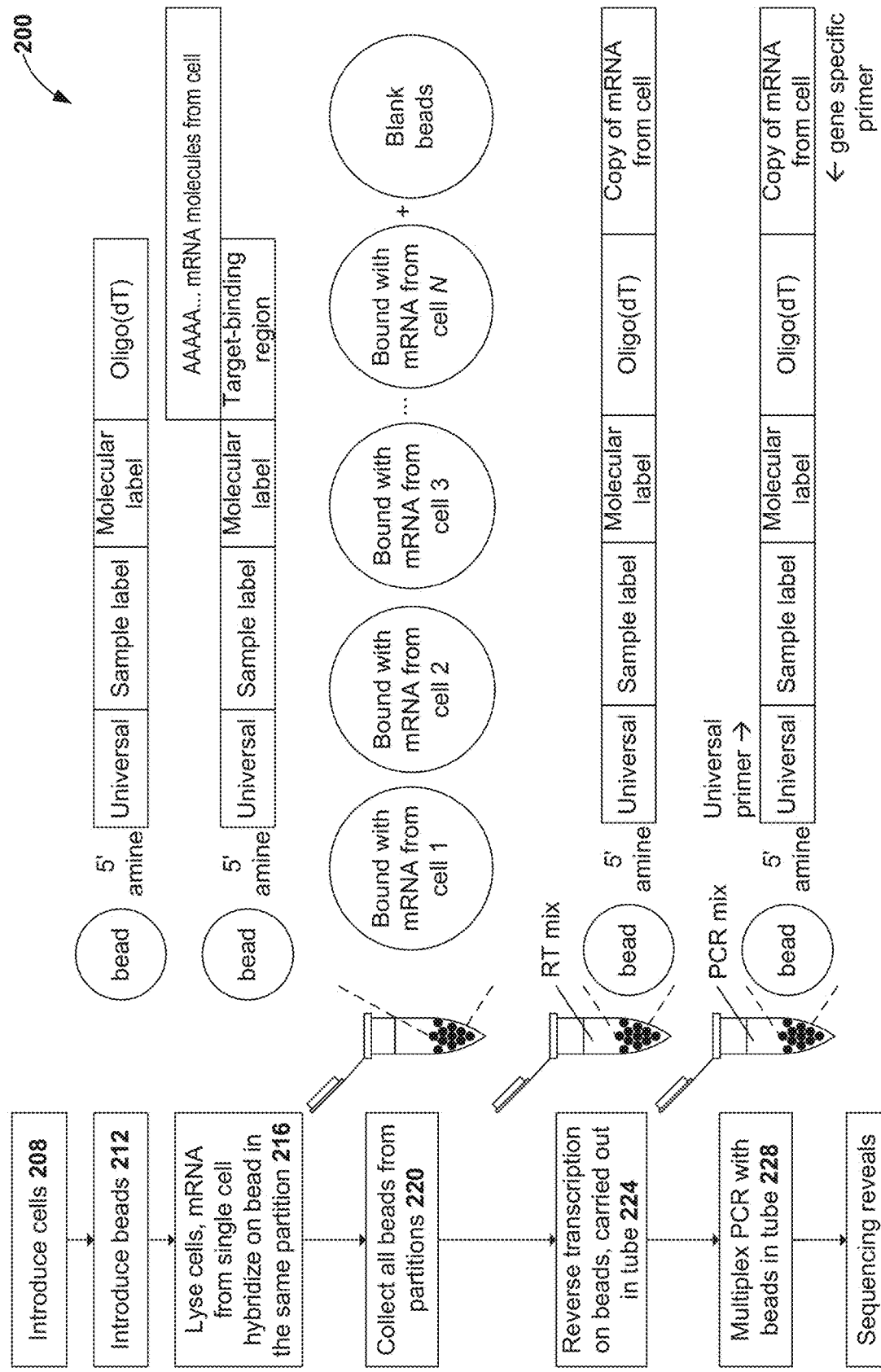
FIG. 2 shows a non-limiting exemplary workflow of stochastic barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometers. In some embodiments, the diameter of the bead can be, or be about, 0.1, 0.5, 1, 2, 3, 4, 5, 6, 7, 8, 9, 10, 20, 30, 40, 50 micrometers, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
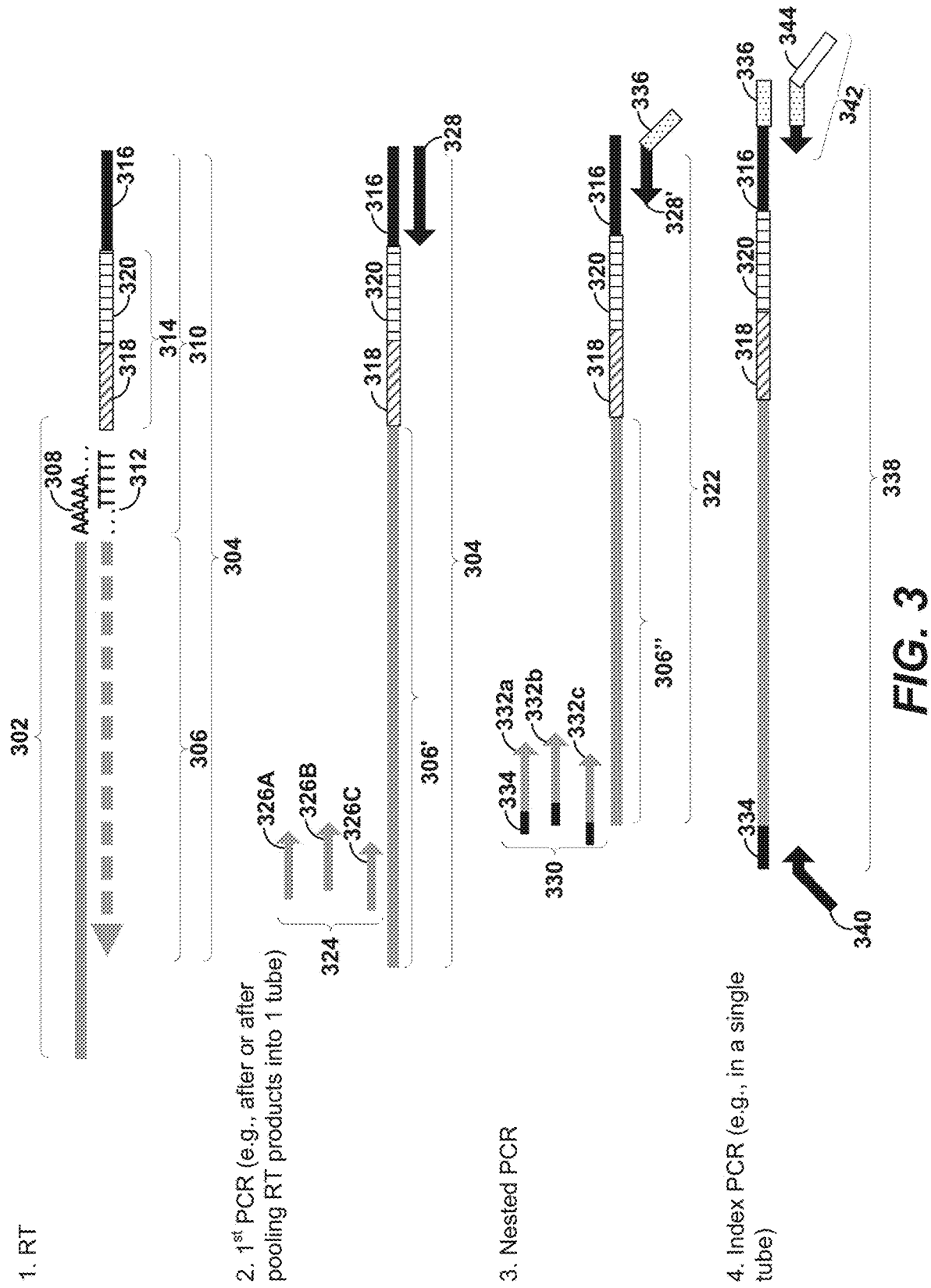
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label, a cell label, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label can include 3 to 20 nucleotides. In some embodiments, the molecular label can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306'' of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Compositions Comprising Cellular Component Binding Reagents Associated with Oligonucleotides Some embodiments disclosed herein provide a plurality of compositions each comprising a cellular component binding reagent (such as a protein binding reagent) that is conjugated with an oligonucleotide, wherein the oligonucleotide comprises a unique identifier for the cellular component binding reagent that it is conjugated with. Cellular component binding reagents (such as barcoded antibodies) and their uses (such as sample indexing of cells) have been described in U.S. Patent Application Publication No. US2018/0088112 and U.S. Patent Application Publication No. US2018/0346970; the content of each of these is incorporated herein by reference in its entirety.

In some embodiments, the cellular component binding reagent is capable of specifically binding to a cellular component target. For example, a binding target of the cellular component binding reagent can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component binding reagent (e.g., a protein binding reagent) is capable of specifically binding to an antigen target or a protein target. In some embodiments, each of the oligonucleotides can comprise a barcode, such as a stochastic barcode. A barcode can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., unanchored to a solid support or anchored to a solid support. The poly(A) tail can be from about 10 to 50 nucleotides in length. In some embodiments, the poly(A) tail can be 18 nucleotides in length. The oligonucleotides can comprise deoxyribonucleotides, ribonucleotides, or both.

The unique identifiers can be, for example, a nucleotide sequence having any suitable length, for example, from about 4 nucleotides to about 200 nucleotides. In some embodiments, the unique identifier is a nucleotide sequence of 25 nucleotides to about 45 nucleotides in length. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides. In some embodiments, the sequences of the set of unique identifiers are different from each other, or the complement thereof, by at least 3%, at least 5%, at least 8%, at least 10%, at least 15%, at least 20%, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as protein binding reagents, antibodies or fragments thereof, aptamers, small molecules, ligands, peptides, oligonucleotides, etc., or any combination thereof. In some embodiments, the cellular component binding reagents can be polyclonal antibodies, monoclonal antibodies, recombinant antibodies, single chain antibody (sc-Ab), or fragments thereof, such as Fab, Fv, etc. In some embodiments, the plurality of cellular component binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different cellular component reagents. In some embodiments, the plurality of cellular component binding reagents can comprise at least, or comprise at most, 20, 30, 40, 50, 60, 70, 80, 90, 100, 200, 300, 400, 500, 600, 700, 800, 900, 1000, 2000, or 5000, different cellular component reagents.

The oligonucleotide can be conjugated with the cellular component binding reagent through various mechanism. In some embodiments, the oligonucleotide can be conjugated with the cellular component binding reagent covalently. In some embodiment, the oligonucleotide can be conjugated with the cellular component binding reagent non-covalently. In some embodiments, the oligonucleotide is conjugated with the cellular component binding reagent through a linker. The linker can be, for example, cleavable or detachable from the cellular component binding reagent and/or the oligonucleotide. In some embodiments, the linker can comprise a chemical group that reversibly attaches the oligonucleotide to the cellular component binding reagents. The chemical group can be conjugated to the linker, for example, through an amine group. In some embodiments, the linker can comprise a chemical group that forms a stable bond with another chemical group conjugated to the cellular component binding reagent. For example, the chemical group can be a UV photocleavable group, a disulfide bond, a streptavidin, a biotin, an amine, etc. In some embodiments, the chemical group can be conjugated to the cellular component binding reagent through a primary amine on an amino acid, such as lysine, or the N-terminus. Commercially available conjugation kits, such as the Protein-Oligo Conjugation Kit (Solulink, Inc., San Diego, CA), the Thunder-Link® oligo conjugation system (Innova Biosciences, Cambridge, United Kingdom), etc., can be used to conjugate the oligonucleotide to the cellular component binding reagent.

The oligonucleotide can be conjugated to any suitable site of the cellular component binding reagent (e.g., a protein binding reagent), as long as it does not interfere with the specific binding between the cellular component binding reagent and its cellular component target. In some embodiments, the cellular component binding reagent is a protein, such as an antibody. In some embodiments, the cellular component binding reagent is not an antibody. In some embodiments, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. Methods of conjugating oligonucleotides to cellular component binding reagents (e.g., antibodies) have been previously disclosed, for example, in U.S. Pat. No. 6,531,283, the content of which is hereby expressly incorporated by reference in its entirety. Stoichiometry of oligonucleotide to cellular component binding reagent can be varied. To increase the sensitivity of detecting the cellular component binding reagent specific oligonucleotide in sequencing, it may be advantageous to increase the ratio of oligonucleotide to cellular component binding reagent during conjugation. In some embodiments, each cellular component binding reagent can be conjugated with a single oligonucleotide molecule. In some embodiments, each cellular component binding reagent can be conjugated with more than one oligonucleotide molecule, for example, at least, or at most, 2, 3, 4, 5, 10, 20, 30, 40, 50, 100, 1000, or a number or a range between any two of these values, oligonucleotide molecules wherein each of the oligonucleotide molecule comprises the same, or different, unique identifiers. In some embodiments, each cellular component binding reagent can be conjugated with more than one oligonucleotide molecule, for example, at least, or at most, 2, 3, 4, 5, 10, 20, 30, 40, 50, 100, 1000, oligonucleotide molecules, wherein each of the oligonucleotide molecule comprises the same, or different, unique identifiers.

In some embodiments, the plurality of cellular component binding reagents are capable of specifically binding to a plurality of cellular component targets in a sample, such as a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components (e.g., proteins) in a cell or an organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components (e.g., proteins) in a cell or an organism. In some embodiments, the plurality of cellular component targets can comprise, or comprise about, 2, 3, 4, 5, 10, 20, 30, 40, 50, 100, 1000, 10000, or a number or a range between any tow of these values, different cellular component targets. In some embodiments, the plurality of cellular component targets can comprise at least, or comprise at most, 2, 3, 4, 5, 10, 20, 30, 40, 50, 100, 1000, 10000, different cellular component targets.

There are provided, in some embodiments, a cellular component binding reagent (e.g., an antibody) that is associated (e.g., conjugated) with an oligonucleotide comprising a unique identifier sequence for the antibody. An oligonucleotide-conjugated with a cellular component binding reagent, an oligonucleotide for conjugation with a cellular component binding reagent, or an oligonucleotide previously conjugated with a cellular component binding reagent can be referred to herein as an antibody oligonucleotide (abbreviated as a binding reagent oligonucleotide). An oligonucleotide-conjugated with an antibody, an oligonucleotide for conjugation with an antibody, or an oligonucleotide previously conjugated with an antibody can be referred to herein as an antibody oligonucleotide (abbreviated as an "AbOligo" or "AbO"). The oligonucleotide can also comprise additional components, including but not limited to, one or more linker, one or more unique identifier for the antibody, optionally one or more barcode sequences (e.g., molecular labels), and a poly(A) tail. In some embodiments, the oligonucleotide can comprise, from 5' to 3', a linker, a unique identifier, a barcode sequence (e.g., a molecular label), and a poly(A) tail. An antibody oligonucleotide can be an mRNA mimic.

Figure 4:
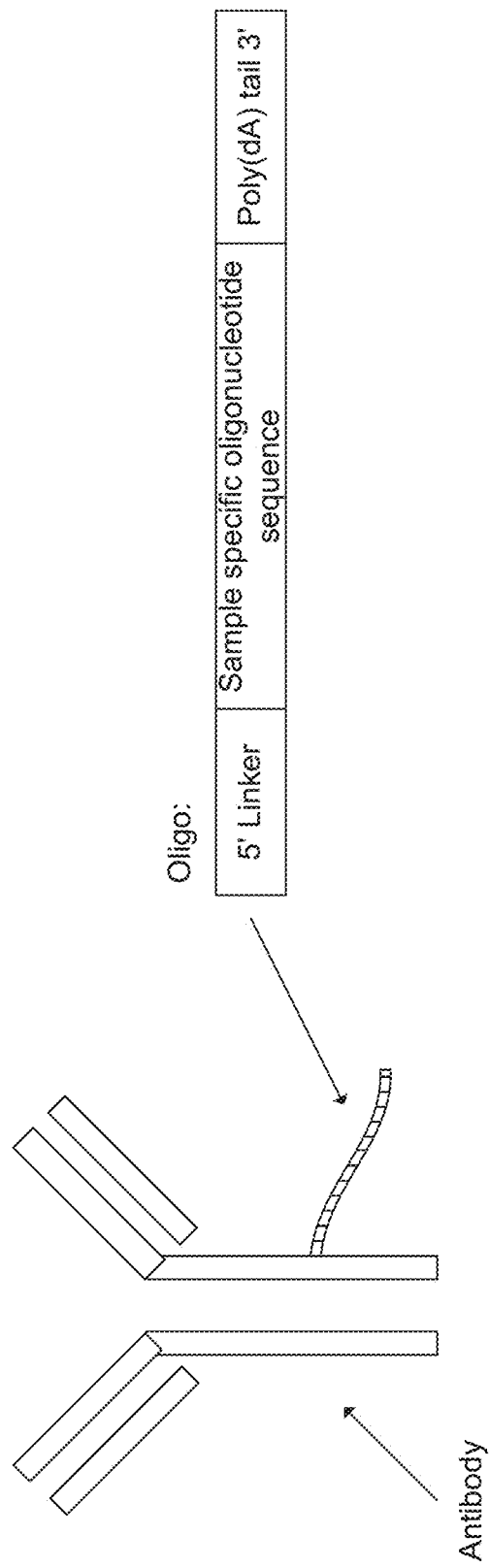
FIG. 4 shows a schematic illustration of an exemplary binding reagent (antibody illustrated here) associated with an oligonucleotide comprising a unique identifier for sample indexing to determine cells from the same or different samples.

FIG. 4 shows a schematic illustration of an exemplary cellular component binding reagent (e.g., an antibody) that is associated (e.g., conjugated) with an oligonucleotide comprising a unique identifier sequence for the antibody. The cellular component binding reagent can be capable of specifically binding to at least one cellular component target, such as an antigen target or a protein target. A binding reagent oligonucleotide (e.g., a sample indexing oligonucleotide, or an antibody oligonucleotide) can comprise a sequence (e.g., a sample indexing sequence) for performing the methods of the disclosure. For example, a sample indexing oligonucleotide can comprise a sample indexing sequence for identifying sample origin of one or more cells of a sample. Indexing sequences (e.g., sample indexing sequences) of at least two compositions comprising two cellular component binding reagents (e.g., sample indexing compositions) of the plurality of compositions comprising cellular component binding reagents can comprise different sequences. In some embodiments, the binding reagent oligonucleotide is not homologous to genomic sequences of a species. The binding reagent oligonucleotide can be configured to be (or can be) detachable or non-detachable from the cellular component binding reagent.

The oligonucleotide conjugated to a cellular component binding reagent can, for example, comprise a barcode sequence (e.g., a molecular label sequence), a poly(A) tail, or a combination thereof. An oligonucleotide conjugated to a cellular component binding reagent can be an mRNA mimic. In some embodiments, the sample indexing oligonucleotide comprises a sequence complementary to a capture sequence of at least one barcode of the plurality of barcodes. A target binding region of the barcode can comprise the capture sequence. The target binding region can, for example, comprise a poly(dT) region. In some embodiments, the sequence of the sample indexing oligonucleotide complementary to the capture sequence of the barcode can comprise a poly(A) tail. The sample indexing oligonucleotide can comprise a molecular label.

In some embodiments, the binding reagent oligonucleotide (e.g., the sample oligonucleotide) comprises a nucleotide sequence of, or a nucleotide sequence of about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the binding reagent oligonucleotide comprises a nucleotide sequence of at least, or of at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

In some embodiments, the cellular component binding reagent comprises an antibody, a tetramer, an aptamers, a protein scaffold, or a combination thereof. The binding reagent oligonucleotide can be conjugated to the cellular component binding reagent, for example, through a linker. The binding reagent oligonucleotide can comprise the linker. The linker can comprise a chemical group. The chemical group can be reversibly, or irreversibly, attached to the molecule of the cellular component binding reagent. The chemical group can be selected from the group consisting of a UV photocleavable group, a disulfide bond, a streptavidin, a biotin, an amine, and any combination thereof.

In some embodiments, the cellular component binding reagent can bind to ADAM10, CD156c, ANO6, ATP1B2, ATP1B3, BSG, CD147, CD109, CD230, CD29, CD298, ATP1B3, CD44, CD45, CD47, CD51, CD59, CD63, CD97, CD98, SLC3A2, CLDND1, HLA-ABC, ICAM1, ITFG3, MPZL1, NA K ATPase alpha1, ATP1A1, NPTN, PMCA ATPase, ATP2B1, SLC1A5, SLC29A1, SLC2A1, SLC44A2, or any combination thereof.

In some embodiments, the protein target is, or comprises, an extracellular protein, an intracellular protein, or any combination thereof. In some embodiments, the antigen or protein target is, or comprises, a cell-surface protein, a cell marker, a B-cell receptor, a T-cell receptor, a major histocompatibility complex, a tumor antigen, a receptor, an integrin, or any combination thereof. The antigen or protein target can be, or comprise, a lipid, a carbohydrate, or any combination thereof. The protein target can be selected from a group comprising a number of protein targets. The number of antigen target or protein targets can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. The number of protein targets can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

The cellular component binding reagent (e.g., a protein binding reagent) can be associated with two or more binding reagent oligonucleotide (e.g., sample indexing oligonucleotides) with an identical sequence. The cellular component binding reagent can be associated with two or more binding reagent oligonucleotides with different sequences. The number of binding reagent oligonucleotides associated with the cellular component binding reagent can be different in different implementations. In some embodiments, the number of binding reagent oligonucleotides, whether having an identical sequence, or different sequences, can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of binding reagent oligonucleotides can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

The plurality of compositions comprising cellular component binding reagents (e.g., the plurality of sample indexing compositions) can comprise one or more additional cellular component binding reagents not conjugated with the binding reagent oligonucleotide (such as sample indexing oligonucleotide), which is also referred to herein as the binding reagent oligonucleotide-free cellular component binding reagent (such as sample indexing oligonucleotide-free cellular component binding reagent). The number of additional cellular component binding reagents in the plurality of compositions can be different in different implementations. In some embodiments, the number of additional cellular component binding reagents can be, or be about, 1, 2, 3, 4, 5, 6, 7, 8, 9, 10, 20, 30, 40, 50, 60, 70, 80, 90, 100, or a number or a range between any two of these values. In some embodiments, the number of additional cellular component binding reagents can be at least, or be at most, 1, 2, 3, 4, 5, 6, 7, 8, 9, 10, 20, 30, 40, 50, 60, 70, 80, 90, or 100. The cellular component binding reagent and any of the additional cellular component binding reagents can be identical, in some embodiments.

In some embodiments, a mixture comprising cellular component binding reagent(s) that is conjugated with one or more binding reagent oligonucleotides (e.g., sample indexing oligonucleotides) and cellular component binding reagent(s) that is not conjugated with binding reagent oligonucleotides is provided. The mixture can be used in some embodiments of the methods disclosed herein, for example, to contact the sample(s) and/or cell(s). The ratio of (1) the number of a cellular component binding reagent conjugated with a binding reagent oligonucleotide and (2) the number of another cellular component binding reagent (e.g., the same cellular component binding reagent) not conjugated with the binding reagent oligonucleotide (e.g., sample indexing oligonucleotide) or other binding reagent oligonucleotide(s) in the mixture can be different in different implementations. In some embodiments, the ratio can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

A cellular component binding reagent can be conjugated with a binding reagent oligonucleotide (e.g., a sample indexing oligonucleotide), or not. In some embodiments, the percentage of the cellular component binding reagent conjugated with a binding reagent oligonucleotide (e.g., a sample indexing oligonucleotide) in a mixture comprising the cellular component binding reagent that is conjugated with the binding reagent oligonucleotide and the cellular component binding reagent(s) that is not conjugated with the binding reagent oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent conjugated with a sample indexing oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the percentage of the cellular component binding reagent not conjugated with a binding reagent oligonucleotide (e.g., a sample indexing oligonucleotide) in a mixture comprising a cellular component binding reagent conjugated with a binding reagent oligonucleotide (e.g., a sample indexing oligonucleotide) and the cellular component binding reagent that is not conjugated with the sample indexing oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent not conjugated with a binding reagent oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Cellular Component Cocktails

In some embodiments, a cocktail of cellular component binding reagents (e.g., an antibody cocktail) can be used to increase labeling sensitivity in the methods disclosed herein. Without being bound by any particular theory, it is believed that this may be because cellular component expression or protein expression can vary between cell types and cell states, making finding a universal cellular component binding reagent or antibody that labels all cell types challenging. For example, cocktail of cellular component binding reagents can be used to allow for more sensitive and efficient labeling of more sample types. The cocktail of cellular component binding reagents can include two or more different types of cellular component binding reagents, for example a wider range of cellular component binding reagents or antibodies. Cellular component binding reagents that label different cellular component targets can be pooled together to create a cocktail that sufficiently labels all cell types, or one or more cell types of interest.

In some embodiments, each of the plurality of compositions (e.g., sample indexing compositions) comprises a cellular component binding reagent. In some embodiments, a composition of the plurality of compositions comprises two or more cellular component binding reagents, wherein each of the two or more cellular component binding reagents is associated with a binding reagent oligonucleotide (e.g., a sample indexing oligonucleotide), wherein at least one of the two or more cellular component binding reagents is capable of specifically binding to at least one of the one or more cellular component targets. The sequences of the binding reagent oligonucleotides associated with the two or more cellular component binding reagents can be identical. The sequences of the binding reagent oligonucleotides associated with the two or more cellular component binding reagents can comprise different sequences. Each of the plurality of compositions can comprise the two or more cellular component binding reagents.

The number of different types of cellular component binding reagents (e.g., a CD147 antibody and a CD47 antibody) in a composition can be different in different implementations. A composition with two or more different types of cellular component binding reagents can be referred to herein as a cellular component binding reagent cocktail (e.g., a sample indexing composition cocktail). The number of different types of cellular component binding reagents in a cocktail can vary. In some embodiments, the number of different types of cellular component binding reagents in cocktail can be, or be about 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or a number or a range between any two of these values. In some embodiments, the number of different types of cellular component binding reagents in cocktail can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000. The different types of cellular component binding reagents can be conjugated to binding reagent oligonucleotides with the same or different sequences (e.g., sample indexing sequences).

Methods of Quantitative Analysis of Cellular Component Targets

In some embodiments, the methods disclosed herein can also be used for quantitative analysis of a plurality of cellular component targets (for example, protein targets) in a sample using the compositions disclosed herein and oligonucleotide probes that can associate a barcode sequence (e.g., a molecular label sequence) to the oligonucleotides of the cellular component binding reagents (e.g., protein binding reagents). The oligonucleotides of the cellular component binding reagents can be, or comprise, an antibody oligonucleotide, a sample indexing oligonucleotide, a cell identification oligonucleotide, a control particle oligonucleotide, a control oligonucleotide, an interaction determination oligonucleotide, etc. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, etc., or a mixture of cells from different subjects.

In some embodiments, the sample can comprise a plurality of single cells separated into individual compartments, such as microwells in a microwell array.

In some embodiments, the binding target of the plurality of cellular component target (i.e., the cellular component target) can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component target is a protein target. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded cellular components in an organism. In some embodiments, the plurality of cellular component targets can comprise at least 2, at least 3, at least 4, at least 5, at least 10, at least 20, at least 30, at least 40, at least 50, at least 100, at least 1000, at least 10000, or more different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95% or 100%, of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100%, of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are cell-surface cellular components, such as cell-surface proteins, unbound compositions can be removed by washing the cells with buffer such that only compositions that specifically bind to the cellular component targets remain with the cells.

In some embodiments, the methods disclosed herein can comprise associating an oligonucleotide (e.g., a barcode, or a stochastic barcode), including a barcode sequence (such as a molecular label), a cell label, a sample label, etc., or any combination thereof, to the plurality of oligonucleotides associated with the cellular component binding reagents. For example, a plurality of oligonucleotide probes comprising a barcode can be used to hybridize to the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality associated with oligonucleotides of the cellular component binding reagents, the plurality of oligonucleotides of the cellular component binding reagents can hybridize to the oligonucleotide probes. The oligonucleotide probes can be contacted at a non-depletable ratio such that each distinct oligonucleotide of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of oligonucleotides of the compositions.

Methods of Simultaneous Quantitative Analysis of Cellular Component and Nucleic Acid Targets In some embodiments, the methods disclosed herein can also be used for simultaneous quantitative analysis of a plurality of cellular component targets (e.g., protein targets) and a plurality of nucleic acid target molecules in a sample using the compositions disclosed herein and oligonucleotide probes that can associate a barcode sequence (e.g., a molecular label sequence) to both the oligonucleotides of the cellular component binding reagents and nucleic acid target molecules. Other methods of simultaneous quantitative analysis of a plurality of cellular component targets and a plurality of nucleic acid target molecules are described in U.S. Patent Application Publication No. US2018/0088112 and U.S. Patent Application Publication No. US2018/0346970; the content of each of these is incorporated herein by reference in its entirety. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, or a mixture of cells from different subjects.

In some embodiments, the sample can comprise a plurality of single cells separated into individual compartments, such as microwells in a microwell array.

In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components, such as expressed proteins, in an organism, or one or more cells of the organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components, such as proteins could be expressed, in an organism, or one or more cells of the organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are on the cell surface, such as cell-surface proteins, unbound compositions can be removed by washing the cells with buffer such that only compositions that specifically bind to the cellular component targets remain with the cells.

In some embodiments, the methods disclosed herein can provide releasing the plurality of nucleic acid target molecules from the sample, e.g., cells. For example, the cells can be lysed to release the plurality of nucleic acid target molecules. Cell lysis may be accomplished by any of a variety of means, for example, by chemical treatment, osmotic shock, thermal treatment, mechanical treatment, optical treatment, or any combination thereof. Cells may be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof.

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, mRNA molecules, rRNA molecules, siRNA molecules, or a combination thereof, and can be double-stranded or single-stranded. In some embodiments, the plurality of nucleic acid molecules comprise, or comprise about, 100, 1000, 10000, 20000, 30000, 40000, 50000, 100000, 1000000, or a number or a range between any two of these values, species. In some embodiments, the plurality of nucleic acid molecules comprise at least, or comprise at most, 100, 1000, 10000, 20000, 30000, 40000, 50000, 100000, or 1000000, species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of nucleic acid target molecules and the plurality of oligonucleotides of the cellular component binding reagents. For example, a plurality of oligonucleotide probes comprising a stochastic barcode can be used to hybridize to the plurality of nucleic acid target molecules and the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality of nucleic acid target molecules and the plurality of oligonucleotides of the cellular component binding reagents, the plurality of nucleic acid target molecules and the plurality of oligonucleotides of the cellular component binding reagents can hybridize to the oligonucleotide probes. The oligonucleotide probes can be contacted at a non-depletable ratio such that each distinct nucleic acid target molecules and oligonucleotides of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of nucleic acid target molecules and the plurality of oligonucleotides of the compositions.

Simultaneous Quantitative Analysis of Protein and Nucleic Acid Targets

In some embodiments, the methods disclosed herein also can be used for simultaneous quantitative analysis of multiple types of target molecules, for example protein and nucleic acid targets. For example, the target molecules can be, or comprise, cellular components. There are provided, in some embodiments, methods of simultaneous quantitative analysis of both nucleic acid targets and other cellular component targets (e.g., proteins) in single cells. In some embodiments, a plurality of compositions, etc., each comprising a cellular component binding reagent, such as an antibody, is provided. Different cellular component binding reagents, such as antibodies, which bind to different cellular component targets are conjugated with different unique identifiers. Next, the cellular component binding reagents can be incubates with a sample containing a plurality of cells. The different cellular component binding reagents can specifically bind to cellular components on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer. The cells with the cellular component binding reagents can be then separated into a plurality of compartments, such as a microwell array, wherein a single compartment is sized to fit a single cell and a single bead. Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides conjugated to the cellular component binding reagent can be detached from the cellular component binding reagent using chemical, optical or other means. The cell can be lysed to release nucleic acids within the cell, such as genomic DNA or cellular mRNA. Cellular mRNA, oligonucleotides or both can be captured by the oligonucleotide probes on bead, for example, by hybridizing to the poly(dT) sequence. A reverse transcriptase can be used to extend the oligonucleotide probes hybridized to the cellular mRNA and the oligonucleotides using the cellular mRNA and the oligonucleotides as templates. The extension products produced by the reverse transcriptase can be subject to amplification and sequencing. Sequencing reads can be subject to demultiplexing of sequences or identifies of cell labels, barcodes (e.g., molecular labels), genes, cellular component binding reagent specific oligonucleotides (e.g., antibody specific oligonucleotides), etc., which can give rise to a digital representation of cellular components and gene expression of each single cell in the sample.

Association of Barcodes

The oligonucleotides associated with the cellular component binding reagents (e.g., antigen binding reagents or protein binding reagents) and/or the nucleic acid molecules may randomly associate with the oligonucleotide probes (e.g., barcodes, such as stochastic barcodes). The oligonucleotides associated with the cellular component binding reagents, referred to herein as binding reagent oligonucleotides, can be, or comprise oligonucleotides of the disclosure, such as an antibody oligonucleotide, a sample indexing oligonucleotide, a cell identification oligonucleotide, a control particle oligonucleotide, a control oligonucleotide, an interaction determination oligonucleotide, etc. Association can, for example, comprise hybridization of an oligonucleotide probe's target binding region to a complementary portion of the target nucleic acid molecule and/or the oligonucleotides of the protein binding reagents. For example, a oligo(dT) region of a barcode (e.g., a stochastic barcode) can interact with a poly(A) tail of a target nucleic acid molecule and/or a poly(A) tail of an oligonucleotide of a protein binding reagent. The assay conditions used for hybridization (e.g., buffer pH, ionic strength, temperature, etc.) can be chosen to promote formation of specific, stable hybrids.

The disclosure provides for methods of associating a molecular label with a target nucleic acid and/or an oligonucleotide associated with a cellular component binding reagent using reverse transcription. As a reverse transcriptase can use both RNA and DNA as template. For example, the oligonucleotide originally conjugated on the cellular component binding reagent can be either RNA or DNA bases, or both. A binding reagent oligonucleotide can be copied and linked (e.g., covalently linked) to a cell label and a barcode sequence (e.g., a molecular label) in addition to the sequence, or a portion thereof, of the binding reagent sequence. As another example, an mRNA molecule can be copied and linked (e.g., covalently linked) to a cell label and a barcode sequence (e.g., a molecular label) in addition to the sequence of the mRNA molecule, or a portion thereof.

In some embodiments, molecular labels can be added by ligation of an oligonucleotide probe target binding region and a portion of the target nucleic acid molecule and/or the oligonucleotides associated with (e.g., currently, or previously, associated with) with cellular component binding reagents. For example, the target binding region may comprise a nucleic acid sequence that can be capable of specific hybridization to a restriction site overhang (e.g., an EcoRI sticky-end overhang). The methods can further comprise treating the target nucleic acids and/or the oligonucleotides associated with cellular component binding reagents with a restriction enzyme (e.g., EcoRI) to create a restriction site overhang. A ligase (e.g., T4 DNA ligase) may be used to join the two fragments.

Determining the Number or Presence of Unique Molecular Label Sequences

In some embodiments, the methods disclosed herein comprise determining the number or presence of unique molecular label sequences for each unique identifier, each nucleic acid target molecule, and/or each binding reagent oligonucleotides (e.g., antibody oligonucleotides). For example, the sequencing reads can be used to determine the number of unique molecular label sequences for each unique identifier, each nucleic acid target molecule, and/or each binding reagent oligonucleotide. As another example, the sequencing reads can be used to determine the presence or absence of a molecular label sequence (such as a molecular label sequence associated with a target, a binding reagent oligonucleotide, an antibody oligonucleotide, a sample indexing oligonucleotide, a cell identification oligonucleotide, a control particle oligonucleotide, a control oligonucleotide, an interaction determination oligonucleotide, etc. in the sequencing reads).

In some embodiments, the number of unique molecular label sequences for each unique identifier, each nucleic acid target molecule, and/or each binding reagent oligonucleotide indicates the quantity of each cellular component target (e.g., an antigen target or a protein target) and/or each nucleic acid target molecule in the sample. In some embodiments, the quantity of a cellular component target and the quantity of its corresponding nucleic acid target molecules, e.g., mRNA molecules, can be compared to each other. In some embodiments, the ratio of the quantity of a cellular component target and the quantity of its corresponding nucleic acid target molecules, e.g., mRNA molecules, can be calculated. The cellular component targets can be, for example, cell surface protein markers. In some embodiments, the ratio between the protein level of a cell surface protein marker and the level of the mRNA of the cell surface protein marker is low.

The methods disclosed herein can be used for a variety of applications. For example, the methods disclosed herein can be used for proteome and/or transcriptome analysis of a sample. In some embodiments, the methods disclosed herein can be used to identify a cellular component target and/or a nucleic acid target, i.e., a biomarker, in a sample. In some embodiments, the cellular component target and the nucleic acid target correspond to each other, i.e., the nucleic acid target encodes the cellular component target. In some embodiments, the methods disclosed herein can be used to identify cellular component targets that have a desired ratio between the quantity of the cellular component target and the quantity of its corresponding nucleic acid target molecule in a sample, e.g., mRNA molecule. In some embodiments, the ratio is, or is about, 0.001, 0.01, 0.1, 1, 10, 100, 1000, or a number or a range between any two of the above values. In some embodiments, the ratio is at least, or is at most, 0.001, 0.01, 0.1, 1, 10, 100, or 1000. In some embodiments, the methods disclosed herein can be used to identify cellular component targets in a sample that the quantity of its corresponding nucleic acid target molecule in the sample is, or is about, 1000, 100, 10, 5, 21, 0, or a number or a range between any two of these values. In some embodiments, the methods disclosed herein can be used to identify cellular component targets in a sample that the quantity of its corresponding nucleic acid target molecule in the sample is more than, or less than, 1000, 100, 10, 5, 21, or 0.

Compositions and Kits

Some embodiments disclosed herein provide kits and compositions for simultaneous quantitative analysis of a plurality of cellular components (e.g., proteins) and/or a plurality of nucleic acid target molecules in a sample. The kits and compositions can, in some embodiments, comprise a plurality of cellular component binding reagents (e.g., a plurality of protein binding reagents) each conjugated with an oligonucleotide, wherein the oligonucleotide comprises a unique identifier for the cellular component binding reagent, and a plurality of oligonucleotide probes, wherein each of the plurality of oligonucleotide probes comprises a target binding region, a barcode sequence (e.g., a molecular label sequence), wherein the barcode sequence is from a diverse set of unique barcode sequences. In some embodiments, each of the oligonucleotides can comprise a molecular label, a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., oligodA$_{18}$ (unanchored to a solid support) or oligoA$_{18}$V (anchored to a solid support). The oligonucleotides can comprise DNA residues, RNA residues, or both.

Disclosed herein include a plurality of sample indexing compositions. Each of the plurality of sample indexing compositions can comprise two or more cellular component binding reagents. Each of the two or more cellular component binding reagents can be associated with a sample indexing oligonucleotide. At least one of the two or more cellular component binding reagents can be capable of specifically binding to at least one cellular component target. The sample indexing oligonucleotide can comprise a sample indexing sequence for identifying sample origin of one or more cells of a sample. Sample indexing sequences of at least two sample indexing compositions of the plurality of sample indexing compositions can comprise different sequences.

Disclosed herein include kits comprising sample indexing compositions for cell identification. In some embodiments. Each of two sample indexing compositions comprises a cellular component binding reagent (e.g., a protein binding reagent) associated with a sample indexing oligonucleotide, wherein the cellular component binding reagent is capable of specifically binding to at least one of one or more cellular component targets (e.g., one or more protein targets), wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof.

Disclosed herein include kits for cell identification. In some embodiments, the kit comprises: two or more sample indexing compositions. Each of the two or more sample indexing compositions can comprise a cellular component binding reagent (e.g., an antigen binding reagent) associated with a sample indexing oligonucleotide, wherein the cellular component binding reagent is capable of specifically binding to at least one of one or more cellular component targets, wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof. Disclosed herein include kits for multiplet identification. In some embodiments, the kit comprises two sample indexing compositions. Each of two sample indexing compositions can comprise a cellular component binding reagent (e.g., an antigen binding reagent) associated with a sample indexing oligonucleotide, wherein the antigen binding reagent is capable of specifically binding to at least one of one or more cellular component targets (e.g., antigen targets), wherein the sample indexing oligonucleotide comprises a sample indexing sequence, and wherein sample indexing sequences of the two sample indexing compositions comprise different sequences.

The unique identifiers (or oligonucleotides associated with cellular component binding reagents, such as binding reagent oligonucleotides, antibody oligonucleotides, sample indexing oligonucleotides, cell identification oligonucleotides, control particle oligonucleotides, control oligonucleotides, or interaction determination oligonucleotides) can have any suitable length, for example, from about 25 nucleotides to about 45 nucleotides long. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as any protein binding reagents (e.g., antibodies or fragments thereof, aptamers, small molecules, ligands, peptides, oligonucleotides, etc., or any combination thereof). In some embodiments, the cellular component binding reagents can be polyclonal antibodies, monoclonal antibodies, recombinant antibodies, single-chain antibody (scAb), or fragments thereof, such as Fab, Fv, etc. In some embodiments, the plurality of protein binding reagents can comprise, or comprise about, 20, 30, 40, 50, 60, 70, 80, 90, 100, 200, 300, 400, 500, 600, 700, 800, 900, 1000, 2000, 5000, or a number or a range between any tow of these values, different protein binding reagents. In some embodiments, the plurality of protein binding reagents can comprise at least, or comprise at most, 20, 30, 40, 50, 60, 70, 80, 90, 100, 200, 300, 400, 500, 600, 700, 800, 900, 1000, 2000, or 5000, different protein binding reagents.

In some embodiments, the oligonucleotide is conjugated with the cellular component binding reagent through a linker. In some embodiments, the oligonucleotide can be conjugated with the protein binding reagent covalently. In some embodiment, the oligonucleotide can be conjugated with the protein binding reagent non-covalently. In some embodiments, the linker can comprise a chemical group that reversibly or irreversbily attached the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, a disulfide bond, a streptavidin, a biotin, an amine, etc. In some embodiments, the chemical group can be conjugated to the protein binding reagent through a primary amine on an amino acid, such as lysine, or the N-terminus. The oligonucleotide can be conjugated to any suitable site of the protein binding reagent, as long as it does not interfere with the specific binding between the protein binding reagent and its protein target. In embodiments where the protein binding reagent is an antibody, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. In some embodiments, each protein binding reagent can be conjugated with a single oligonucleotide molecule. In some embodiments, each protein binding reagent can be conjugated with, or with about, 2, 3, 4, 5, 10, 20, 30, 40, 50, 100, 1000, or a number or a range between any tow of these values, oligonucleotide molecules, wherein each of the oligonucleotide molecule comprises the same unique identifier. In some embodiments, each protein binding reagent can be conjugated with more than one oligonucleotide molecule, for example, at least, or at most, 2, 3, 4, 5, 10, 20, 30, 40, 50, 100, or 1000, oligonucleotide molecules, wherein each of the oligonucleotide molecule comprises the same unique identifier.

In some embodiments, the plurality of cellular component binding reagents (e.g., protein binding reagents) are capable of specifically binding to a plurality of cellular component targets (e.g., protein targets) in a sample. The sample can be, or comprise, a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular proteins. In some embodiments, the plurality of cellular component targets can comprise intracellular proteins. In some embodiments, the plurality of cellular component targets can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values of all cellular component targets (e.g., proteins expressed or could be expressed) in an organism. In some embodiments, the plurality of cellular component targets can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all cellular component targets (e.g., proteins expressed or could be expressed) in an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

Sample Indexing Using Oligonucleotide-Conjugated Cellular Component Binding Reagent Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

An oligonucleotide-conjugated with an antibody, an oligonucleotide for conjugation with an antibody, or an oligonucleotide previously conjugated with an antibody is referred to herein as an antibody oligonucleotide ("AbOligo"). Antibody oligonucleotides in the context of sample indexing are referred to herein as sample indexing oligonucleotides. An antibody conjugated with an antibody oligonucleotide is referred to herein as a hot antibody or an oligonucleotide antibody. An antibody not conjugated with an antibody oligonucleotide is referred to herein as a cold antibody or an oligonucleotide free antibody. An oligonucleotide-conjugated with a binding reagent (e.g., a protein binding reagent), an oligonucleotide for conjugation with a binding reagent, or an oligonucleotide previously conjugated with a binding reagent is referred to herein as a reagent oligonucleotide. Reagent oligonucleotides in the context of sample indexing are referred to herein as sample indexing oligonucleotides. A binding reagent conjugated with an antibody oligonucleotide is referred to herein as a hot binding reagent or an oligonucleotide binding reagent. A binding reagent not conjugated with an antibody oligonucleotide is referred to herein as a cold binding reagent or an oligonucleotide free binding reagent.

Figure 5:
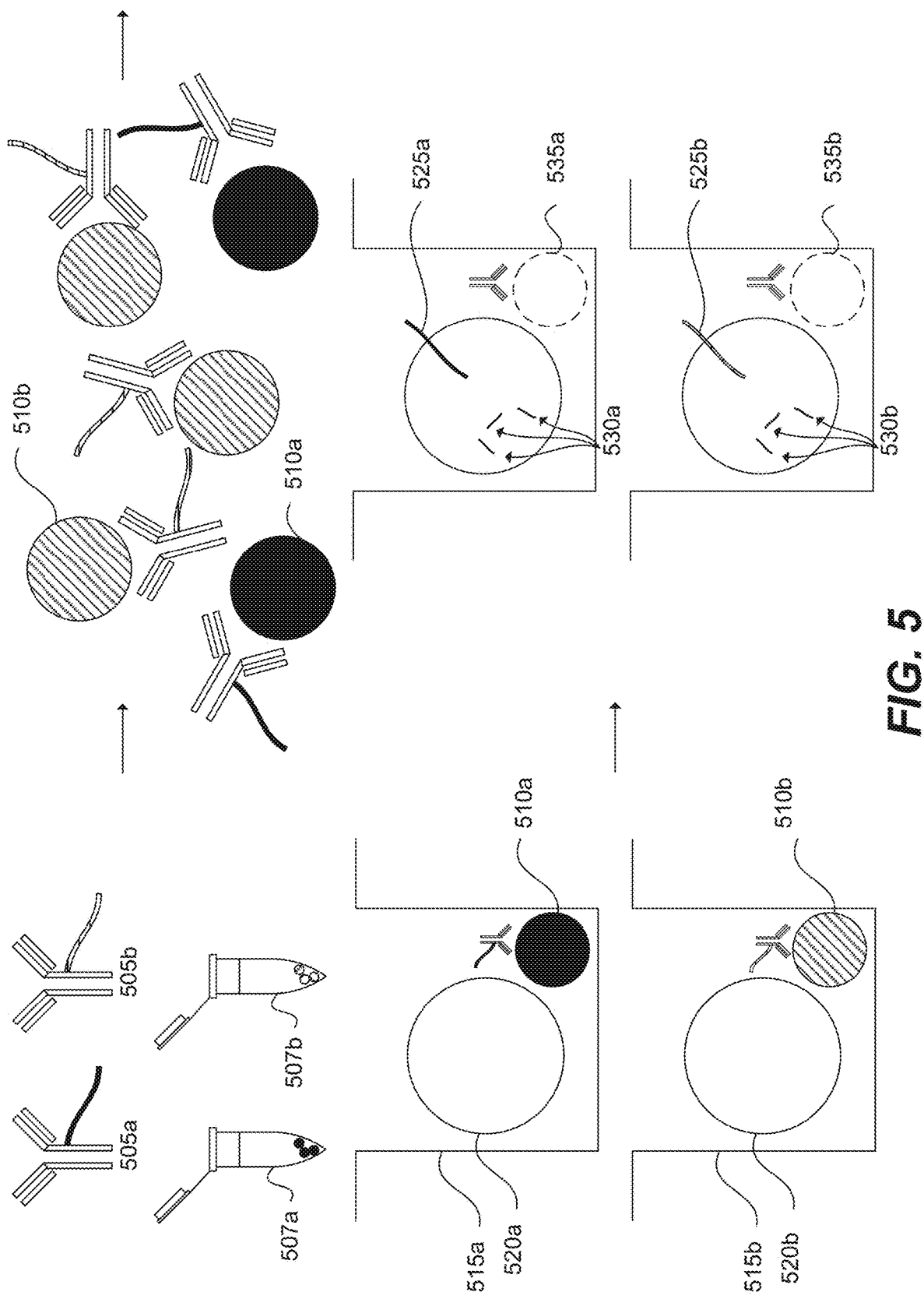
FIG. 5 shows a schematic illustration of an exemplary workflow of using oligonucleotide-associated antibodies for sample indexing.

FIG. 5 shows a schematic illustration of an exemplary workflow using oligonucleotide-associated cellular component binding reagents for sample indexing. In some embodiments, a plurality of compositions 505a, 505b, etc., each comprising a binding reagent is provided. The binding reagent can be a protein binding reagent, such as an antibody. The cellular component binding reagent can comprise an antibody, a tetramer, an aptamers, a protein scaffold, or a combination thereof. The binding reagents of the plurality of compositions 505a, 505b can bind to an identical cellular component target. For example, the binding reagents of the plurality of compositions 505, 505b can be identical (except for the sample indexing oligonucleotides associated with the binding reagents).

Different compositions can include binding reagents conjugated with sample indexing oligonucleotides with different sample indexing sequences. The number of different compositions can be different in different implementations. In some embodiments, the number of different compositions can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of different compositions can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

In some embodiments, the sample indexing oligonucleotides of binding reagents in one composition can include an identical sample indexing sequence. The sample indexing oligonucleotides of binding reagents in one composition may not be identical. In some embodiments, the percentage of sample indexing oligonucleotides of binding reagents in one composition with an identical sample indexing sequence can be, or be about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values. In some embodiments, the percentage of sample indexing oligonucleotides of binding reagents in one composition with an identical sample indexing sequence can be at least, or be at most, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9%.

The compositions 505a and 505b can be used to label samples of different samples. For example, the sample indexing oligonucleotides of the cellular component binding reagent in the composition 505a can have one sample indexing sequence and can be used to label cells 510a, shown as black circles, in a sample 507a, such as a sample of a patient. The sample indexing oligonucleotides of the cellular component binding reagents in the composition 505b can have another sample indexing sequence and can be used to label cells 510b, shown as hatched circles, in a sample 507b, such as a sample of another patient or another sample of the same patient. The cellular component binding reagents can specifically bind to cellular component targets or proteins on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer.

The cells with the cellular component binding reagents can be then separated into a plurality of compartments, such as a microwell array, wherein a single compartment 515a, 515b is sized to fit a single cell 510a and a single bead 520a or a single cell 510b and a single bead 520b. Each bead 520a, 520b can comprise a plurality of oligonucleotide probes, which can comprise a cell label that is common to all oligonucleotide probes on a bead, and molecular label sequences. In some embodiments, each oligonucleotide probe can comprise a target binding region, for example, a poly(dT) sequence. The sample indexing oligonucleotides 525a conjugated to the cellular component binding reagent of the composition 505a can be configured to be (or can be) detachable or non-detachable from the cellular component binding reagent. The sample indexing oligonucleotides 525a conjugated to the cellular component binding reagent of the composition 505a can be detached from the cellular component binding reagent using chemical, optical or other means. The sample indexing oligonucleotides 525b conjugated to the cellular component binding reagent of the composition 505b can be configured to be (or can be) detachable or non-detachable from the cellular component binding reagent. The sample indexing oligonucleotides 525b conjugated to the cellular component binding reagent of the composition 505b can be detached from the cellular component binding reagent using chemical, optical or other means.

The cell 510a can be lysed to release nucleic acids within the cell 510a, such as genomic DNA or cellular mRNA 530a. The lysed cell 535a is shown as a dotted circle. Cellular mRNA 530a, sample indexing oligonucleotides 525a, or both can be captured by the oligonucleotide probes on bead 520a, for example, by hybridizing to the poly(dT) sequence. A reverse transcriptase can be used to extend the oligonucleotide probes hybridized to the cellular mRNA 530a and the oligonucleotides 525a using the cellular mRNA 530a and the oligonucleotides 525a as templates. The extension products produced by the reverse transcriptase can be subject to amplification and sequencing.

Similarly, the cell 510b can be lysed to release nucleic acids within the cell 510b, such as genomic DNA or cellular mRNA 530b. The lysed cell 535b is shown as a dotted circle. Cellular mRNA 530b, sample indexing oligonucleotides 525b, or both can be captured by the oligonucleotide probes on bead 520b, for example, by hybridizing to the poly(dT) sequence. A reverse transcriptase can be used to extend the oligonucleotide probes hybridized to the cellular mRNA 530b and the oligonucleotides 525b using the cellular mRNA 530b and the oligonucleotides 525b as templates. The extension products produced by the reverse transcriptase can be subject to amplification and sequencing.

Sequencing reads can be subject to demultiplexing of cell labels, molecular labels, gene identities, and sample identities (e.g., in terms of sample indexing sequences of sample indexing oligonucleotides 525a and 525b). Demultiplexing of cell labels, molecular labels, and gene identities can give rise to a digital representation of gene expression of each single cell in the sample. Demultiplexing of cell labels, molecular labels, and sample identities, using sample indexing sequences of sample indexing oligonucleotides, can be used to determine a sample origin.

In some embodiments, cellular component binding reagents against cellular component binding reagents on the cell surface can be conjugated to a library of unique sample indexing oligonucleotides to allow cells to retain sample identity. For example, antibodies against cell surface markers can be conjugated to a library of unique sample indexing oligonucleotides to allow cells to retain sample identity. This will enable multiple samples to be loaded onto the same Rhapsody™ cartridge as information pertaining sample source is retained throughout library preparation and sequencing. Sample indexing can allow multiple samples to be run together in a single experiment, simplifying and shortening experiment time, and eliminating batch effect.

Disclosed herein include methods for sample identification. In some embodiments, the method comprise: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions. The method can include barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, the method for sample identification comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; and identifying sample origin of at least one cell of the one or more cells based on the sample indexing sequence of at least one sample indexing oligonucleotide of the plurality of sample indexing compositions.

In some embodiments, identifying the sample origin of the at least one cell comprises: barcoding (e.g., stochastically barcoding) sample indexing oligonucleotides of the plurality of sample indexing compositions using a plurality of barcodes (e.g., stochastic barcodes) to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides. In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, identifying the sample origin of the at least one cell can comprise identifying the presence or absence of the sample indexing sequence of at least one sample indexing oligonucleotide of the plurality of sample indexing compositions. Identifying the presence or absence of the sample indexing sequence can comprise: replicating the at least one sample indexing oligonucleotide to generate a plurality of replicated sample indexing oligonucleotides; obtaining sequencing data of the plurality of replicated sample indexing oligonucleotides; and identifying the sample origin of the cell based on the sample indexing sequence of a replicated sample indexing oligonucleotide of the plurality of sample indexing oligonucleotides that correspond to the least one barcoded sample indexing oligonucleotide in the sequencing data.

In some embodiments, replicating the at least one sample indexing oligonucleotide to generate the plurality of replicated sample indexing oligonucleotides comprises: prior to replicating the at least one barcoded sample indexing oligonucleotide, ligating a replicating adaptor to the at least one barcoded sample indexing oligonucleotide. Replicating the at least one barcoded sample indexing oligonucleotide can comprise replicating the at least one barcoded sample indexing oligonucleotide using the replicating adaptor ligated to the at least one barcoded sample indexing oligonucleotide to generate the plurality of replicated sample indexing oligonucleotides.

In some embodiments, replicating the at least one sample indexing oligonucleotide to generate the plurality of replicated sample indexing oligonucleotides comprises: prior to replicating the at least one barcoded sample indexing oligonucleotide, contacting a capture probe with the at least one sample indexing oligonucleotide to generate a capture probe hybridized to the sample indexing oligonucleotide; and extending the capture probe hybridized to the sample indexing oligonucleotide to generate a sample indexing oligonucleotide associated with the capture probe. Replicating the at least one sample indexing oligonucleotide can comprise replicating the sample indexing oligonucleotide associated with the capture probe to generate the plurality of replicated sample indexing oligonucleotides.

Cell Overloading and Multiplet Identification

Also disclosed herein include methods, kits and systems for identifying cell overloading and multiplet. Such methods, kits and systems can be used in, or in combination with, any suitable methods, kits and systems disclosed herein, for example the methods, kits and systems for measuring cellular component expression level (such as protein expression level) using cellular component binding reagents associated with oligonucleotides.

Using current cell-loading technology, when about 20000 cells are loaded into a microwell cartridge or array with ~60000 microwells, the number of microwells or droplets with two or more cells (referred to as doublets or multiplets) can be minimal. However, when the number of cells loaded increases, the number of microwells or droplets with multiple cells can increase significantly. For example, when about 50000 cells are loaded into about 60000 microwells of a microwell cartridge or array, the percentage of microwells with multiple cells can be quite high, such as 11-14%. Such loading of high number of cells into microwells can be referred to as cell overloading. However, if the cells are divided into a number of groups (e.g., 5), and cells in each group are labeled with sample indexing oligonucleotides with distinct sample indexing sequences, a cell label (e.g., a cell label of a barcode, such as a stochastic barcode) associated with two or more sample indexing sequences can be identified in sequencing data and removed from subsequent processing. In some embodiments, the cells are divided into a large number of groups (e.g., 10000), and cells in each group are labeled with sample indexing oligonucleotides with distinct sample indexing sequences, a sample label associated with two or more sample indexing sequences can be identified in sequencing data and removed from subsequent processing. In some embodiments, different cells are labeled with cell identification oligonucleotides with distinct cell identification sequences, a cell identification sequence associated with two or more cell identification oligonucleotides can be identified in sequencing data and removed from subsequent processing. Such higher number of cells can be loaded into microwells relative to the number of microwells in a microwell cartridge or array.

Disclosed herein include methods for sample identification. In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more cell label sequences that is each associated with two or more sample indexing sequences in the sequencing data obtained; and removing the sequencing data associated with the one or more cell label sequences that is each associated with two or more sample indexing sequences from the sequencing data obtained and/or excluding the sequencing data associated with the one or more cell label sequences that is each associated with two or more sample indexing sequences from subsequent analysis (e.g., single cell mRNA profiling, or whole transcriptome analysis). In some embodiments, the sample indexing oligonucleotide comprises a barcode sequence (e.g., a molecular label sequence), a binding site for a universal primer, or a combination thereof.

For example, the method can be used to load 50000 or more cells (compared to 10000-20000 cells) using sample indexing. Sample indexing can use oligonucleotide-conjugated cellular component binding reagents (e.g., antibodies) or cellular component binding reagents against a cellular component (e.g., a universal protein marker) to label cells from different samples with a unique sample index. When two or more cells from different samples, two or more cells from different populations of cells of a sample, or two or more cells of a sample, are captured in the same microwell or droplet, the combined "cell" (or contents of the two or more cells) can be associated with sample indexing oligonucleotides with different sample indexing sequences (or cell identification oligonucleotides with different cell identification sequences). The number of different populations of cells can be different in different implementations. In some embodiments, the number of different populations can be, or be about, 2, 3, 4, 5, 6, 7, 8, 9, 10, 20, 30, 40, 50, 60, 70, 80, 90, 100, or a number or a range between any two of these values. In some embodiments, the number of different populations can be at least, or be at most, 2, 3, 4, 5, 6, 7, 8, 9, 10, 20, 30, 40, 50, 60, 70, 80, 90, or 100. The number, or the average number, of cells in each population can be different in different implementations. In some embodiments, the number, or the average number, of cells in each population can be, or be about, 1, 2, 3, 4, 5, 6, 7, 8, 9, 10, 20, 30, 40, 50, 60, 70, 80, 90, 100, or a number or a range between any two of these values. In some embodiments, the number, or the average number, of cells in each population can be at least, or be at most, 1, 2, 3, 4, 5, 6, 7, 8, 9, 10, 20, 30, 40, 50, 60, 70, 80, 90, or 100. When the number, or the average number, of cells in each population is sufficiently small (e.g., equal to, or fewer than, 50, 25, 10, 5, 4, 3, 2, or 1 cells per population), the sample indexing composition for cell overloading and multiplet identification can be referred to as cell identification compositions.

Cells of a sample can be divided into multiple populations by aliquoting the cells of the sample into the multiple populations. A "cell" associated with more than one sample indexing sequence in the sequencing data can be identified as a "multiplet" based on two or more sample indexing sequences associated with one cell label sequence (e.g., a cell label sequence of a barcode, such as a stochastic barcode) in the sequencing data. The sequencing data of a combined "cell" is also referred to herein as a multiplet. A multiplet can be a doublet, a triplet, a quartet, a quintet, a sextet, a septet, an octet, a nonet, or any combination thereof. A multiplet can be any n-plet. In some embodiments, n is, or is about, 2, 3, 4, 5, 6, 7, 8, 9, 10, 11, 12, 13, 14, 15, 16, 17, 18, 19, 20, or a range between any two of these values. In some embodiments, n is at least, or is at most, 2, 3, 4, 5, 6, 7, 8, 9, 10, 11, 12, 13, 14, 15, 16, 17, 18, 19, or 20.

When determining expression profiles of single cells, two cells may be identified as one cell and the expression profiles of the two cells may be identified as the expression profile for one cell (referred to as a doublet expression profile). For example, when determining expression profiles of two cells using barcoding (e.g., stochastic barcoding), the mRNA molecules of the two cells may be associated with barcodes having the same cell label. As another example, two cells may be associated with one particle (e.g., a bead). The particle can include barcodes with the same cell label. After lysing the cells, the mRNA molecules in the two cells can be associated with the barcodes of the particle, thus the same cell label. Doublet expression profiles can skew the interpretation of the expression profiles.

A doublet can refer to a combined "cell" associated with two sample indexing oligonucleotides with different sample indexing sequences. A doublet can also refer to a combined "cell" associated with sample indexing oligonucleotides with two sample indexing sequences. A doublet can occur when two cells associated with two sample indexing oligonucleotides of different sequences (or two or more cells associated with sample indexing oligonucleotides with two different sample indexing sequences) are captured in the same microwell or droplet, the combined "cell" can be associated with two sample indexing oligonucleotides with different sample indexing sequences. A triplet can refer to a combined "cell" associated with three sample indexing oligonucleotides all with different sample indexing sequences, or a combined "cell" associated with sample indexing oligonucleotides with three different sample indexing sequences. A quartet can refer to a combined "cell" associated with four sample indexing oligonucleotides all with different sample indexing sequences, or a combined "cell" associated with sample indexing oligonucleotides with four different sample indexing sequences. A quintet can refer to a combined "cell" associated with five sample indexing oligonucleotides all with different sample indexing sequences, or a combined "cell" associated with sample indexing oligonucleotides with five different sample indexing sequences. A sextet can refer to a combined "cell" associated with six sample indexing oligonucleotides all with different sample indexing sequences, or a combined "cell" associated with sample indexing oligonucleotides with six different sample indexing sequences. A septet can refer to a combined "cell" associated with seven sample indexing oligonucleotides all with different sample indexing sequences, or a combined "cell" associated with sample indexing oligonucleotides with seven different sample indexing sequences. A octet can refer to a combined "cell" associated with eight sample indexing oligonucleotides all with different sample indexing sequences, or a combined "cell" associated with sample indexing oligonucleotides with eight different sample indexing sequences. A nonet can refer to a combined "cell" associated with nine sample indexing oligonucleotides all with different sample indexing sequences, or a combined "cell" associated with sample indexing oligonucleotides with nine different sample indexing sequences. A multiplet can occur when two or more cells associated with two or more sample indexing oligonucleotides of different sequences (or two or more cells associated with sample indexing oligonucleotides with two or more different sample indexing sequences) are captured in the same microwell or droplet, the combined "cell" can be associated with sample indexing oligonucleotides with two or more different sample indexing sequences.

As another example, the method can be used for multiplet identification, whether in the context of sample overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using sample indexing, one can recognize some of these multiplets by looking for cell labels that are each associated with or assigned to two or more sample indexing oligonucleotides with different sample indexing sequences (or sample indexing oligonucleotides with two or more sample indexing sequences). With sample indexing sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence;

obtaining sequencing data of the plurality of barcoded sample indexing oligonucleotides; and identifying one or more multiplet cell label sequences that is each associated with two or more sample indexing sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With sample indexing, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions. The number of pluralities of cells and the number of pluralities of sample indexing compositions can be different in different implementations. In some embodiments, the number of pluralities of cells and/or sample indexing compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of pluralities of cells and/or sample indexing compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number of cells can be different in different implementations. In some embodiments, the number, or the average number, of cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or the average number, or cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one cellular component binding reagent of the two sample indexing compositions using flow cytometry. In some embodiments, the method comprises: lysing the one or more cells from each of the plurality of samples.

In some embodiments, the sample indexing oligonucleotide is configured to be (or can be) detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using reducing reagent, such as dithiothreitol), heating, enzyme treatment, or any combination thereof.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of barcode sequence (e.g., the molecular label sequence) and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the barcode sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method includes: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can include: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, the method for cell identification comprise: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more cell label sequences that is each associated with two or more cell identification sequences in the sequencing data obtained; and removing the sequencing data associated with the one or more cell label sequences that is each associated with two or more cell identification sequences from the sequencing data obtained and/or excluding the sequencing data associated with the one or more cell label sequences that is each associated with two or more cell identification sequences from subsequent analysis (e.g., single cell mRNA profiling, or whole transcriptome analysis). In some embodiments, the cell identification oligonucleotide comprises a barcode sequence (e.g., a molecular label sequence), a binding site for a universal primer, or a combination thereof.

A multiplet (e.g., a doublet, triplet, etc) can occur when two or more cells associated with two or more cell identification oligonucleotides of different sequences (or two or more cells associated with cell identification oligonucleotides with two or more different cell identification sequences) are captured in the same microwell or droplet, the combined "cell" can be associated with cell identification oligonucleotides with two or more different cell identification sequences.

Cell identification compositions can be used for multiplet identification, whether in the context of cell overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using cell identification, one can recognize some of these multiplets by looking for cell labels (e.g., cell labels of barcodes, such as stochastic barcodes) that are each associated with or assigned to two or more cell identification oligonucleotides with different cell identification sequences (or cell identification oligonucleotides with two or more cell identification sequences). With cell identification sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more multiplet cell label sequences that is each associated with two or more cell identification sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With cell identification, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of one or more cells and the second plurality of one or more cells with the two cell identification compositions respectively comprises: contacting the first plurality of one or more cells with a first cell identification compositions of the two cell identification compositions; and contacting the first plurality of one or more cells with a second cell identification compositions of the two cell identification compositions. The number of pluralities of cell identification compositions can be different in different implementations. In some embodiments, the number of cell identification compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of cell identification compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number, or average number, of cells in each plurality of one or more cells can be different in different implementations. In some embodiments, the number, or average number, of cells in each plurality of one or more cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or average number, of cells in each plurality of one or more cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound cell identification compositions of the two cell identification compositions. Removing the unbound cell identification compositions can comprise washing cells of the first plurality of one or more cells and the second plurality of one or more cells with a washing buffer. Removing the unbound cell identification compositions can comprise selecting cells bound to at least one cellular component binding reagent of the two cell identification compositions using flow cytometry. In some embodiments, the method comprises: lysing the one or more cells from each of the plurality of samples.

In some embodiments, the cell identification oligonucleotide is configured to be (or can be) detachable or non-detachable from the cellular component binding reagent. The method can comprise detaching the cell identification oligonucleotide from the cellular component binding reagent. Detaching the cell identification oligonucleotide can comprise detaching the cell identification oligonucleotide from the cellular component binding reagent by UV photocleaving, chemical treatment (e.g., using reducing reagent, such as dithiothreitol), heating, enzyme treatment, or any combination thereof.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of barcode sequence (e.g., the molecular label sequence) and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

Methods of Spatial Encoding to Correlate Phenotypical Information and Agent Exposure with Sequencing Data in Single-Cell Multi-Omics Workflows Methods for determining mRNA expression profiles of single cells can be performed in a massively parallel manner. For example, the Precise™ assay can be used to determine the mRNA expression profiles of more than 10000 cells simultaneously. A substrate can comprise an array of microwells, wherein each microwell comprises a reaction chamber of defined volume that can entrap a single cell and a single solid support (e.g., a bead) comprising stochastic barcodes. The lysis of the single cells and labeling of target nucleic acid molecules released from said cells can be performed in a massively parallel manner in said array of reaction chambers. However, there is a need for compositions and methods to enable a determination of the spatial locations of nucleic acid target molecules within a plurality of partitions. For example, phenotypic information can be derived for said single cells in isolated partitions, such as, for example, morphology data acquired via imaging of said partitions. Current single-cell multi-omics workflows (e.g., BD Rhapsody & AbSeq systems) have the ability to capturing imaging data of single cells, which could be used for future applications such as high-throughput drug screening on single cells. Single-cell multi-omics workflows also generate sequencing readouts of single cells. However, current solutions that can link spatial information and gene expression are low throughput and often require special instrumentations, and there is a need for compositions and methods of correlating phenotypical information with sequencing data in single-cell multi-omics workflows. Furthermore, as disclosed herein, single cells can be exposed different concentrations and/or different types of one or more agents. However, there is a need for compositions and methods of correlating agent exposure with sequencing data in single-cell multi-omics workflows.

The systems, methods, compositions, and kits provided herein address the above-mentioned needs. There are provided, in some embodiments, methods of correlating phenotypical information and/or agent exposure with sequencing data in single-cell multi-omics workflows. In some embodiments, the methods comprise associating single cells with cell indexing oligonucleotides comprising cell indexing subsequences. In some embodiments, the methods comprise associating synthetic particles with cell indexing oligonucleotides. In some embodiments, synthetic particles associated with stochastic labels comprising cell indexing sequences are provided. Methods of labeling a plurality of cells with cell indexing oligonucleotides are disclosed herein, wherein the cell indexing oligonucleotides associated with the same cell comprise the same cell indexing sequence, and wherein the cell indexing oligonucleotides associated with different cells comprise different cell indexing sequences. Methods of associating a plurality of synthetic particles with cell indexing sequences are disclosed herein, wherein the cell indexing sequences associated with the same synthetic particle comprise the same cell indexing sequence, and wherein the cell indexing oligonucleotides associated with different synthetic particles comprise different cell indexing sequences. There are provided, in some embodiments, methods of generating a spatial index associated with cells and/or synthetic particles. Generating the spatial index can comprise contacting the cell indexing oligonucleotides and/or cell indexing sequence with a series of probes, some or all of which comprise a detectable moiety. The cell indexing sequence can comprise a series of n cell indexing subsequences, and a spatial index can comprise a series of n signals and/or absence of signals detected during n cycles of sequential hybridization and imaging with said probes. Generating the spatial index (e.g., spatial encoding) can occur within partitions, and each partition can thereby be associated with a spatial index. A cell indexing sequence (e.g., the sequence of the n cell indexing subsequences) can be derived from a spatial index. Sequencing data for each nucleic acid target molecule can be correlated with the identity of the partition from which nucleic acid target molecule originated using the methods and compositions provided herein. The identity of the partition from which nucleic acid target molecule originated can then be correlated with agent exposure and/or phenotypic information for said partition. For example, in some embodiments, unique cell indexing oligonucleotides are associated with single cells, and determining the spatial location of each nucleic acid target molecule comprises associating the cellular label of the partition and the cell indexing sequence of the partition. In other embodiments, the cellular label of each synthetic particle comprises of the cell indexing sequence, and determining the spatial location of each nucleic acid target molecule comprises associating the cellular label of the partition and the cell indexing sequence. In some such embodiments, the partitions (e.g., micro-wells of a barcoded cartridge) are pre-loaded with beads and spatial encoding is performed to generate a spatial index lookup table. The spatial index lookup table can provide the spatial index and/or the cell indexing sequence of the plurality of micro-wells of a barcoded cartridge, enabling a downstream user of the barcoded cartridge to determine the spatial locations of nucleic acid target molecules within a plurality of partitions and/or associate sequencing data with phenotypic data according the methods provided herein. The compositions and methods provided herein can be used with any single cell workflow. Single cell workflows can utilize microwell arrays or microwell cartridges (e.g., BD Resolve™) or microfluidics devices (e.g., 10× Genomics (San Francisco, CA), Drop-seq (McCarroll Lab, Harvard Medical School (Cambridge, Massachusett); Macosko et al., Cell, 2015 May 21 16; 5:1202, the content of which is incorporated herein by reference in its entirety), or Abseq (Mission Bio (San Francisco, CA); Shahi et al., Sci Rep. 2017 Mar. 14; 7:44447, the content of which is hereby incorporated by reference in its entirety) in combination with solid or semi-solid particles associated with stochastic barcodes (e.g., BD Resolve, or Drop-seq) or disruptable hydrogel particles enclosing releasable stochastic barcodes (e.g., 10× Genomics, or Abseq).

Methods of Labeling with Cell Indexing Oligonucleotides.

The disclosure provides compositions and methods for production of a repertoire of diverse cell indexing oligonucleotides using only a small set of indexing oligonucleotides. As disclosed herein, a set of large number of cell indexing oligonucleotides can be generated from a relatively small number of indexing oligonucleotides wherein the indexing oligonucleotides are connected to each other by various combinations. In this way, the number of different cell indexing oligonucleotides generated can be increased significantly through relatively small increases in the number of different indexing oligonucleotides, the number of indexing oligonucleotides connected to each other in a cell indexing oligonucleotide, or both. The method of the disclosure provides for simple molecular biology steps to carry out the combinatorial pairing of the indexing oligonucleotides. In some embodiments, ultra-diluted staining methods are employed to label each single cell with unique cell indexing oligonucleotides.

FIG. 6 shows non-limiting schematic illustration of a method of labeling a plurality of cells with cell indexing oligonucleotides by a combinatorial split-pool synthesis approach. A plurality of cells can be distributed into a plurality of first partitions. Cells in each first partition can be associated with a cellular component-binding reagent (antibody illustrated here) of a plurality of cellular component-binding reagents. The cellular component-binding reagent can be associated with a first indexing oligonucleotide with a first cell indexing subsequence, and two cellular component-binding reagents of the plurality of cellular component-binding reagents can be associated with first indexing oligonucleotides with different first cell indexing subsequences. The cellular component-binding reagent can be capable of specifically binding to the one or more cellular component targets, thereby generating cells associated with the first cell indexing subsequence, in each first partition of the plurality of first partitions. Cells in two first partitions of the plurality of first partitions can thereby be associated with different first cell indexing subsequences. The cells associated with the cellular component-binding reagents in each first partition can be pooled and the pooled cells can then be distributed into a plurality of second partitions. The pooled cells in each second partition can be associated with a second indexing oligonucleotide of a plurality of second indexing oligonucleotides with a second cell indexing subsequence, wherein the second indexing oligonucleotides of the plurality of second indexing oligonucleotides in two second partitions of the plurality of second partitions comprise different second cell indexing subsequences, thereby generating cells associated with the second cell indexing subsequence, in each second partition of the plurality of second partitions, wherein the cells in two second partitions of the plurality of second partitions are associated with different second cell indexing subsequences. Cells associated with the cellular component-binding reagent in each second partition of the plurality of second partitions associated with a cell indexing oligonucleotide can be generated, wherein the cell indexing sequence of the cell indexing oligonucleotide comprises the first cell indexing subsequence and the second cell indexing subsequence of the second cell indexing oligonucleotide associated with the second partition of the plurality of second partitions, via the cellular component-binding reagent associated with the first indexing oligonucleotide with the first cell indexing subsequence associated with each of the cells in the second partition. The split-pool method can be repeated for n times, generating cells labeled with cell indexing oligonucleotides comprising n cell indexing subsequences. Each cell can be associated with one or more unique cell indexing oligonucleotides, wherein the one or more unique cell indexing oligonucleotides associated with the same cell comprise the same cell indexing subsequences, and wherein the one or more unique cell indexing oligonucleotides associated with different cells comprise different cell indexing subsequences.

Figure 7A:
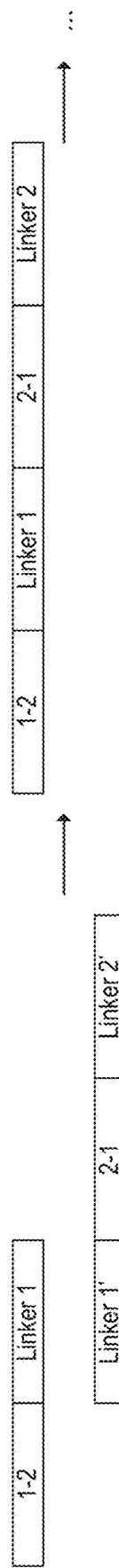
FIGS. 7A-7B show schematic illustrations of non-limiting exemplary methods for generating cell indexing oligonucleotides from indexing oligonucleotides.
Figure 7B:
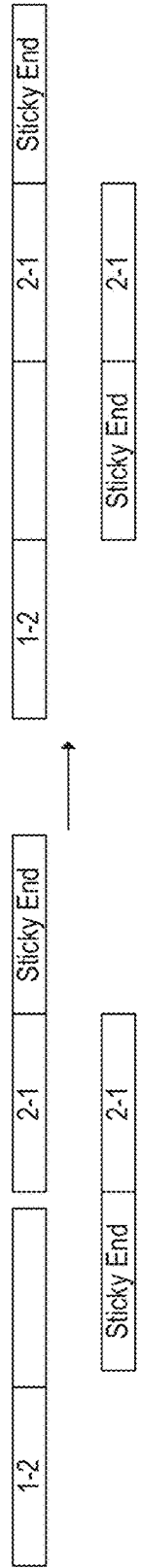

FIGS. 7A-7B show schematic illustrations of non-limiting exemplary methods for generating cell indexing oligonucleotides from indexing oligonucleotides. Indexing oligonucleotides can be concatenated together through linker sequences. In some embodiments, the first indexing oligonucleotide and/or second indexing oligonucleotide can be single-stranded oligonucleotides. As shown in FIG. 7A, a first indexing oligonucleotide can comprise a first cell indexing subsequence ("1-2") and a first linker sequence ("Linker 1"). The second indexing oligonucleotide can comprise a complementary sequence of the first linker sequence ("Linker 1"), a second cell indexing subsequence ("2-1") and a second linker sequence ("Linker 2"). The first linker sequence of the first indexing oligonucleotide can hybridize to the complementary sequence of the first linker sequence of the second indexing oligonucleotide, thereby generating a hybridized indexing oligonucleotide. The first indexing oligonucleotide of the hybridized indexing oligonucleotide can be extended, thereby generating the first cell indexing oligonucleotide comprising the first cell indexing sequence and the second cell indexing sequence. The extending can comprise extending the first indexing oligonucleotide of the hybridized indexing oligonucleotide using a DNA polymerase (e.g., Klenow large fragment) and/or a reverse transcriptase. The method can comprise removing the second complementary indexing oligonucleotide using an enzyme with 5' to 3' exonuclease activity (e.g., Lamba exonuclease). In some embodiments, the first indexing oligonucleotide and/or second indexing oligonucleotide can be double-stranded oligonucleotides. A first indexing oligonucleotide can comprise a first cell indexing subsequence ("1-2") and a first linker sequence. The first linker sequence can comprise a first restriction site recognized by a first restriction enzyme. The restriction enzyme, for example, BamHI, can generate a single stranded overhang for sticky ended ligation. In some embodiments, the linker sequence can comprise a nucleic acid sequence that is capable of specific hybridization to a restriction enzyme site overhang (e.g., an EcoRI sticky-end overhang). The second indexing oligonucleotide can comprise a first linker sequence, a second cell indexing subsequence ("2-1") and a second linker sequence. The second linker sequence can comprise a second restriction site recognized by a second restriction enzyme. The first and second restriction sites can comprise different restriction sites. As depicted in FIG. 7B, the first indexing oligonucleotide and second indexing oligonucleotide can be contacted with a first restriction enzyme that generates sticky ends within the first linker sequence. The sticky ends of the first linker sequence of the first indexing oligonucleotide and the first linker sequence of the second indexing oligonucleotide can hybridize and be ligated together.

Disclosed herein include methods for labeling a plurality of cells with cell indexing oligonucleotides. In some embodiments, the method comprises: (a) associating cells in each first partition of a plurality of first partitions with a cellular component-binding reagent of a plurality of cellular component-binding reagents, wherein each of the cells comprises one or more cellular component targets, wherein the cellular component-binding reagent is associated with a first indexing oligonucleotide with a first cell indexing subsequence, wherein two cellular component-binding reagents of the plurality of cellular component-binding reagents are associated with first indexing oligonucleotides with different first cell indexing subsequences, and wherein the cellular component-binding reagent is capable of specifically binding to the one or more cellular component targets, thereby generating cells associated with the first cell indexing subsequence, in each first partition of the plurality of first partitions, via the cellular component-binding reagent the first indexing oligonucleotide with the first cell indexing subsequence is associated with, wherein the cells in two first partitions of the plurality of first partitions are associated with different first cell indexing subsequences. The method can comprise (b) pooling the cells associated with the cellular component-binding reagents in each first partition of the plurality of first partitions. The method can comprise (c) distributing the pooled cells into a plurality of second partitions. The method can comprise (d) associating the pooled cells in each second partition of the plurality of second partitions with a second indexing oligonucleotide of a plurality of second indexing oligonucleotides with a second cell indexing subsequence, wherein the second indexing oligonucleotides of the plurality of second indexing oligonucleotides in two second partitions of the plurality of second partitions comprise different second cell indexing subsequences, thereby generating cells associated with the second cell indexing subsequence, in each second partition of the plurality of second partitions, wherein the cells in two second partitions of the plurality of second partitions are associated with different second cell indexing subsequences. The method can comprise (e) generating cells associated with the cellular component-binding reagent in each second partition of the plurality of second partitions associated with a cell indexing oligonucleotide, wherein the cell indexing sequence of the cell indexing oligonucleotide comprises the first cell indexing subsequence and the second cell indexing subsequence of the second cell indexing oligonucleotide associated with the second partition of the plurality of second partitions, via the cellular component-binding reagent associated with the first indexing oligonucleotide with the first cell indexing subsequence associated with each of the cells in the second partition.

The method can comprise, after step (e): (f) pooling the cells associated with the cellular component-binding reagents in each second partition of the plurality of second partitions. The method can comprise, prior to step (a): distributing cellular component-binding reagents of the plurality of cellular component-binding reagents into the plurality of first partitions. The method can comprise pooling the cells associated with the cellular component-binding reagent in each first partition of the plurality of first partitions. The method can comprise removing unbound first indexing oligonucleotides. In some embodiments, step (b) can comprise removing unbound cellular component-binding reagents.

The first indexing oligonucleotide can comprise a linker, and the cellular component-binding reagent can be associated with the first indexing oligonucleotide via the linker. In some embodiments, the first indexing oligonucleotide is a single-stranded oligonucleotide. In some embodiments, the 5' end of the first indexing oligonucleotide comprises the linker. In some embodiments, the second indexing oligonucleotide is a single-stranded oligonucleotide. The first indexing oligonucleotide can comprise a first linker sequence. The second indexing oligonucleotide can comprise a complementary sequence of the first linker sequence. The generating can comprise hybridizing the first linker sequence of the first indexing oligonucleotide to the complementary sequence of the first linker sequence of the second indexing oligonucleotide, thereby generating a hybridized indexing oligonucleotide. The generating can comprise extending the first indexing oligonucleotide of the hybridized indexing oligonucleotide, thereby generating the first cell indexing oligonucleotide comprising the first cell indexing sequence and the second cell indexing sequence. The extending can comprise extending the first indexing oligonucleotide of the hybridized indexing oligonucleotide using a DNA polymerase (e.g., Klenow large fragment) and/or a reverse transcriptase.

In some embodiments, the first indexing oligonucleotide is hybridized to a first complementary indexing oligonucleotide. In some embodiments, the first complementary indexing oligonucleotide can comprise a first linker sequence, the second indexing oligonucleotide can comprise a complementary sequence of the first linker sequence, and the generating can comprise hybridizing the first linker sequence of the first complementary indexing oligonucleotide to the complementary sequence of the first linker sequence of the second indexing oligonucleotide, thereby generating a hybridized indexing oligonucleotide. In some embodiments, the second indexing oligonucleotide is hybridized to a second complementary indexing oligonucleotide. The first indexing oligonucleotide can comprise a first linker sequence. The second complementary indexing oligonucleotide can comprise a complementary sequence of the first linker sequence. The generating can comprise hybridizing the first linker sequence of the first indexing oligonucleotide to the complementary sequence of the first linker sequence of the second complementary indexing oligonucleotide, thereby generating a hybridized indexing oligonucleotide. The first linker sequence can comprise a first restriction site recognized by a first restriction enzyme. The second indexing oligonucleotide can comprise a second restriction site recognized by a second restriction enzyme. The first and second restriction sites can comprise different restriction sites. The method can comprise ligating the first indexing oligonucleotide with the second indexing oligonucleotide. The method can comprise removing the first complementary indexing oligonucleotide or the second complementary indexing oligonucleotide. Removing can comprise contacting the hybridized indexing oligonucleotide with an enzyme with 5' to 3' exonuclease activity (e.g., Lamba exonuclease).

In some embodiments, the method comprises performing steps (c), (d), (e), and (f) for n times, wherein n is a positive integer greater than 1. The methods disclosed herein can comprise performing steps (c), (d), (e), and (f) for at least 1, 2, 3, 4, 5, 6, 7, 8, 9, 10, 11, 12, 13, 14, 15, 16, 17, 18, 19, or 20 times. In some embodiments, the nth indexing oligonucleotide can comprise an (n−1)th linker sequence and a target sequence. A target sequence can be complementary to a capture sequence of a stochastic label configured to capture the sequence of the cell indexing oligonucleotide. A target sequence can comprise a poly(A) sequence. The cell indexing oligonucleotide can comprise cell indexing subsequence$_1$-linker sequence$_1$-cell indexing subsequence$_2$-linker sequence$_2$- . . . cell indexing subsequence$_{n-1}$-linker sequence$_n$-cell indexing subsequence$_n$-target sequence. In some embodiments, two of the linker sequences are identical. All of the linker sequences can be identical. In some embodiments, two of the linker sequences are different. All of the linker sequences can be different. In some embodiments, the second indexing oligonucleotide comprises a second linker sequence. In some embodiments, the plurality of the first partitions and the plurality of the second partitions comprise an identical number of partitions. Two pluralities of partitions can comprise an identical number of partitions. Each of the pluralities of partitions can comprise an identical number of partitions. Each of the pluralities of partitions can comprise p partitions. In some embodiments, p is at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, or a number or a range between any two of these values. In some embodiments, each of the p partitions can comprise different cell indexing sequences. In some embodiments, the methods provided herein generate equal to or less than $p^n$ unique cell indexing oligonucleotides, wherein two unique cell indexing oligonucleotides comprise at least one different cell indexing subsequence.

In some embodiments, the plurality of the first partitions and the plurality of the second partitions can comprise different numbers of partitions. Two pluralities of partitions can comprise different numbers of partitions. Each of the pluralities of partitions can comprise different numbers of partitions. Two pluralities of partitions can comprise different numbers of partitions. The cell indexing sequence of the cell indexing oligonucleotide comprises n cell indexing subsequences. In some embodiments, n is an integer from 2 to 20. In some embodiments, n is at least about 1, 2, 3, 4, 5, 6, 7, 8, 9, 10, 11, 12, 13, 14, 15, 16, 17, 18, 19, or 20. The linker sequences can different lengths in different implementations. In some embodiments, a linker sequence is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or a number or a range between any two of these values, nucleotides in length. In some embodiments, a linker sequence is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, nucleotides in length. The cell indexing subsequences can different lengths in different implementations. In some embodiments, a cell indexing subsequence is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or a number or a range between any two of these values, nucleotides in length. In some embodiments, a cell indexing subsequence is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, nucleotides in length. The cell indexing oligonucleotides can have different lengths in different implementations. In some embodiments, a cell indexing oligonucleotide is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, a cell indexing oligonucleotide is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

A linker can comprise a chemical group (e.g., a UV photocleavable group, a streptavidin, a biotin, an amine, a disulfide linkage, or any combination thereof). A chemical group can be reversibly attached to the first indexing oligonucleotide. In some embodiments, the cellular component-binding reagent comprises a chemical group (e.g., a UV photocleavable group, a streptavidin, a biotin, an amine, a disulfide linkage, or any combination thereof). The linker can comprise a 5' amine. The linker can comprise a carbon chain (e.g., 2-30 carbons). A first indexing oligonucleotide can be covalently attached to the cellular component-binding reagent. A first indexing oligonucleotide can be conjugated to the cellular component-binding reagent. A first indexing oligonucleotide can be conjugated to the cellular component-binding reagent through a chemical group selected from the group consisting of a UV photocleavable group, a streptavidin, a biotin, an amine, and a combination thereof. The first indexing oligonucleotide can be non-covalently attached to the cellular component-binding reagent. In some embodiments, the first indexing oligonucleotide can be configured to be detachable from the cellular component-binding reagent. The cellular component binding reagent can comprise an antibody (e.g., immunoglobulin G (IgG), a F(ab') fragment, a F(ab')$_2$ fragment, a combination thereof, or a fragment thereof), a tetramer, an aptamer, a protein scaffold, or a combination thereof.

In some embodiments, each cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences. In some embodiments, each cell is associated with one or more unique cell indexing oligonucleotides, wherein the one or more unique cell indexing oligonucleotides associated with the same cell comprise the same cell indexing subsequences, and wherein the one or more unique cell indexing oligonucleotides associated with different cells comprise different cell indexing subsequences. The method can comprise determining the cell indexing sequences. The method can comprise determining one or more cell indexing subsequences according to the methods provided herein. In some embodiments, the cell indexing oligonucleotide is associated with a spatial index. The method can comprise determining the spatial index using n pluralities of probes as described herein. In some embodiments, determining the spatial index comprises sequentially hybridizing and imaging the n pluralities of probes annealing to the n cell indexing subsequences. The n pluralities of probes can comprise one or more detectable moieties, wherein imaging comprises detecting the one or more detectable moieties. The detectable moieties of the probes can comprise fluorescent labels, and sequential hybridization and imaging can comprise sequential hybridization and fluorescent imaging. The method can comprise determining the cell indexing sequence and/or cell indexing subsequences from the spatial index.

In some embodiments, the cell indexing oligonucleotide comprises two cell indexing subsequences, wherein the cell indexing subsequences anneal to different probes. In some embodiments, the method comprises partitioning the plurality of cells associated with one or more unique cell indexing oligonucleotides. In some embodiments, partitioning the plurality of cells associated with one or more unique cell indexing oligonucleotides comprises partitioning the plurality of cells associated with one or more unique cell indexing oligonucleotides to a plurality of partitions, wherein a partition of the plurality of partitions comprises the single cell from the plurality of cells associated with one or more unique cell indexing oligonucleotides. The method can comprise dissociating the cell indexing oligonucleotide from the cellular component-binding reagent. In some embodiments, dissociating the cell indexing oligonucleotide comprises detaching the cell indexing oligonucleotide from the cellular component-binding reagent by UV photocleaving, chemical treatment, heating, enzyme treatment, or any combination thereof. The dissociating can occur before or after stochastically labeling the cell indexing oligonucleotide. The dissociating can occur before or after stochastically labeling the cell indexing oligonucleotide.

In some embodiments, the first indexing oligonucleotide comprises a linker, and wherein the cellular component-binding reagent associates with the first indexing oligonucleotide via the linker. The first indexing oligonucleotide can be a single-stranded oligonucleotide. The first indexing oligonucleotide can be a double-stranded oligonucleotide. A linker strand of the first indexing oligonucleotide can comprise the linker. In some embodiments, a non-linker strand of the first indexing oligonucleotide does not comprises the linker, and wherein the non-linker strand is complementary to the linker strand. The 5' end of the linker strand can comprise the linker, and wherein the 5' end of the linker strand is proximal to the cellular component-binding reagent. The second indexing oligonucleotide can be a single-stranded oligonucleotide. The first indexing oligonucleotide can comprise a first linker sequence. The second indexing oligonucleotide can comprise a complementary sequence of the first linker sequence and a second linker sequence. Step (e) can comprise the first linker sequence of the first indexing oligonucleotide hybridizing to the complementary sequence of first linker sequence of the second indexing oligonucleotide, generating a hybridized indexing oligonucleotide. Step (e) can comprise extending the hybridized indexing oligonucleotide. Extending the hybridized indexing oligonucleotide can comprise extending the hybridized indexing oligonucleotide using a DNA polymerase (e.g., Klenow large fragment) and/or a reverse transcriptase. Extending the hybridized indexing oligonucleotide can generate a double-stranded indexing oligonucleotide comprising the first cell indexing subsequence and the second cell indexing subsequence. Step (e) further can comprise pooling the cells associated with the second cell indexing subsequence in each second partition of the plurality of second partitions and removing unbound second indexing oligonucleotides. Step (e) further can comprise removing the non-linker strand of the double-stranded indexing oligonucleotide. Removing the non-linker strand can comprise contacting the double-stranded indexing oligonucleotide with an enzyme with 5' to 3' exonuclease activity (e.g., Lamba exonuclease). The method can further comprise the step of (f): repeating steps (c)-(e) for q rounds, where q equals n−3, where q is a positive integer, wherein n is a positive integer greater than 3, and wherein each round of q rounds comprises distributing the pooled cells of step (e) into a plurality of nth partitions and associating the pooled cells in each nth partition of the plurality of nth partitions with an nth indexing oligonucleotide of a plurality of nth indexing oligonucleotides with an nth cell indexing subsequence, wherein the nth indexing oligonucleotides of the plurality of nth indexing oligonucleotides in two nth partitions of the plurality of nth partitions comprise different nth cell indexing subsequences, and wherein the nth indexing oligonucleotide comprises a complementary sequence of the nth−1 linker sequence and a nth linker sequence. The method can further comprise the step of (g): repeating steps (c)-(e) for a final round, wherein the final round comprises distributing the pooled cells of step (f) into a plurality of final partitions and associating the pooled cells in each final partition of the plurality of final partitions with a final indexing oligonucleotide of a plurality of final indexing oligonucleotides with an nth cell indexing subsequence, wherein the final indexing oligonucleotides of the plurality of final indexing oligonucleotides in two final partitions of the plurality of final partitions comprise different nth cell indexing subsequences, and wherein the final indexing oligonucleotide comprises an nth linker sequence and a target sequence. The nth indexing oligonucleotide can comprise a single-stranded oligonucleotide. The final indexing oligonucleotide can comprise a single-stranded oligonucleotide.

In some embodiments, the second indexing oligonucleotide is a double-stranded oligonucleotide. The second indexing oligonucleotide can comprise a first linker sequence and a second linker sequence. The first linker sequence can comprise a first restriction site and the second linker sequence can comprise a second restriction site. Step (e) can comprise contacting the first indexing oligonucleotide and the second indexing oligonucleotide with a first restriction enzyme, wherein first restriction enzyme recognizes and cleaves the first restriction site, wherein the restriction enzyme generates sticky ends, wherein the sticky ends of a cleaved first indexing oligonucleotide and a cleaved second indexing oligonucleotide hybridize to generate a hybridized indexing oligonucleotide. Step (e) can comprise contacting the hybridized indexing oligonucleotide with a ligase, thereby generating a double-stranded indexing oligonucleotide comprising the first cell indexing subsequence and the second cell indexing subsequence. Step (e) can comprise pooling the cells associated with the second cell indexing subsequence in each second partition of the plurality of second partitions and removing unbound second indexing oligonucleotides. The method can comprise the step of (f): repeating steps (c)-(e) for q rounds, where q equals n−3, where q is a positive integer, wherein n is a positive integer greater than 3, and wherein each round of q rounds comprises distributing the pooled cells of step (e) into a plurality of nth partitions and associating the pooled cells in each nth partition of the plurality of nth partitions with an nth indexing oligonucleotide of a plurality of nth indexing oligonucleotides with an nth cell indexing subsequence, wherein the nth indexing oligonucleotides of the plurality of nth indexing oligonucleotides in two nth partitions of the plurality of nth partitions comprise different nth cell indexing subsequences, and wherein the nth indexing oligonucleotide comprises an nth−1 linker sequence and a nth linker sequence. The method can comprise the step of (g): repeating steps (c)-(e) for a final round, wherein the final round comprises distributing the pooled cells of step (f) into a plurality of final partitions and associating the pooled cells in each final partition of the plurality of final partitions with a final indexing oligonucleotide of a plurality of final indexing oligonucleotides with an nth cell indexing subsequence, wherein the final indexing oligonucleotides of the plurality of final indexing oligonucleotides in two final partitions of the plurality of final partitions comprise different nth cell indexing subsequences, and wherein the final indexing oligonucleotide comprises an nth linker sequence and a target sequence. The nth indexing oligonucleotide can comprise a double-stranded oligonucleotide. The final indexing oligonucleotide can comprise a double-stranded oligonucleotide. The nth linker sequence can comprise an nth restriction site recognized by an nth restriction enzyme, and wherein the n restriction sites comprise different restriction sites. The first restriction enzyme can recognize the first restriction site in the first linker and the final restriction enzyme can recognize a restriction site in nth linker sequence. The nth linker sequence can comprise an nth restriction site recognized by an nth restriction enzyme, and wherein different linker sequences comprise different restriction sites. The plurality of the first partitions can comprise p partitions, and wherein the plurality of second partitions comprises p partitions, and wherein p is positive integer. wherein each plurality of nth partitions can comprise p partitions. The plurality of final partitions can comprise p partitions. Cell indexing oligonucleotides can be comprised of any type of nucleic acid (e.g., PNA, LNA).

Cell indexing oligonucleotides can be attached to a solid or semi-support (e.g., a bead, a gel particle, an antibody, a hydrogel, agarose). Cell indexing oligonucleotides can be immobilized on a substrate of the disclosure (e.g., an array).

Cell indexing oligonucleotides can be incorporated into a biological package, such as a virus, a liposome, a microsphere, etc. In some embodiments, each of a plurality of synthetic particles has a unique cell indexing oligonucleotide. Each synthetic particle can be associated with one or more unique cell indexing oligonucleotides, wherein the one or more unique cell indexing oligonucleotides associated with the same synthetic particle comprise the same cell indexing subsequences, and wherein the one or more unique cell indexing oligonucleotides associated with different synthetic particles comprise different cell indexing subsequences. For example, the plurality of synthetic particles can include, include about, or include more than 1, 2, 3, 4, 5, 6, 7, 8, 9, 10, 100, 200, 300, 400, 500, 600, 700, 800, 900, $10^3$, $10^4$, $10^5$, $10^6$, $10^7$, $10^8$, $10^9$, $10^{10}$, $10^{11}$, $10^{12}$, or a number or a range between any two of these values, synthetic particles each with a unique cell indexing oligonucleotide and/or cell indexing sequence. In some embodiments, the synthetic particles comprise a plurality of stochastic labels. The stochastic labels can comprise the cell indexing sequence. A stochastic label can comprise a cellular label. In some embodiments, the cellular label comprises the cell indexing sequence.

A cell indexing oligonucleotides can be synthesized on a solid support (e.g., bead). Pre-synthesized cell indexing oligonucleotides (e.g., comprising the 5'amine that can link to the solid support) may be attached to solid supports (e.g., beads) through any of a variety of immobilization techniques involving functional group pairs on the solid support and the cell indexing oligonucleotide. The cell indexing oligonucleotide can comprise a functional group. The solid support (e.g., bead) can comprise a functional group. The cell indexing oligonucleotide functional group and the solid support functional group can comprise, for example, biotin, streptavidin, primary amine(s), carboxyl(s), hydroxyl(s), aldehyde(s), ketone(s), and any combination thereof. A cell indexing oligonucleotide may be tethered to a solid support, for example, by coupling (e.g. using 1-Ethyl-3-(3-dimethylaminopropyl) carbodiimide) a 5' amino group on the cell indexing oligonucleotide to the carboxyl group of the functionalized solid support. Residual non-coupled cell indexing oligonucleotides may be removed from the reaction mixture by performing multiple rinse steps. In some embodiments, the cell indexing oligonucleotide and solid support are attached indirectly via linker molecules (e.g. short, functionalized hydrocarbon molecules or polyethylene oxide molecules) using similar attachment chemistries. The linkers may be cleavable linkers, e.g. acid-labile linkers or photocleavable linkers.

The number of cell indexing oligonucleotides with different cell indexing sequences can be different in different implementations. In some embodiments, the number of cell indexing sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell indexing sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles (e.g., cells, synthetic particles) are associated with oligonucleotides with the same cell indexing sequence. In some embodiment, the plurality of particles (e.g., cells, synthetic particles) that include oligonucleotides with the same cell indexing sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell indexing sequence.

Figure 8:
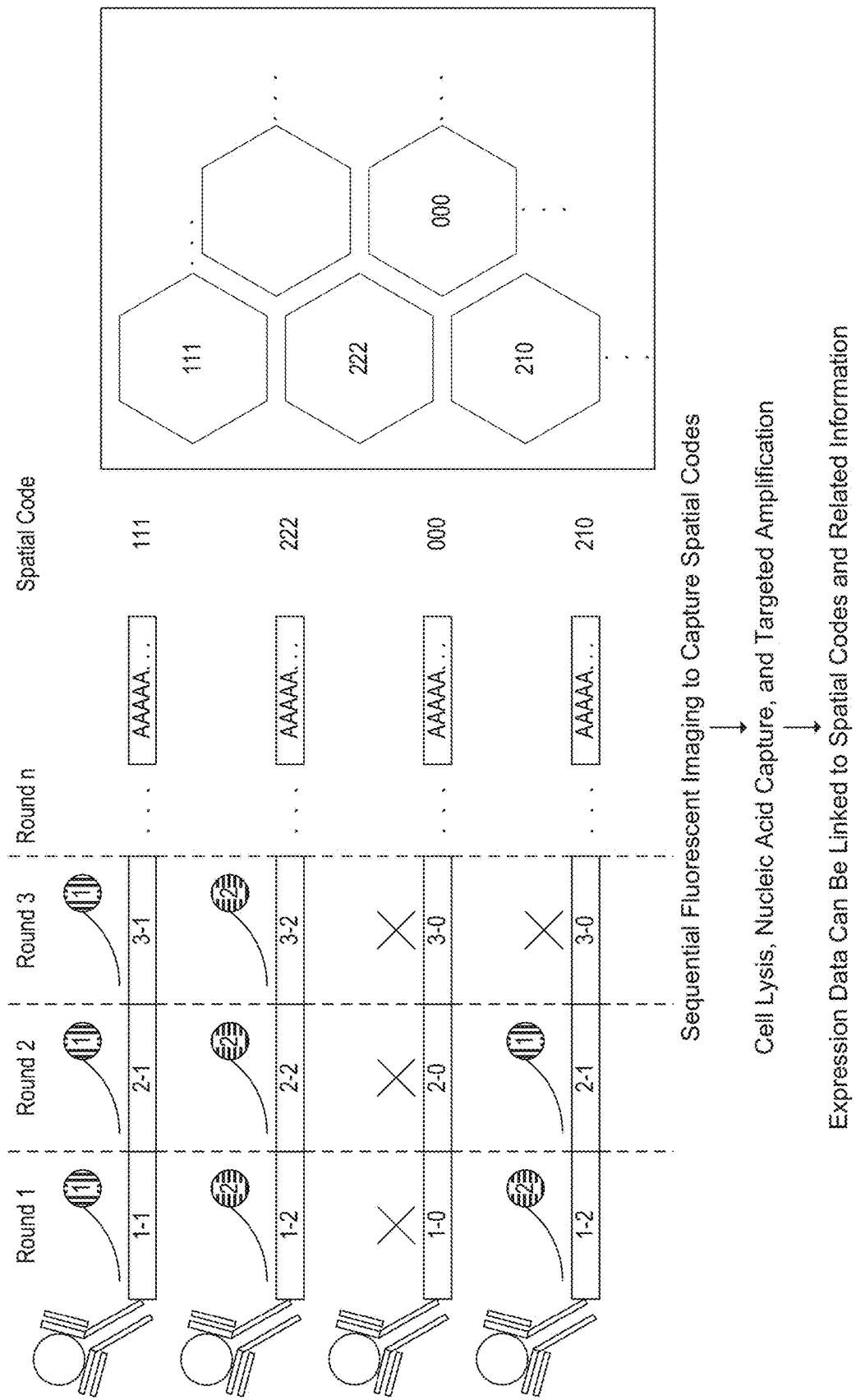
FIG. 8 shows a schematic illustration of a non-limiting exemplary method for generating a spatial index associated with a cell indexing oligonucleotide.

Methods of Generating a Spatial Index Associated with a Cell Indexing Oligonucleotide and/or Cell Indexing Sequence There are provided, in some embodiments, methods of a generating a spatial index associated with a cell indexing oligonucleotide and/or cell indexing sequence disclosed herein. FIG. 8 shows a schematic illustration of a non-limiting exemplary method for generating a spatial index associated with a cell indexing oligonucleotide. Each cell can be associated with one or more unique cell indexing oligonucleotides comprising n cell indexing subsequences. The one or more unique cell indexing oligonucleotides associated with the same cell can comprise the same cell indexing subsequences (e.g., the same cell indexing sequence), and the one or more unique cell indexing oligonucleotides associated with different cells can comprise different cell indexing subsequences (e.g., different cell indexing sequences). Cells can be associated with the cell indexing oligonucleotides via a cellular component-binding reagent (antibody illustrated here). Each cell can be partitioned to a plurality of partitions (e.g., microwells of a microwell array). Each partition can comprise a single cell. The spatial index associated with each cell indexing oligonucleotide of each cell within each partition can be elucidated by the methods provided herein. In some embodiments, determining the spatial index comprises sequentially hybridizing and imaging the n pluralities of probes annealing to the n cell indexing subsequences. The n pluralities of probes can comprise one or more detectable moieties, wherein imaging comprises detecting the one or more detectable moieties. The detectable moieties of the probes can comprise fluorescent labels, and sequential hybridization and imaging can comprise sequential hybridization and fluorescent imaging. Hybridization of probes and imaging can be repeated for a total of n rounds for each of the n cell indexing subsequences. Annealed probes and/or the detectable moieties thereof can be removed after each round (not shown here for sake of clarity). The absence of signal during an imaging step can be due to the absence of annealing of a probe to a cell indexing subsequence (as illustrated here) or due to annealing of a probe that does not comprise a detectable moiety, and is registered as a "0" with regards to the spatial index. For example, the first cell indexing subsequence (1-1), second cell indexing subsequence (2-1), and third cell indexing subsequence (3-1) of the first cell indexing oligonucleotide depicted (top) are shown being annealed by probes comprising a $1^{st}$ detectable moiety during each of first, second, and third rounds of sequential hybridization and imaging, respectively, generating a spatial index of "111." This spatial index of 111 is associated with the partition in which the cell and cell indexing oligonucleotide reside, thereby indicating the position of the cell and cell indexing oligonucleotide within the plurality of partitions. The method can be multiplexed and the spatial index of a plurality of cell indexing oligonucleotides can be generated (e.g., the other three cell indexing oligonucleotides depicted).

FIG. 8 also depicts a non-limiting exemplary workflow of using a spatial index to associate sequencing data with phenotypic data. Following sequential hybridization and imaging (e.g., sequential fluorescent imaging) to capture spatial indices (and thereby elucidate the cell indexing sequence), cells can be lysed, liberating nucleic acid target molecules. Nucleic acid target molecules can be captured by stochastic labels comprising a unique partition label (e.g., cellular label), amplified, and sequenced. The spatial location of each nucleic acid target molecule (e.g., the identity of the partition from which the nucleic acid target molecule originated) can be determined by associating the cellular label of the partition and the cell indexing sequence of the partition. Sequencing data (e.g., expression data) can thereby be associated with the spatial index (and its corresponding cell indexing sequence) and related partition information (e.g., phenotypic data, agent exposure).

Figure 9A:
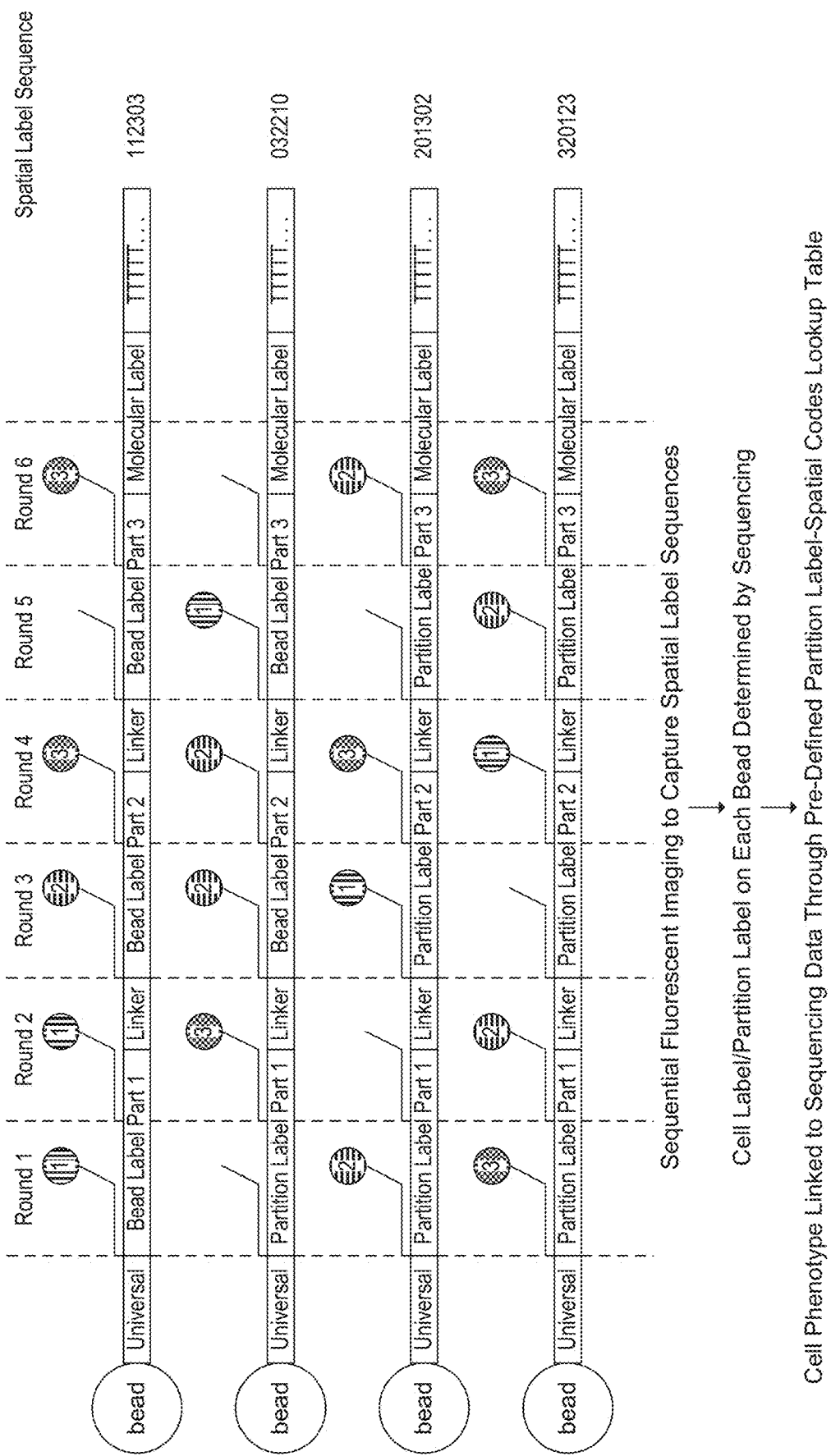
FIG. 9A shows a schematic illustration of a non-limiting exemplary method for generating a spatial index associated with a synthetic particle.

FIG. 9A shows a schematic illustration of a non-limiting exemplary method for generating a spatial index associated with a synthetic particle (bead illustrated here). Each bead can be associated with one or more unique cell indexing sequences comprising n cell indexing subsequences (6 cell indexing subsequences illustrated here). The one or more unique cell indexing sequences associated with the same bead can comprise the same cell indexing subsequences (e.g., the same cell indexing sequence), and the one or more unique cell indexing oligonucleotides associated with different beads can comprise different cell indexing subsequences (e.g., different cell indexing sequences). Each bead can be associated with one or more stochastic labels. Stochastic labels can comprise, for example, universal sequences, partition labels, molecular labels, and a capture sequence (e.g. a poly(dT) region). Each bead can be associated with one or more unique partition labels (e.g., cellular label). The one or more unique partition labels associated with the same bead can comprise the same sequences (e.g., the same cellular label), and the one or more unique partition labels associated with different beads can comprise different sequences (e.g., different cellular labels). Stochastic labels can comprise the cell indexing sequence. Partition labels can comprise two or parts. One or more linkers can separate the two or more parts of partition labels. In some embodiments, a partition label comprising three parts is provided (as illustrated here). Partition labels (e.g., cellular labels) can comprise the cell indexing sequence. Each part of a partition label can comprise one or more cell indexing subsequences. In some embodiments, each part of a partition label comprises two cell indexing subsequences (as illustrated here). For example, the partition label part 1 can comprise the first and second cell indexing subsequences, partition label part 2 can comprise the third and fourth cell indexing subsequences, and partition label part 3 can comprise the fifth and sixth cell indexing subsequences (as illustrated here). Each bead can be partitioned to a plurality of partitions (e.g., microwells of a microwell array). Each partition can comprise a single bead. The spatial index associated with each bead within each partition can be elucidated by the methods provided herein. In some embodiments, determining the spatial index comprises sequentially hybridizing and imaging the n pluralities of probes annealing to the n cell indexing subsequences (e.g., situated within the partition label). The n pluralities of probes can comprise one or more detectable moieties, wherein imaging comprises detecting the one or more detectable moieties. The detectable moieties of the probes can comprise fluorescent labels, and sequential hybridization and imaging can comprise sequential hybridization and fluorescent imaging. Hybridization of probes and imaging can be repeated for a total of n rounds for each of the n cell indexing subsequences (six rounds illustrated here). Annealed probes and/or the detectable moieties thereof can be removed after each round (not shown here for sake of clarity). The absence of signal during an imaging step can be due to annealing of a probe that does not comprise a detectable moiety (as illustrated here) or due to the absence of annealing of a probe to a cell indexing subsequence, and is registered as a "0" with regards to the spatial index. For example, with regards to first bead depicted (top), the first and second cell indexing subsequences of the are annealed by a probe comprising a $1^{st}$ detectable moiety, the third cell indexing subsequence is annealed by a probe comprising a $2^{nd}$ detectable moiety, the fourth cell indexing subsequence is annealed by a probe comprising a $3^{nd}$ detectable moiety, the fifth cell indexing subsequence is annealed by a probe not comprising a detectable moiety, and the sixth cell indexing subsequence is annealed by a probe comprising a $3^{nd}$ detectable moiety during each of first through sixth rounds of sequential hybridization and imaging, respectively, generating a spatial index of "112303." This spatial index of 112303 is associated with the partition in which the bead and partition label reside, thereby indicating the position of the bead and partition label within the plurality of partitions. The method can be multiplexed and the spatial index associated each partitioned bead can be elucidated (e.g., the other three beads depicted).

FIG. 9A also depicts a non-limiting exemplary workflow of using a spatial index to associate sequencing data with phenotypic data. Following sequential hybridization and imaging (e.g., sequential fluorescent imaging) of beads to capture spatial indices (and thereby elucidate the cell indexing sequence and/or partition label), single cells can be partitioned with the single beads and the cells can be lysed, liberating nucleic acid target molecules. Nucleic acid target molecules can be captured by the stochastic labels of beads comprising a unique partition label (e.g., cellular label), amplified, and sequenced. The spatial location of each nucleic acid target molecule (e.g., the identity of the partition from which the nucleic acid target molecule originated) can be determined by associating with the partition label and/or cell indexing sequence of the partition. Sequencing data (e.g., expression data) can thereby be associated with the spatial index (and its corresponding cell indexing sequence and partition label) and related partition information (e.g., phenotypic data, agent exposure).

Disclosed herein include methods for generating a spatial index. In some embodiments, the method comprises: (a) contacting a cell indexing oligonucleotide with a plurality of first probes, wherein one or more of the probes of the plurality of first probes comprise a detectable moiety, or precursor thereof, wherein the cell indexing oligonucleotide comprises a series of n cell indexing subsequences, wherein n is an integer greater than 1, and wherein probes selectively anneal to cell indexing subsequences with complementary sequences; (b) removing unannealed probes; (c) imaging the cell indexing oligonucleotide, wherein imaging comprises detecting a signal of the detectable moiety; (d) removing the annealed probes and/or the detectable moieties thereof; and (e) repeating the steps (a)-(d) for a total of n cycles, wherein each nth cycle comprises contacting a plurality of nth probes with the cell indexing oligonucleotide, whereby a spatial index is generated for the cell indexing oligonucleotide, wherein the spatial index comprises a series of n signals and/or absence of signals detected in the n cycles. In some embodiments, each nth cell indexing subsequence of the series of n cell indexing subsequences is selected from p unique cell indexing subsequences, wherein p is an integer greater than 1. The cell indexing oligonucleotide can comprise a cell indexing sequence, wherein the cell indexing sequence of the cell indexing oligonucleotide comprises the n cell indexing subsequences.

During each nth cycle a plurality of nth probes selectively anneal to the nth position of the series of n cell indexing subsequences. In some embodiments, n is at least about 1, 2, 3, 4, 5, 6, 7, 8, 9, 10, 11, 12, 13, 14, 15, 16, 17, 18, 19, or 20. In some embodiments, each plurality of nth probes comprises p unique probes, wherein unique probes selectively anneal to different cell indexing subsequences, and wherein p is an integer greater than 1. In some embodiments, m probes of the p unique probes comprise a detectable moiety, or precursor thereof, wherein m is an integer greater than 1, and wherein m is p−1. In some embodiments, m is at least about 1, 2, 3, 4, 5, 6, 7, 8, 9, 10, 11, 12, 13, 14, 15, 16, 17, 18, 19, or 20. In some embodiments, the absence of signal during an imaging step is due to annealing of a probe that does not comprise a detectable moiety. Each plurality of nth probes can comprise m unique probes, wherein unique probes selectively anneal to different cell indexing subsequences, wherein m is an integer greater than 1, and wherein m is p−1. In some embodiments, p is at least about 1, 2, 3, 4, 5, 6, 7, 8, 9, 10, 11, 12, 13, 14, 15, 16, 17, 18, 19, or 20. The m unique probes can comprise a detectable moiety, or precursor thereof. In some embodiments, during each cycle of the n cycles, one unique cell indexing subsequence of the p unique cell indexing subsequences is not annealed by a probe. The absence of signal during an imaging step can be due the absence of annealing of a probe to a cell indexing subsequence. A cell indexing sequence can comprise n cell indexing subsequences, wherein n is an integer greater than 1, wherein each cell indexing subsequence is selected from p unique cell indexing subsequences, wherein p is an integer greater than 1, wherein two unique cell indexing oligonucleotides comprise different cell indexing sequences.

In some embodiments, the cell indexing oligonucleotide can be associated with a synthetic particle. The synthetic particle can comprise a plurality of stochastic labels, wherein the stochastic labels are oligonucleotides, and wherein a stochastic label comprises the cell indexing oligonucleotide. The synthetic particle can comprise a plurality of stochastic labels, wherein the stochastic labels are oligonucleotides, and wherein a stochastic label comprises the cell indexing sequence. The stochastic label can comprise a cellular label. The cellular label can comprise the cell indexing sequence. In some embodiments, a unique cell indexing subsequence occurs at only one position within the series of n cell indexing subsequences. Two unique cell indexing subsequences can anneal to different probes. The series of n cell indexing subsequences can be linked in a tandem manner. The series of n cell indexing subsequences can comprise one or more linker sequences separating two or more cell indexing subsequences.

In some embodiments, the total number of unique probes is n*p. In some embodiments, the total number of unique probes is n*m. In some embodiments, the total number of unique cell indexing subsequences is n*p. In some embodiments, the cell indexing oligonucleotide can be single-stranded. The method can comprise rendering the cell indexing oligonucleotide single-stranded prior to contacting with the first plurality of probes. Imaging can comprise optical microscopy, fluorescence microscopy, confocal microscopy, electron microscopy, or any combination thereof. Removing the unannealed probes can comprise washing the cell indexing oligonucleotide with a washing buffer. Selective annealing is performed under stringent hybridization conditions (e.g., conditions that allow annealing to occur if sequence complementary is greater than 90%). The probes can comprise a sequence complementary to a cell indexing subsequence. The length of the probe can be at least 1, 2, 3, 4, 5, 6, 7, 8, 9, 10, 11, 12, 13, 14, or 15 or more nucleotides. The length of the probe can be at most 1, 2, 3, 4, 5, 6, 7, 8, 9, 10, 11, 12, 13, 14, or 15 or more nucleotides. The probes can comprise a sequence that is perfectly complementary to a cell indexing subsequence. The probes can comprise a sequence that is imperfectly complementary to a cell indexing subsequence. The detection can comprise a sequence with at least 1, 2, 3, 4, 5, 6, 7, 8, 9, or 10 or more mismatches to a cell indexing subsequence. The probes can comprise a sequence with at most 1, 2, 3, 4, 5, 6, 7, 8, 9, or 10 or more mismatches to a cell indexing subsequence.

In some embodiments, the ratio cell indexing oligonucleotide to probe ranges from 1:100 to 100:1. In some embodiments, the ratio of cell indexing oligonucleotide to probe is at most 10:1. In some embodiments, the ratio of cell indexing oligonucleotide to probe is at most 100:1. In some embodiments, the ratio of cell indexing oligonucleotide to probe is at most 1:1000. In some embodiments, the ratio of cell indexing oligonucleotide to probe is at least 1:10. In some embodiments, the ratio of cell indexing oligonucleotide to probe is at least 1:100. In some embodiments, the ratio of cell indexing oligonucleotide to probe is at least 1:1000.

In some embodiments, the ratio of cell indexing oligonucleotide to probe can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio of cell indexing oligonucleotide to probe can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

In some embodiments, the sequence of each probe is known, the detectable moiety of each probe is known, the identity of the series of n cell indexing subsequences is not known, and the selective annealing of an nth probe to the nth cell indexing subsequence of the series of n cell indexing subsequences identifies the nth cell indexing subsequence. In some embodiments, the identity of the n cell indexing subsequences is unknown before the method is performed. In some embodiments, the identity of the n cell indexing subsequences is unknown prior to placement of the cell indexing oligonucleotide in a partition. In some embodiments, generating the spatial index of the cell indexing oligonucleotide enables a determination of the n cell indexing subsequences of the cell indexing oligonucleotide. In some embodiments, generating the spatial index of the cell indexing oligonucleotide enables a determination of the cell indexing sequence of the cell indexing oligonucleotide.

In some embodiments, the detectable moiety, or precursor thereof, of the m probes is selected from a set of m spectrally distinct moieties. The set of m spectrally distinct moieties can be identical for each plurality of probes. The probe can comprise an oligonucleotide. The oligonucleotide can comprise a DNA, a RNA, a morpholino, a locked nucleic acid (LNA), a peptide nucleic acid (PNA), a DNA, an LNA/PNA chimera, an LNA/DNA chimera, a PNA/DNA chimera, or any combination thereof. The m probes can comprise a single detectable moiety, or precursor thereof. In some embodiments, the single detectable moieties of each of the m probes are spectrally-distinct detectable moieties. The m probes each can comprise a plurality of detectable moieties, or precursors thereof. The m probes can comprise a first detectable moiety and second detectable moiety, and wherein the first detectable moiety and the second detectable moiety are selected from a group comprising two or more spectrally-distinct detectable moieties. The detectable moiety can comprise an optical moiety, a luminescent moiety, an electrochemically active moiety, a nanoparticle (e.g., a quantum dot), or a combination thereof. The luminescent moiety can comprise a chemiluminescent moiety, an electroluminescent moiety, a photoluminescent moiety, or a combination thereof. The photoluminescent moiety can comprise a fluorescent moiety (e.g., a fluorescent dye), a phosphorescent moiety, or a combination thereof.

The detectable moiety can be selected from a group of spectrally-distinct detectable moieties. Spectrally-distinct detectable moieties include detectable moieties with distinguishable emission spectra even if their emission spectral may overlap. Non-limiting examples of detectable moieties include Xanthene derivatives: fluorescein, rhodamine, Oregon green, eosin, and Texas red; Cyanine derivatives: cyanine, indocarbocyanine, oxacarbocyanine, thiacarbocyanine, and merocyanine; Squaraine derivatives and ring-substituted squaraines, including Seta, SeTau, and Square dyes; Naphthalene derivatives (dansyl and prodan derivatives); Coumarin derivatives; oxadiazole derivatives: pyridyloxazole, nitrobenzoxadiazole and benzoxadiazole; Anthracene derivatives: anthraquinones, including DRAQ5, DRAQ7 and CyTRAK Orange; Pyrene derivatives: cascade blue; Oxazine derivatives: Nile red, Nile blue, cresyl violet, oxazine 170; Acridine derivatives: proflavin, acridine orange, acridine yellow; Arylmethine derivatives: auramine, crystal violet, malachite green; and Tetrapyrrole derivatives: porphin, phthalocyanine, bilirubin. Other non-limiting examples of detectable moieties include Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, CyTRAK Orange, Propidium Iodide (PI), LDS 751, 7-AAD, SYTOX Orange, TOTO-3, TO-PRO-3, DRAQ5, DRAQ7, Indo-1, Fluo-3, Fluo-4, DCFH, DHR, and SNARF.

The excitation wavelength of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values. The emission wavelength of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values.

The molecular weights of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 Daltons (Da), or a number or a range between any two of these values. The molecular weights of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 kilo Daltons (kDa), or a number or a range between any two of these values.

The group of spectrally distinct detectable moieties can, for example, include five different fluorophores, five different chromophores, a combination of five fluorophores and chromophores, a combination of four different fluorophores and a non-fluorophore, a combination of four chromophores and a non-chromophore, or a combination of four fluorophores and chromophores and a non-fluorophore non-chromophore. In some embodiments, the detectable moieties can be one of 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of spectrally-distinct moieties.

As discussed above, probes may include detectable moieties or markers that are detectible based on, for example, fluorescence emission, absorbance, fluorescence polarization, fluorescence lifetime, fluorescence wavelength, absorbance wavelength, Stokes shift, light scatter, mass, molecular mass, redox, acoustic, Raman, magnetism, radio frequency, enzymatic reactions (including chemiluminescence and electro-chemiluminescence) or combinations thereof. For example, the detectable moiety may be a fluorophore, a chromophore, an enzyme, an enzyme substrate, a catalyst, a redox label, a radio label, an acoustic label, a Raman (SERS) tag, a mass tag, an isotope tag (e.g., isotopically pure rare earth element), a magnetic particle, a microparticle, a nanoparticle, an oligonucleotide, or any combination thereof. In some embodiments, the detectable moiety is a fluorophore (i.e., a fluorescent label, fluorescent dye, etc.). Fluorophores of interest may include but are not limited to dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more of the aforementioned dyes (e.g., in tandem), polymeric dyes having one or more monomeric dye units and mixtures of two or more of the aforementioned dyes thereof. A large number of dyes are commercially available from a variety of sources, such as, for example, Molecular Probes (Eugene, OR), Dyomics GmbH (Jena, Germany), Sigma-Aldrich (St. Louis, MO), Sirigen, Inc. (Santa Barbara, CA) and Exciton (Dayton, OH). For example, the fluorophore may include 4-acetamido-4'-isothiocyanatostilbene-2,2'disulfonic acid; acridine and derivatives such as acridine, acridine orange, acridine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4- trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more dyes (e.g., in tandem), polymeric dyes having one or more monomeric dye units and mixtures of two or more of the aforementioned dyes or combinations thereof.

The method can comprise performing a reaction to convert the detectable moiety precursor into the detectable moiety. Removing the annealed probes and/or the detectable moieties thereof can comprise removing the detectable moiety. Removing the detectable moiety can comprise photobleaching. The detectable moiety can be attached to the probe via a linker. The linker can comprise a restriction site, and removing the detectable moiety can comprise addition of a restriction enzyme. In some embodiments, the detectable moiety and the probe are connected through a cleavable linkage (e.g., a chemically cleavable linkage, a photocleavable linkage, an acid labile linker, a heat sensitive linkage, an enzymatically cleavable linkage, or any combination thereof). Removing the annealed probes and/or the detectable moieties thereof can comprise removing the annealed probe. Removing the annealed probe can comprise heating. Removing the annealed probe can comprise the addition an exonuclease. In some embodiments, the exonuclease comprises 3' to 5' exonuclease activity and wherein the 5' end of the cell indexing oligonucleotide is associated with a synthetic particle or a cellular component-binding reagent. In some embodiments, the exonuclease comprises 5' to 3' exonuclease activity and wherein the 3' end of the cell indexing oligonucleotide is associated with a synthetic particle or a cellular component-binding reagent.

In some embodiments, the number of unique spatial indices that can be generated is equal to or less than $(1+m)^n$. In some embodiments, p is an integer from 2 to 15. In some embodiments, m is an integer from 2 to 15. In some embodiments, n is an integer from 2 to 15. In some embodiments, n is 4, and m is 9 or 10. In some embodiments, n is 5, and m is 6, 7, 8, 9 or 10. In some embodiments, n is 6, and m is 4, 5, 6, 7, 8, or 9. In some embodiments, n is 7, and m is 3, 4, 5, 6, or 7. In some embodiments, n is 8, and m is 3, 4, or 5. In some embodiments, n is 9, and m is 2, 3, or 4. In some embodiments, n is 10, and m is 2 or 3. In some embodiments, p is m+1. The number of cell indexing oligonucleotides with different spatial indices can be different in different implementations. In some embodiments, the number of spatial indices can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of spatial indices can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles (e.g., cells, synthetic particles) are associated with cell indexing oligonucleotides with the same spatial index. In some embodiment, the plurality of particles (e.g., cells, synthetic particles) that include oligonucleotides with the same spatial index can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same spatial index.

In some embodiments, the methods of generating a spatial index disclosed herein can be multiplexed. The method can comprise generating a spatial index of a plurality of unique cell indexing oligonucleotides. In some embodiments, each unique cell indexing oligonucleotide of the plurality of unique cell indexing oligonucleotides is contacted with probes in spatial isolation from the other unique cell indexing oligonucleotides. The method can comprise, prior to step (a), partitioning a plurality of unique cell indexing oligonucleotides to a plurality of partitions (e.g., microwells of a microwell array, a plurality of droplets), wherein a partition of the plurality of partitions comprises one or more copies of a single unique cell indexing oligonucleotide. In some embodiments, the cell indexing sequences of unique cell indexing oligonucleotides are different. In some embodiments, spatial indices of unique cell indexing oligonucleotides are different. The method can comprise generating a spatial index of at least 96 unique cell indexing oligonucleotides. The method can comprise generating a spatial index of at least 1,000 unique cell indexing oligonucleotides. The method can comprise generating a spatial index of at least 10,000 unique cell indexing oligonucleotides. In some embodiments, the plurality of partitions are imaged sequentially and/or simultaneously.

Hybridized probes can be imaged. The image can be used to determine the presence or absence of annealing of a probe to a cell indexing subsequence based on the detectable signal (e.g., fluorescent signal). The plurality of partitions can be imaged (e.g., with a confocal laser scanner). The scanner can scan the plurality of partitions to produce one image for each detectable moiety used by sequentially scanning the partitions with a laser of a proper wavelength for the particular detectable moiety. Each detectable moiety can have a known excitation spectra and a known emission spectra. The scanner can include a beam splitter which reflects a laser beam towards an objective lens which, in turn, focuses the beam at the surface of the plurality of partitions to cause fluorescence spherical emission. A portion of the emission can travel back through the lens and the beam splitter. After traveling through the beam splitter, the fluorescence beam can be reflected by a mirror, travels through an emission filter, a focusing detector lens and a central pinhole. Imaging can comprise microscopy such as bright field imaging, oblique illumination, dark field imaging, dispersion staining, phase contrast, differential interference contrast, interference reflection microscopy, fluorescence, confocal, electron microscopy, transmission electron microscopy, scanning electron microscopy, and single plane illumination, or any combination thereof.

In some embodiments, a unique cell indexing oligonucleotide is associated with a particle. In some embodiments, the particle is a cell. In some embodiments, the particle is a synthetic particle (e.g., a bead, silica gel beads, controlled pore glass beads, magnetic beads, Dynabeads, Sephadex/Sepharose beads, cellulose beads, polystyrene beads, or any combination thereof). Two or more partitions of the plurality of partitions can comprise a single cell. Two or more partitions of the plurality of partitions can comprise a single bead. In some embodiments, the single cell is associated with one or more unique cell indexing oligonucleotides, wherein the one or more cell indexing oligonucleotides associated with the same cell comprise the same cell indexing sequence, and wherein the one or more cell indexing oligonucleotides associated with cells in different partitions comprise different cell indexing sequences. In some embodiments, the single bead is associated with one or more unique cell indexing oligonucleotides, wherein the one or more cell indexing oligonucleotides associated with the single bead comprise the same cell indexing sequence, and wherein the one or more cell indexing oligonucleotides associated with beads in different partitions comprise different cell indexing sequences. Two or more partitions of the plurality of partitions can comprise a single bead and a single cell, wherein the single bead is associated with one or more unique cell indexing oligonucleotides, wherein the one or more cell indexing oligonucleotides associated with the single bead comprise the same cell indexing sequence, and wherein the one or more cell indexing oligonucleotides associated with beads in different partitions comprise different cell indexing sequences. Two or more partitions of the plurality of partitions can comprise a single bead and a single cell, wherein the single cell is associated with one or more unique cell indexing oligonucleotides, wherein the one or more cell indexing oligonucleotides associated with the same cell comprise the same cell indexing sequence, and wherein the one or more cell indexing oligonucleotides associated with cells in different partitions comprise different cell indexing sequences.

Methods of Associating Sequencing Data with Phenotypic Data and/or Agent Exposure Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (c) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (d) determining the spatial location of each nucleic acid target molecule by associating the cellular label of the partition and the cell indexing sequence of the partition, wherein the spatial location comprises the identity of the partition from which the nucleic acid target molecule originated. In some embodiments, the method comprises: i) generating the spatial index of the unique cell indexing oligonucleotide of each partition to identify the spatial index of each partition; and ii) determining the cell indexing sequence of each partition based on the spatial index of each partition.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) obtaining phenotypic data for each single cell; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the phenotypic data and the sequencing data of each single cell by associating the cellular label of the partition and the cell indexing sequence for each nucleic acid target molecule. In some embodiments, the method comprises: i) generating the spatial index of the unique cell indexing oligonucleotide of each partition to identify the spatial index of each partition; and ii) determining the cell indexing sequence of each partition based on the spatial index of each partition.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell, wherein each single cell is associated with one or more unique cell indexing oligonucleotides, wherein the one or more unique cell indexing oligonucleotides associated with the same cell comprise the same cell indexing sequence, and wherein the one or more unique cell indexing oligonucleotides associated with different cells comprise different cell indexing sequences, and wherein each cell of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the agent exposure and the sequencing data of each single cell by associating the cellular label of the partition and the cell indexing sequence for each nucleic acid target molecule. In some embodiments, the method comprises: i) obtaining phenotypic data for each single cell; and ii) associating the phenotypic data and the sequencing data of each single cell based on the cell indexing sequence. In some embodiments, the method comprises: i) generating the spatial index of the unique cell indexing oligonucleotide of each partition to identify the spatial index of each partition; and ii) determining the cell indexing sequence of each partition based on the spatial index of each partition.

Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell and a single synthetic particle, wherein each single synthetic particle is associated with one or more unique cell indexing oligonucleotides, wherein the one or more unique cell indexing oligonucleotides associated with the same synthetic particle comprise the same cell indexing sequence, and wherein the one or more unique cell indexing oligonucleotides associated with different synthetic particles comprise different cell indexing sequences, and wherein each of the plurality of single cells comprises a plurality of nucleic acid target molecules; (b) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (c) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (d) determining the spatial location of each nucleic acid target molecule by associating the cellular label of the partition and the cell indexing sequence of the partition, wherein the spatial location comprises the identity of the partition from which the nucleic acid target molecule originated. In some embodiments, the method comprises: i) generating the spatial index of the unique cell indexing oligonucleotide of each partition to identify the spatial index of each partition; and ii) determining the cell indexing sequence of each partition based on the spatial index of each partition.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each single synthetic particle is associated with one or more unique cell indexing oligonucleotides, wherein the one or more unique cell indexing oligonucleotides associated with the same synthetic particle comprise the same cell indexing sequence, and wherein the one or more unique cell indexing oligonucleotides associated with different synthetic particles comprise different cell indexing sequences, and wherein each of the plurality of single cells comprises a plurality of nucleic acid target molecules; (b) obtaining phenotypic data for each single cell; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the phenotypic data and the sequencing data of each single cell based on the cell indexing sequence. In some embodiments, the method comprises: i) generating the spatial index of the unique cell indexing oligonucleotide of each partition to identify the spatial index of each partition; and ii) determining the cell indexing sequence of each partition based on the spatial index of each partition.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each single synthetic particle is associated with one or more unique cell indexing oligonucleotides, wherein the one or more unique cell indexing oligonucleotides associated with the same synthetic particle comprise the same cell indexing sequence, and wherein the one or more unique cell indexing oligonucleotides associated with different synthetic particles comprise different cell indexing sequences, and wherein each of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the cell indexing oligonucleotides and nucleic acid target molecules using a plurality of stochastic labels to generate a plurality of stochastically labeled cell indexing oligonucleotides and a plurality of stochastically labeled nucleic acid target molecules, wherein the stochastic labels comprise a cellular label, wherein the stochastic labels associated with the same cell comprise the same cellular label, and wherein the cellular labels associated with different cells comprise different cellular labels; (d) obtaining the sequencing data of the plurality of stochastically labeled cell indexing oligonucleotides and the plurality of stochastically labeled nucleic acid target molecules, wherein obtaining the sequencing data of stochastically labeled cell indexing oligonucleotides comprises sequencing at least a portion of the cellular label and at least a portion of a cell indexing sequence; and (e) associating the agent exposure and the sequencing data of each single cell based on the cell indexing sequence. In some embodiments, the method comprises: i) obtaining phenotypic data for each single cell; and ii) associating the phenotypic data and the sequencing data of each single cell based on the cell indexing sequence. In some embodiments, the method comprises: i) generating the spatial index of the unique cell indexing oligonucleotide of each partition to identify the spatial index of each partition; and ii) determining the cell indexing sequence of each partition based on the spatial index of each partition.

The cell indexing oligonucleotide can be associated with a cell through any of the cellular component binding reagents provided herein (e.g., an antibody). In some embodiments, the cell indexing oligonucleotide is configured to be detachable from the cellular component-binding reagent and/or synthetic particle. The method can comprise dissociating the cell indexing oligonucleotide from the cellular component-binding reagent and/or synthetic particle. In some embodiments, dissociating the cell indexing oligonucleotide comprises detaching the cell indexing oligonucleotide from the cellular component-binding reagent and/or synthetic particle by UV photocleaving, chemical treatment, heating, enzyme treatment, or any combination thereof. The dissociating can occur after stochastically labeling the cell indexing oligonucleotide or before stochastically labeling the cell indexing oligonucleotide. In some embodiments, the sequence of the cell indexing oligonucleotide complementary to the capture sequence comprises a poly (dA) region.

Disclosed herein include methods for determining the spatial locations of nucleic acid target molecules within a plurality of partitions. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) stochastically labeling the nucleic acid target molecules using the plurality of stochastic labels to generate a plurality of stochastically labeled nucleic acid target molecules; (c) obtaining the sequencing data of the plurality of stochastically labeled nucleic acid target molecules, wherein obtaining the sequencing data comprises sequencing at least a portion of the cell indexing sequence; and (d) determining the spatial location of each nucleic acid target based on the cell indexing sequence, wherein the spatial location comprises the identity of the partition from which the nucleic acid target molecule originated. In some embodiments, the method comprises: i) generating the spatial index of the cell indexing sequence of each partition to identify the spatial index of each partition; and ii) determining the cell indexing sequence of each partition based on the spatial index of each partition.

Disclosed herein include methods for associating the phenotypic data and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) obtaining phenotypic data for each single cell; (c) stochastically labeling the nucleic acid target molecules using the plurality of stochastic labels to generate a plurality of stochastically labeled nucleic acid target molecules; (d) obtaining the sequencing data of the plurality of stochastically labeled nucleic acid target molecules, wherein obtaining the sequencing data comprises sequencing at least a portion of the cell indexing sequence; and (e) associating the phenotypic data and the sequencing data of each single cell based on the cell indexing sequence. In some embodiments, the method comprises: i) generating the spatial index of the cell indexing sequence of each partition to identify the spatial index of each partition; and ii) determining the cell indexing sequence of each partition based on the spatial index of each partition.

Disclosed herein include methods for associating agent exposure and the sequencing data of a plurality of single cells. In some embodiments, the method comprises: (a) partitioning each cell of a plurality of single cells to a plurality of partitions, wherein a partition of the plurality of partitions comprises a single cell and a single synthetic particle, wherein each synthetic particle comprises a plurality of stochastic labels, wherein the stochastic labels comprise a cellular label, wherein stochastic labels associated with the same synthetic particle comprise the same cellular label, and wherein stochastic labels associated with different synthetic particles comprise different cellular labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, and wherein each of the plurality of single cells comprises a plurality of nucleic acid target molecules; (b) conducting agent exposure, wherein agent exposure comprises exposing two or more of the single cells to one or more agents, wherein at least two of the single cells are exposed to different agents and/or different concentrations of the same agent; (c) stochastically labeling the nucleic acid target molecules using the plurality of stochastic labels to generate a plurality of stochastically labeled nucleic acid target molecules; (d) obtaining the sequencing data of the plurality of stochastically labeled nucleic acid target molecules, wherein obtaining the sequencing data comprises sequencing at least a portion of the cell indexing sequence; and (e) associating the agent exposure and the sequencing data of each single cell based on the cell indexing sequence. In some embodiments, the method comprises: i) obtaining phenotypic data for each single cell; and ii) associating the phenotypic data and the sequencing data of each single cell based on the cell indexing sequence. In some embodiments, the method comprises: i) generating the spatial index of the cell indexing sequence of each partition to identify the spatial index of each partition; and ii) determining the cell indexing sequence of each partition based on the spatial index of each partition.

A partition label (e.g. a cellular label) can comprise the entire cell indexing sequence or a portion of the cell indexing sequence. The cellular label can comprise all of the n cell indexing subsequences or a portion of the n cell indexing subsequences. The number of unique spatial indices can be equal to or greater than the number of unique cellular label sequences. Generating the spatial index can be performed prior to the partitioning of the cells or can be performed after the partitioning of the cells. Generating the spatial index can be performed by the user or can be performed by the manufacturer. In some embodiments, the plurality of stochastic labels are associated with a synthetic particle and each partition comprises a single synthetic particle. In some embodiments, each of the plurality of stochastic labels comprises a molecular label sequence, wherein molecular label sequences of at least two stochastic labels of the plurality of stochastic labels comprise different molecule label sequences. In some embodiments, each synthetic particle is associated with one or more unique cellular labels, wherein the one or more unique cellular labels associated with the same synthetic particle comprise the same sequence, and wherein the one or more unique cellular labels associated with different synthetic particles comprise different sequences. In some embodiments, each of the plurality of stochastic labels comprises a target nucleic acid binding region, wherein the target nucleic acid binding region comprises a sequence selected from the group consisting of a gene-specific sequence, an oligo-dT sequence, a random multimer, and any combination thereof. In some embodiments, the stochastic labels and/or cell indexing oligonucleotides are immobilized on the synthetic particle, partially immobilized on the synthetic particle, enclosed in the synthetic particle, partially enclosed in the synthetic particle, or a combination thereof. The synthetic particle can comprise silica gel, controlled pore glass, Wang resin, Merrifield resin, a Dynabead, a Sephadex bead, a Sepharose bead, a cellulose bead, polystyrene bead, or any combination thereof. The synthetic particle can comprise a material selected from the group consisting of polydimethylsiloxane (PDMS), polystyrene, glass, polypropylene, agarose, gelatin, hydrogel, a paramagnetic material, ceramic, plastic, glass, methylstyrene, acrylic polymer, titanium, latex, cellulose, nylon, silicone, and any combination thereof. The synthetic particle can comprise a hydrogel bead, a magnetic bead, or a combination thereof. The synthetic particle can be solid or semi-solid. In some embodiments, the synthetic particle is disruptable. The synthetic particles can be partitioned prior to the single cells or the single cells can be partitioned prior to the synthetic particles.

The method can comprise lysing said single cells, thereby releasing nucleic acid target molecules from said cells. Stochastically labeling the cell indexing oligonucleotides can comprise: i) contacting the plurality of stochastic labels with the cell indexing oligonucleotides to generate stochastic labels hybridized to the cell indexing oligonucleotides; and ii) extending the stochastic labels hybridized to the cell indexing oligonucleotides to generate the plurality of stochastically labeled cell indexing oligonucleotides. Stochastically labeling the nucleic acid target molecules can comprise: i) contacting the plurality of stochastic labels with the nucleic acid target molecules to generate stochastic labels hybridized to the nucleic acid target molecules; and ii) extending the stochastic labels hybridized to the nucleic acid target molecules to generate the plurality of stochastically labeled cell nucleic acid target molecules. Extending the stochastic labels can comprise extending the stochastic labels using a DNA polymerase and/or a reverse transcriptase. Obtaining the sequencing data can comprise sequencing at least a portion of the molecular label sequence, at least a portion of the cell indexing sequence, at least a portion of the cellular label, or any combination thereof. Cell indexing oligonucleotides can comprise a target sequence complementary to a capture sequence of a stochastic label configured to capture the sequence of the cell indexing oligonucleotide. The plurality of nucleic acid target molecules can comprise ribonucleic acids (RNAs), messenger RNAs (mRNAs), microRNAs, small interfering RNAs (siRNAs), RNA degradation products, RNAs each comprising a poly(A) tail, and any combination thereof. Obtaining the sequencing data can comprise one or more of genome sequencing, exome sequencing, targeted DNA sequencing, targeted RNA sequencing, whole transcriptome RNA sequencing, ChIP-Seq, miRNA-seq, lincRNA-seq, methylation-seq, or any combination thereof. Nucleic acid target molecules can comprise binding reagent oligonucleotides associated with a cellular component-binding reagent capable of specifically binding to at least one cellular component target, and wherein the number of unique molecular label sequences associated with a unique identifier sequence of the antibody oligonucleotide in the sequencing data indicates the number of copies of the at least one cellular component target in the single cell. Nucleic acid target molecules can comprise sample indexing oligonucleotides, and wherein the sample indexing sequence of sample indexing oligonucleotide identifies the sample origin of the single cell.

In some embodiments, the plurality of single cells comprises more than 1000 cells. In some embodiments, the plurality of single cells comprises more than 10,000 cells. In some embodiments, the number of single cells can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of single cells can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. The plurality of single cells can comprise cells from a tissue or organ. The single cells can comprise cells from a thymus, white blood cells, red blood cells, liver cells, spleen cells, lung cells, heart cells, brain cells, skin cells, pancreas cells, stomach cells, cells from the oral cavity, cells from the nasal cavity, colon cells, small intestine cells, kidney cells, cells from a gland, brain cells, neural cells, glial cells, eye cells, reproductive organ cells, bladder cells, gamete cells, human cells, fetal cells, amniotic cells, or any combination thereof. In some embodiments, the plurality of single cells comprise plant cells, fungi cells, bacterial cells, prokaryotic cells, eukaryotic cells, unicellular cells, multi-cellular cells, immune cells, or any combination thereof. In some embodiments, the cells selected from the group consisting of T cells, B cells, monocytes, macrophages, neutrophils, dendritic cells, natural killer cells, fibroblasts, stromal cells, stem cells, progenitor cells, tumor cells, tumor stem cells, tumor infiltrating lymphocytes, and combinations thereof. The plurality of partitions can comprise a plurality of droplets. The plurality of partitions can comprise microwells of any microwell array disclosed herein. A cell indexing sequence can comprise n cell indexing subsequences, wherein n is an integer greater than 1, wherein each cell indexing subsequence is selected from p unique cell indexing subsequences, wherein p is an integer greater than 1, wherein two unique cell indexing oligonucleotides comprise different cell indexing sequences.

Methods of Conducing Agent Exposure and Correlating with Sequencing Data

There are provided, in some embodiments, methods of associating the agent exposure of each single cell. Associating the agent exposure of each single cell can comprise identifying the one or more agents each single cell was exposed to and concentrations thereof. In some embodiments, conducting agent exposure comprises exposing two or more single cells to different agents and/or exposing two or more single cells to different concentrations of the same agent. The method can comprise inducing the release of an agent covalently attached to one or more inner surfaces of the partitions (e.g., micro-wells) to initiate agent exposure. In some embodiments, a plurality of the micro-wells comprise an agent covalently attached to one or more inner surfaces of the micro-wells. A plurality of the micro-wells can comprise different amounts of the agent covalently attached to one or more inner surfaces of the micro-wells and/or different agents covalently attached to one or more inner surfaces of the micro-wells. The covalent attachment can comprise the use of one or more cleavable linkers (e.g., acid-labile linkers, base-labile linkers, photocleavable linkers, enzyme-cleavable linkers, or any combination thereof) to enable release of the agent. Upon release, the agent(s) can contact the single cell in the micro-well. At least two the micro-wells of the array can comprise different amounts of the same agent covalently attached to one or more inner surfaces of the micro-wells. At least two the micro-wells of the array can comprise different agents covalently attached to one or more inner surfaces of the micro-wells.

The agent and/or a second agent can comprise one or more components. In some embodiments, the agent comprises one or more of a chemical agent, a pharmaceutical, small molecule, a biologic, a CRISPR single-guide RNA (sgRNA), a small interfering RNA (siRNA), CRISPR RNA (crRNA), a small hairpin RNA (shRNA), a microRNA (miRNA), a piwi-interacting RNA (piRNA), an antisense oligonucleotide, a peptide or peptidomimetic inhibitor, an aptamer, an antibody, an intrabody, or any combination thereof. In some embodiments, the agent can comprise one or more of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an antimicrobial peptide, a pore-forming peptide, a targeting or cytotoxic peptide, a degradation or self-destruction peptide, a CRISPR component system or component thereof, DNA, RNA, artificial nucleic acids, a nanoparticle, an oligonucleotide aptamer, a peptide aptamer, or any combination thereof. The agent can possesses at least one effector activity selected from the group consisting of: modulating a biological activity, binding a regulatory protein, modulating enzymatic activity, modulating substrate binding, modulating receptor activation, modulating protein stability/degradation, modulating transcript stability/degradation, and any combination thereof.

In some embodiments, the agent can comprise an infectious agent, an anti-infectious agent, or a mixture of an infectious agent and an anti-infectious agent. An infectious agent can comprise a virus, a bacterium, a fungus, a protozoal parasite, or any combination thereof. An anti-infectious agent can comprise an anti-bacterial agent, an anti-fungal agent, an anti-parasitic agent, an anti-viral agent, or any combination thereof. In some embodiments, the agent can comprise a cytotoxic agent, such as, for example, a chemotherapeutic agent, a biologic agent, a toxin, a radioactive isotope, or any combination thereof. The agent can comprise a non-active component of a therapeutic, such as, for example, an excipient, carrier, diluent, vehicle, adjuvant, empty vector, or any combination thereof.

In some embodiments, the agent can comprise an expression vector, wherein the expression vector encodes one or more of the following: an mRNA, an antisense nucleic acid molecule, a RNAi molecule, a shRNA, a mature miRNA, a pre-miRNA, a pri-miRNA, an anti-miRNA, a ribozyme, any combination thereof. The single cells can comprise a recombinant expression vector. The recombinant expression vector can comprise an inducible promoter, wherein the expression of one or more of the following are under the control of said inducible promoter: an mRNA, an antisense nucleic acid molecule, a RNAi molecule, a shRNA, a mature miRNA, a pre-miRNA, a pri-miRNA, an anti-miRNA, a ribozyme, any combination thereof. The agent can comprise a dose-dependent inducer of the inducible promoter (e.g., tetracycline, pristinamycin, macrolide, ecdysone, mifepristone, or any combination thereof). In some embodiments, the agent modulates the expression and/or activity of one or more target biomarkers. In some embodiments, one or more single cells of the plurality of single cells lack exposure to the one or more agents.

In some embodiments, the concentration of the agent in the plurality of micro-wells is non-uniform. Methods, compositions, systems, devices, and kits for introducing one or more components into a fluid have been disclosed in U.S. Provisional Application No. 62/820,259, filed on Mar. 18, 2019, the content of which is hereby expressly incorporated by reference in its entirety. A first fluid and a second fluid can be co-injected into a fluidic channel of a flow cell. In some embodiments, the first fluid and a second fluid are immiscible (e.g. an aqueous buffer and a non-aqueous liquid). In some embodiments, the second fluid is less dense than the first fluid. In some embodiments, the method and compositions provided herein enable the linkage of high-throughput drug screening and massively parallel sequencing. For example, there are provided, in some embodiments, methods of measuring the dose-dependent phenotypic effects of an agent on single cells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) capturing single cells in the plurality of microwells; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an agent, wherein the flow rate of the first fluid is not uniform along the longitudinal path of the fluidic channel, wherein the agent enters the microwell by diffusion during the duration, wherein the final concentration of the agent in the content of the microwell is unequal for at least two microwells of the plurality of microwells, and wherein the second fluid seals the content of the microwell; and (d) measuring one or more phenotypic effects dependent on the final concentration of the agent in the microwell. In some embodiments, the density of the first fluid is greater than the density of the second fluid and/or the first fluid and the second fluid are immiscible. The method can comprise a second co-injecting of fluids. The second co-injecting can comprise co-injecting a second first liquid of a second co-injection and a second liquid of a second co-injection into the fluidic channel, wherein the first liquid of the second co-injection is introduced into the fluidic channel immediately before the second liquid of the second co-injection. The second liquid of the second co-injection can seal the content of the microwell. In some embodiments, the density of the first liquid of the second co-injection is greater than the density of second liquid of the second co-injection, and wherein the first liquid of the second co-injection and the second liquid of the second co-injection are immiscible. The second co-injecting can be performed in the reverse direction or same direction relative to the first co-injecting. In some embodiments, the first fluid of the second co-injection can comprise a second agent. The method can comprise 3, 4, 5, 6, 7, 8, 9, or more co-injections of fluids as disclosed herein, and one or more of the first fluids of said co-injections can comprise 3, 4, 5, 6, 7, 8, 9, or more additional agents. In some embodiments, the first fluid is a first plug and the second fluid is a second plug. The flow rate of the first fluid can be higher at an anterior position along the longitudinal path of the fluidic channel relative a posterior position along the longitudinal path of the fluidic channel and/or the flow rate of the first fluid can be lower at an anterior position along the longitudinal path of the fluidic channel relative a posterior position along the longitudinal path of the fluidic channel. In some embodiments, the difference between the flow rate of the first fluid at an anterior position along the longitudinal path of the fluidic channel relative a posterior position along the longitudinal path of the fluidic channel is, is about, is at most about, or is at least about 1.1-fold. In some embodiments, the ratio of the flow rate of the first fluid at an anterior position along the longitudinal path of the fluidic channel relative the flow rate at a posterior position along the longitudinal path of the fluidic channel ranges from 1:100 to 100:1. In some embodiments, the ratio of the two flow rates is at most 10:1. In some embodiments, the ratio of the two flow rates is at most 100:1. In some embodiments, the ratio of the two flow rates is at most 1:1000. In some embodiments, the ratio of the two flow rates is at least 1:10. In some embodiments, the ratio of the two flow rates is at least 1:100. In some embodiments, the ratio of the two flow rates is at least 1:1000. In some embodiments, the final concentration of the agent in the contents of the plurality of microwells following the serial co-injecting is non-uniform. The final concentration of the agent in the content of each microwell can change along the longitudinal path of the fluidic channel. In some embodiments, the change in the final concentration of the agent in the content of each microwell can be linear, non-linear, exponential, and/or logarithmic. In some embodiments, the difference between the final concentration of the agent in the content of a microwell at an anterior position along the longitudinal path of the fluidic channel relative a posterior position along the longitudinal path of the fluidic channel is, is about, is at most about, or is at least about 1.1-fold. In some embodiments, the ratio of the final concentration of the agent in the content of a microwell at an anterior position along the longitudinal path of the fluidic channel relative a posterior position along the longitudinal path of the fluidic channel ranges from 1:100 to 100:1. In some embodiments, the ratio of the two final concentrations is at most 10:1. In some embodiments, the ratio of the two final concentrations is at most 100:1. In some embodiments, the ratio of the two final concentrations is at most 1:1000. In some embodiments, the ratio of the two final concentrations is at least 1:10. In some embodiments, the ratio of the two final concentrations is at least 1:100. In some embodiments, the ratio of the two final concentrations is at least 1:1000.

In some embodiments, the methods comprise measuring one or more phenotypic effects dependent on the final concentration of the agent in the microwell. Measuring one or more phenotypic effects dependent on the final concentration of the agent in the microwell can comprise imaging according to the methods disclosed herein. Measuring one or more phenotypic effects dependent on the final concentration of the agent in the microwell can comprise mRNA expression profiling, wherein mRNA expression profiling comprises quantitative analysis of a plurality of mRNA targets in a cell. Measuring one or more phenotypic effects dependent on the final concentration of the agent in the microwell can comprise protein expression profiling, wherein protein expression profiling comprises quantitative analysis of a plurality of protein targets in a cell. Measuring one or more phenotypic effects dependent on the final concentration of the agent in the microwell can comprise simultaneous quantitative analysis of a plurality of protein targets and a plurality of nucleic acid target molecules in a cell.

There are also provided, in some embodiments, methods of estimating the concentration of the agent at each longitudinal flowcell position (and thereby determining the agent exposure of each cell). In some embodiments, the first fluid comprises a fluorescent dye, wherein the proportion of the fluorescent dye to the agent is known. The flow cell can comprise a transparent window for optical imaging, and the method can comprise optical imaging of the flow cell after the co-injecting of the first fluid and the second fluid, wherein optical imaging comprises a measurement of the fluorescent dye in each microwell. The measurement of fluorescent dye in each microwell can enable the estimation of the concentration of the agent in each microwell. The method can further comprise deriving an estimation of a concentration of the agent each cell was exposed to based on the determination of the microwell of origin of each cell and the estimation of the concentration of the agent at each longitudinal flowcell position. The method can comprise correlation analysis of the estimated concentration of the agent each cell was exposed to and the RNA and/or DNA expression profiles of said cells. The correlation analysis can identifies one or more of the following: candidate therapeutic agents, candidate doses of candidate therapeutic agents, and cellular targets of candidate therapeutic agents.

Methods of Obtaining Phenotypic Data and Correlating with Sequencing Data

There are provided, in some embodiments, methods of obtaining phenotypic data for each single cell comprises imaging of each single cell. In some embodiments, imaging of each single cell yields imaging data. Imaging data comprises phenotypic data. In some embodiments, imaging comprises microscopy (e.g., fluorescence microscopy, confocal microscopy, quantitative microscopy), time-lapse imaging microscopy, fluorescence microscopy, multi-photon microscopy, quantitative phase microscopy, surface enhanced Raman spectroscopy, videography, manual visual analysis, automated visual analysis, or any combination thereof. In some embodiments, the plurality of partitions can be imaged sequentially, simultaneously, and/or continuously. In some embodiments, imaging is performed at one or more time points. In some embodiments, the imaging occurs at sequential intervals (e.g., about 1 second to about 10 minutes) for a period of time (e.g., about 1 minute to about 24 hours). Imaging can be performed before and/or after conducting agent exposure. The phenotypic effects of the one or more agents can be determined by imaging of the single cells.

In some embodiments, the plurality of single cells are derived from a tissue sample. The plurality of single cells can comprise a plurality of cell types. In some embodiments, the phenotypic data elucidates the identity of each cell type. In some embodiments, the single cells comprise a tagged endogenous protein, such as, for example a fluorescent protein, a luminescent protein, a photoactivatable protein, a FLAG tag, a SNAP tag, a Halo tag, or any combination thereof. A fluorescent protein can be a green fluorescent protein (GFP), blue fluorescent protein, cyan fluorescent protein, yellow fluorescent protein or a red fluorescent protein. Phenotypic data can comprise measurement of one or more of the localization, expression intensity, and persistence of expression of the tagged endogenous protein. Phenotypic data can comprise measurement of cell death, and wherein the cell death is evaluated by detecting apoptosis markers. In some embodiments, one or more single cells are labeled with a reporter molecule.

In some embodiments, phenotypic data comprises measurement of a dynamic behavior (e.g., cellular activation, cellular inhibition, protein secretion, microvesicle secretion, exosome secretion, microparticle secretion, metabolite secretion, small molecule secretion, proton secretion, protein expression, or any combination thereof) of the single cells as a function of time. Phenotypic data can comprise measurement of cellular activation, cellular inhibition, cellular interaction, protein expression, protein secretion, metabolite secretion, changes in lipid profiles, microvesicle secretion, exosome secretion, microparticle secretion, changes in cellular mass, cellular proliferation, changes in cellular morphology, motility, cell death, cell cytotoxicity, cell lysis, cell membrane polarization, establishment of a synapse, dynamic trafficking of proteins, granule polarization, calcium activation, metabolic changes, small molecule secretion, proton secretion, or any combination thereof. In some embodiments, the phenotypic data comprises measurement of one or more cellular attributes (e.g., physical attributes, morphological attributes, intracellular attributes, biochemical attributes, or any combination thereof). Physical attributes can comprise cell size, volume, conductivity, low and high angle scatter, density, or any combination thereof. Morphological attributes can comprise one or more of: cell shape, area, size, and lobularity; nucleus shape area, size, and lobularity; mitochondria shape, area, size, and lobularity; and ratio of nuclear volume to cell volume. Intracellular attributes can comprise nucleus centroid/cell centroid distance, nucleus lobe centroid distance, distribution of proteins with the cells, distribution of organelles within the cells, or any combination thereof. Biochemical attributes can comprise expression level of cellular proteins, cell surface proteins, cytoplasmic proteins, nuclear proteins, cellular nucleic acids, cell surface nucleic acids, cytoplasmic nucleic acids, nuclear nucleic acids, cellular carbohydrates, cell surface carbohydrates, cytoplasmic carbohydrates, nuclear carbohydrates, or any combination thereof. Phenotypic data can comprise measurement of one or more cellular features indicating cell proliferation (e.g., nuclear count, cell count, total cell mass, total DNA, the phosphorylation state of cell cycle regulatory proteins, the post-translational modification state of any protein involved in cell growth or division), stress pathways (e.g., transcription factor activation of NF-κB, AP1, ATF2, MSK1, CREB, or NFAT, and kinase activation of p38, JNK, ERK, RSK90, MEK), organelle function (e.g., cytoskeletal organization, mitochondrial mass or membrane potential, peroxisome mass, golgi organization, plasma membrane permeability), cell cycle state (e.g., DNA content, Histone H3 phosphorylation state, Rb phosporylation state, cyclin B1 (CDKl) biosynthesis, cyclin DI (CDK4, 6) biosynthesis, cyclin E (CDK2) biosynthesis), morphology, apoptosis (e.g., nuclear size and shape, DNA content and degradation, caspase activation, phosphatidyl-expression, Bax translocation), DNA damage (e.g., repair protein (APE) expression, tumor suppressor (p53, Rb) expression, oxidative activity (8-oxoguanine), transcription activity (Oct1)), metabolism (e.g., cAMP concentration, P-glycoprotein activity or CYP450 induction/inhibition, the concentration of an added substance), signal transduction (e.g., Ca++ ion concentration, (pH) expression of a protein, activation of a protein, modification of a protein, translocation of a protein, interaction between proteins known to be associated with a specific pathway), cell differentiation (e.g., expression of a tissue specific protein, exhibiting a tissue specific morphology), or any combination thereof. The method can comprise phenotypic observation of the single cells through imaging prior to bead loading and/or after bead loading.

In some embodiments, the system software may provide integrated real-time image analysis and instrument control, so that cells may be optically monitored and classified according to a pre-determined set of characteristics. Examples of cellular characteristics that may be optically monitored include, but are not limited to, cell size, cell shape, live cell/dead cell determination (e.g. using selectively absorbed chromophores such as Trypan blue, or fluorescent dyes such as calcein AM, ethidiumhomodimer-1, $DiOC_2(3)$, $DiOC_5(3)$, $DiOC_6(3)$, $DiSC_3(5)$, $DiIC_1(5)$, $DiOC_{18}(3)$, propidium iodide, SYBR® 14, SYTOX® Green, etc.), cells exhibiting a specified range of intracellular pH (e.g. using intracellular pH-sensitive fluorescent probes such as 2',7'-Bis-(2-carboxyethyl)-5-(and-6-)carboxyfluorescein (BCECF), 2',7'-bis-(2-carboxypropyl)-5-(and-6-)-carboxyfluorescein (BCPCF), etc.), cells exhibiting a specified range of membrane potential (e.g. using membrane potential-sensitive fluorophores such as FluoVolt™, di-3-ANEPPDHQ, Bis-(1,3-Dibutylbarbituric Acid) Trimethine Oxonol ($DiBAC_4(3)$), $DiBAC_4(5)$, $DiSBAC_2(3)$, Merocyanine 540, JC-1, JC-9, Oxonol V, Oxonol VI, Tetramethylrhodamine methyl and ethyl esters, Rhodamine 123, Di-4-ANEPPS, Di-8-ANEPPS, Di-2-ANEPEQ, Di-3-ANEPPDHQ, Di-4-ANEPPDHQ, etc.), cells exhibiting a specified level of intracellular calcium (e.g. using $Ca^{2+}$-sensitive fluorescent dyes such as fura-2, indo-1, fluo-3, fluo-4, Calcium Green-1, Quin 2, etc.), cells exhibiting one or more specified cell surface markers (e.g. using fluorescently-labeled antibodies directed towards the cell surface markers), cells expressing fluorescent proteins (e.g. GFP, bilirubin-inducible fluorescent protein, UnaG, dsRed, eqFP611, Dronpa, TagRFPs, KFP, EosFP, Dendra, IrisFP, etc.), and the like. In many embodiments, two or more dyes, fluorophores, or other optical probes having non-overlapping spectral properties (e.g. non-overlapping excitation peaks, non-overlapping absorption or emission peaks, etc.) can be selected so that cells may be simultaneously characterized with respect to two or more properties.

Compositions and Kits

There are provided, in some embodiments, kits for producing a plurality of cell indexing oligonucleotides comprising n cell indexing subsequences. The kit can comprise p first indexing oligonucleotides, wherein p is an integer greater than 1, and wherein each first cell indexing oligonucleotide is a single-stranded oligonucleotide comprising a first cell indexing subsequence and a first linker sequence. The kit can comprise n−2 pluralities of p intervening indexing oligonucleotides, wherein n is an integer greater than 2, wherein each intervening indexing oligonucleotide is a single-stranded oligonucleotide comprising a complementary sequence of the nth−1 linker sequence, an nth cell indexing subsequence and an nth linker sequence. The kit can comprise p final indexing oligonucleotides, wherein each final indexing oligonucleotide is a single-stranded oligonucleotide comprising a complementary sequence of the nth linker sequence, an nth cell indexing subsequence and a target sequence. The kit can comprise a DNA polymerase (e.g., Klenow fragment). The kit can comprise an enzyme with 5' to 3' exonuclease activity (e.g., Lamba exonuclease).

There are provided, in some embodiments, kits for producing a plurality of cell indexing oligonucleotides comprising n cell indexing subsequences. The kit can comprise p first indexing oligonucleotides, wherein p is an integer greater than 1, wherein each first indexing oligonucleotide is double-stranded oligonucleotide comprising a first cell indexing subsequence and a first linker sequence, and wherein the first linker sequence comprises a first restriction site. The kit can comprise n−2 pluralities of p intervening indexing oligonucleotides, wherein n is an integer greater than 2, wherein each intervening indexing oligonucleotide is a double-stranded oligonucleotide comprising an comprises an (n−1)th sequence, an nth probe binding site and an nth linker sequence, wherein the nth linker sequence comprises an nth restriction site. The kit can comprise p final indexing oligonucleotides, wherein each final indexing oligonucleotide is a double-stranded oligonucleotide comprising an nth linker sequence, a nth cell indexing subsequence and a target sequence. The kit can comprise n different restriction enzymes. The kit can comprise a ligase.

The kit can comprise any cellular component-binding reagent disclosed herein. In some embodiments, the first indexing oligonucleotide comprises a linker, and wherein the cellular component-binding reagent is configured to associate with the linker of the first indexing oligonucleotide. The kit can comprise any synthetic particle disclosed herein. The kit can comprise a plurality of synthetic particles, wherein the first indexing oligonucleotide comprises a linker, and wherein the plurality of synthetic particles are configured to associate with the linker of the first indexing oligonucleotide. The cell indexing oligonucleotide can comprise cell indexing subsequence$_1$-linker sequence$_1$-cell indexing subsequence$_2$-linker sequence$_2$- . . . cell indexing subsequence$_{n-1}$-linker sequence$_n$-cell indexing subsequence$_n$-target sequence. The target sequence can comprise a poly(dA) region. In some embodiments, each plurality of p indexing oligonucleotides comprise a different cell indexing subsequence. Different cell indexing subsequences can binding different probes. In some embodiments, n is an integer from 3 to 20 and p is an integer from 4-1000. In some embodiments, the plurality of cell indexing oligonucleotides comprises equal to or less than $p^n$ unique cell indexing oligonucleotides. In some embodiments, the plurality of cell indexing oligonucleotides comprises at least 10,000 unique cell indexing oligonucleotides. In some embodiments, the plurality of cell indexing oligonucleotides comprises at least 100,000 unique cell indexing oligonucleotides.

Also provided herein are probe compositions. In some embodiments, the probe compositions comprise n pluralities of probes, wherein n is an integer greater than 1, wherein the probes selectively anneal to the cell indexing subsequences of cell indexing oligonucleotides with complementary sequences, wherein each plurality of probes comprises m unique probes, wherein m is an integer greater than 1, wherein unique probes selectively anneal to different cell indexing subsequences, and wherein the probes comprise a detectable moiety, or precursor thereof. In some embodiments, the probe compositions comprise n pluralities of probes, wherein n is an integer greater than 1, wherein the probes selectively anneal to the cell indexing subsequences of cell indexing oligonucleotides with complementary sequences, wherein each plurality of probes comprises p unique probes, wherein p is an integer greater than 1, wherein unique probes selectively anneal to different cell indexing subsequences, wherein m probes of the p unique probes comprise a detectable moiety, or precursor thereof, wherein m is an integer greater than 1, and wherein m is p−1. The probes can be designed to anneal to any of the cell indexing subsequences provided herein. The detectable moieties can be selected from any of the detectable moieties disclosed herein.

There are provided, in some embodiments, cell indexing oligonucleotide compositions. In some embodiments, the cell indexing oligonucleotide compositions comprise a plurality of cell indexing oligonucleotides, wherein the plurality of cell indexing oligonucleotides comprises at least 2 unique cell indexing oligonucleotides, wherein a cell indexing oligonucleotide comprises a cell indexing sequence, wherein a cell indexing sequence comprises n cell indexing subsequences, wherein n is an integer greater than 1, wherein each nth cell indexing subsequence is selected from p unique cell indexing subsequences, wherein p is an integer greater than 1, wherein two unique cell indexing oligonucleotides comprise different cell indexing sequences. The cell indexing oligonucleotide compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

There are provided, in some embodiments, cell compositions. The cell compositions can comprise a cell, wherein one or more copies of a unique cell indexing oligonucleotide are associated with the cell, wherein the unique cell indexing oligonucleotide is selected from a plurality of cell indexing oligonucleotides comprising at least 100 unique cell indexing oligonucleotides, wherein the cell indexing oligonucleotide comprises a cell indexing sequence, wherein the cell indexing sequence comprises n cell indexing subsequences, wherein n is an integer greater than 1. The cell compositions can comprise a plurality of cells, wherein each single cell is associated with one or more unique cell indexing oligonucleotides, wherein the one or more unique cell indexing oligonucleotides associated with the same cell comprise the same cell indexing sequence, wherein the one or more unique cell indexing oligonucleotides associated with different cells comprise different cell indexing sequences, wherein the cell indexing sequence comprises n cell indexing subsequences, wherein n is an integer greater than 1. The cell compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

In some embodiments, one or more of the n cell indexing subsequences are separated by a linker sequence. The cell indexing oligonucleotides can comprise cell indexing subsequence$_1$-linker sequence$_1$-cell indexing subsequence$_2$-linker sequence$_2$- . . . cell indexing subsequence$_{n-1}$-linker sequence$_n$-cell indexing subsequence$_n$-target sequence. The cell indexing oligonucleotide can comprise a linker. A cellular component-binding reagent can be associated with the cell indexing oligonucleotide via the linker. In some embodiments, the linker comprises a chemical group. The chemical group can be reversibly attached to the first indexing oligonucleotide. The cellular component-binding reagent can comprise a chemical group (e.g., a UV photocleavable group, a streptavidin, a biotin, an amine, a disulfide linkage, or any combination thereof). The linker can comprise a 5' amine. The linker can comprise a carbon chain (e.g., 2-30 carbons). In some embodiments, the cell indexing oligonucleotide is covalently attached to the cellular component-binding reagent. In some embodiments, the cell indexing oligonucleotide is conjugated to the cellular component-binding reagent (e.g., via a chemical group selected from the group consisting of a UV photocleavable group, a streptavidin, a biotin, an amine, and a combination thereof). The cell indexing oligonucleotide can be non-covalently attached to the cellular component-binding reagent. In some embodiments, the cell indexing oligonucleotide can be configured to be detachable from the cellular component-binding reagent. In some embodiments, the cell indexing oligonucleotide is associated with a cell via the cellular component binding reagent. In some embodiments, each cell is partitioned to a plurality of partitions (e.g., microwells of a microwell array) wherein a partition comprises a single cell.

There are provided, in some embodiments, synthetic particle compositions. The composition can comprise a single synthetic particle. The composition can comprise a plurality of synthetic particles. The synthetic particle can comprise a plurality of stochastic labels, wherein the stochastic labels comprise a cell indexing sequence, wherein the cell indexing sequence is selected from a plurality of cell indexing sequences comprising at least 100 unique cell indexing sequences, wherein the cell indexing sequence comprises n cell indexing subsequences, wherein n is an integer greater than 1. The synthetic particle can comprise a plurality of stochastic labels, wherein the stochastic labels comprise a cell indexing sequence, wherein the stochastic labels associated with the same synthetic particle comprise the same cell indexing sequence, wherein the stochastic labels associated with different synthetic particles comprise different cell indexing sequences, wherein the cell indexing sequence comprises n cell indexing subsequences, wherein n is an integer greater than 1. The synthetic particle composition can comprise n pluralities of probes, wherein probes can selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

There are provided, in some embodiments, micro-well array compositions. A micro-well array can comprise at least 100 micro-wells, wherein each micro-well has a volume ranging from about 1,000 m$^3$ to about 786,000 μm$^3$, wherein a plurality of the micro-wells comprise a single synthetic particle from a plurality of synthetic particles, wherein each synthetic particle comprises a plurality of stochastic labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, wherein the cell indexing sequence comprises n cell indexing subsequences, wherein n is an integer greater than 1. The micro-well array compositions can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

There are provided, in some embodiments, cartridge compositions. A cartridge can comprise at least one of: an inlet port, an outlet port, a pump, a valve, a vent, a reservoir, a sample collection chamber, a temperature control apparatus, or any combination thereof, wherein the cartridge comprises a micro-well array, wherein the micro-well array comprises at least 100 micro-wells, wherein each micro-well has a volume ranging from about 1,000 m³ to about 786,000 µm³, wherein a plurality of the micro-wells comprise a single synthetic particle from a plurality of synthetic particles, wherein each synthetic particle comprises a plurality of stochastic labels, wherein the stochastic labels comprise a cell indexing sequence, wherein the stochastic labels associated with the same synthetic particle comprise the same cell indexing sequence, and wherein the stochastic labels associated with different synthetic particles comprise different cell indexing sequences, wherein the cell indexing sequence comprises n cell indexing subsequences, wherein n is an integer greater than 1. The cartridge composition can comprise n pluralities of probes, wherein the probes selectively anneal to cell indexing subsequences with complementary sequences, wherein each plurality of probes comprises two or more unique probes, wherein unique probes selectively anneal to different cell indexing subsequences, and wherein one or more of the probes of each plurality of probes comprise a detectable moiety, or precursor thereof.

In some embodiments, the stochastic labels comprise a partition label (e.g., a cellular label), wherein stochastic labels associated with the same synthetic particle comprise the same cellular label, and wherein stochastic labels associated with different synthetic particles comprise different cellular labels. The cellular label can comprise the cell indexing sequence. A portion of the cellular label can comprise the cell indexing sequence. A portion of the cellular label comprises a portion of the cell indexing sequence. In some embodiments, the cellular label can comprise all of the n cell indexing subsequences. The cellular label can comprise a portion of the cell indexing sequence. The cellular label can comprise one or more cell indexing subsequences of the n cell indexing subsequences of the cell indexing sequence. In some embodiments, each nth cell indexing subsequence is selected from p unique cell indexing subsequences, wherein p is an integer greater than 1.

The cell indexing sequence can be associated with a spatial index. In some embodiments, determining the spatial index comprises sequentially hybridizing and imaging n pluralities of probes annealing to the n cell indexing subsequences for n cycles. The n pluralities of probes can comprise one or more detectable moieties, wherein imaging comprises detecting the one or more detectable moieties. In some embodiments, the detectable moieties of the probes comprise fluorescent labels, and sequential hybridization and imaging comprises sequential hybridization and fluorescent imaging. The spatial index can comprise a series of n signals and/or absence of signals detected in the n cycles. In some embodiments, p is an integer from 2 to 15. In some embodiments, n is an integer from 2 to 15. The plurality of cell indexing sequences can comprise at least 1,000, at least 10,000, or at least 100,000, unique cell indexing sequences.

In some embodiments, each synthetic particle has been partitioned to a plurality of partitions, wherein a partition comprises a single synthetic particle, and wherein the spatial index of the unique cell indexing sequence associated with each synthetic particle has been elucidated by generating the spatial index. In some embodiments, said generating the spatial index was performed in the plurality of partitions. The composition can comprise a spatial index lookup table. The spatial index lookup table can identify the cell indexing sequence and/or spatial index and/or cellular label associated with each synthetic particle in the plurality of partitions. In some embodiments, association of the cellular label and the cell indexing sequence during sequencing identifies the partition (e.g. micro-well) of origin of each sequenced nucleic acid target molecule. In some embodiments, the cellular label comprises the cell indexing sequence, and sequencing of the cellular label identifies the micro-well of origin of each sequenced nucleic acid target molecule. The composition can comprise a buffer, a cartridge, and/or one or more reagents for a reverse transcription reaction and/or amplification reaction.

Figure 9B:
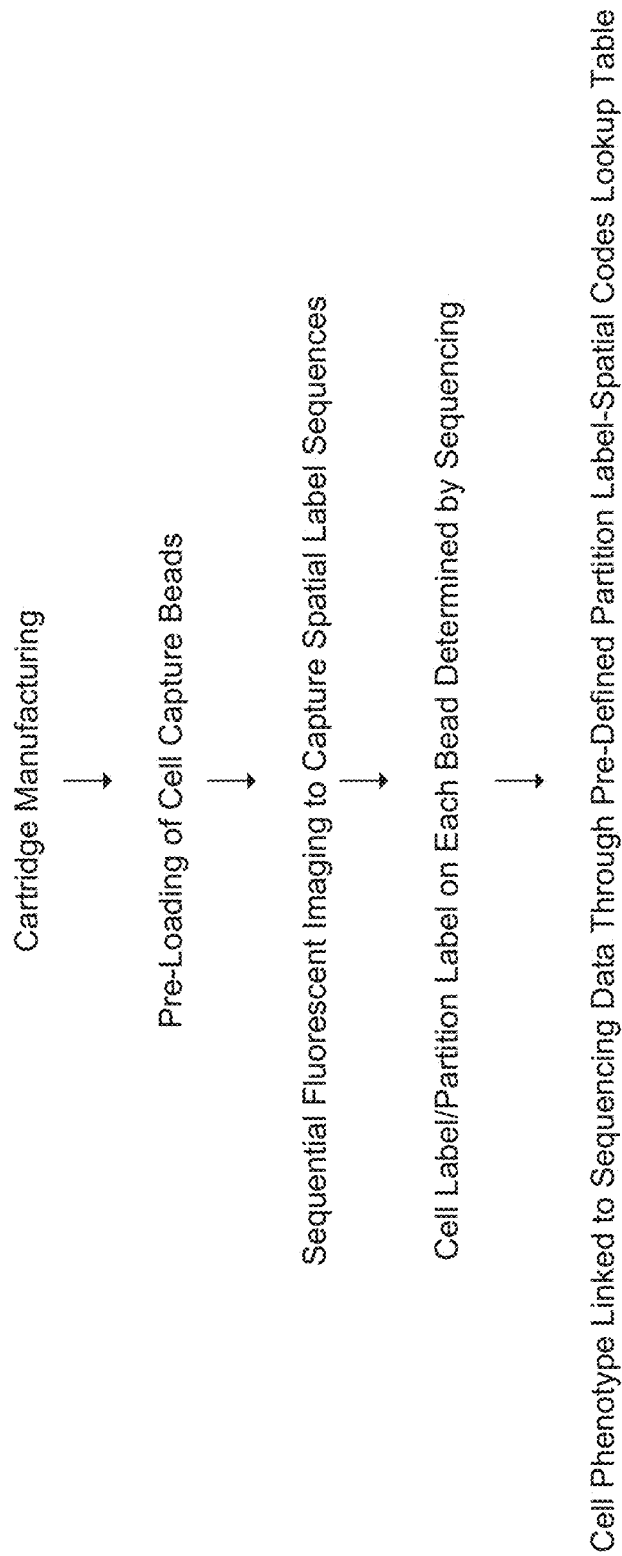
FIG. 9B depicts a non-limiting exemplary workflow of determining and using spatial indices associated with cell capture particles preloaded within a cartridge.

FIG. 9B depicts a non-limiting exemplary workflow of determining and using spatial indices associated with cell capture particles preloaded within a cartridge. In some embodiments, there are provided cartridges in which solid supports (e.g., synthetic particles, BD Rhapsody Cell Capture Beads) are preloaded (e.g., beads are pre-distributed into the one or more microwell arrays of the cartridge). In some such embodiments, preloading of the cartridge comprises associating a plurality of synthetic particles with a plurality of micro-wells such that each synthetic particle is associated with a single micro-well. In some embodiments, the synthetic particles are situated within the microwells of the preloaded cartridge. The preloaded cartridge can comprise two mated microwell arrays: one pre-loaded with beads which are held in place by a first magnet, and the other for use by the user in loading individual cells. In some embodiments, the preloaded synthetic particles comprise cell indexing oligonucleotides. In some embodiments, the preloaded synthetic particles comprise stochastic labels, and a stochastic label comprises a cell indexing sequence. A stochastic label can comprise a unique partition label (e.g., cellular label). A unique cellular label can comprise all or some of the cell indexing sequence. In some embodiments, determining the spatial index associated with the cell indexing sequence of each of the pre-distributed synthetic particles (e.g., cell capture beads) within the cartridge is performed according the methods provided herein (e.g., sequential fluorescent imaging) by a manufacturer, generating a barcoded cartridge. In some embodiments, a plurality of micro-wells of a barcoded cartridge are linked to the spatial index of a pre-loaded bead, which is further linked to the cell indexing sequence. In some embodiments, kits are provided comprising a barcoded cartridge and a spatial index lookup table. The spatial index lookup table can provide the spatial index and/or the cell indexing sequence and/or partition label (e.g., cellular label) of the plurality of micro-wells of a barcoded cartridge, enabling a downstream user of the barcoded cartridge to determine the spatial locations of sequenced nucleic acid target molecules within a plurality of partitions and/or associate sequencing data with phenotypic data and/or agent exposure according the methods provided herein.

There are provided, in some embodiments, methods of spatial encoding to correlate phenotypical information with sequencing in single-cell multi-omics workflows. The methods disclosed herein can link transcriptomics data to spatial information and imaging data (e.g., pairing gene expression with morphology or drug response). There are provide, in some embodiments, methods to link phenotypical information (obtained from imaging data) of single cells to sequencing data generated from corresponding cells through spatial encoding of fluorescent signals.

Current single-cell multi-omics workflows (e.g., BD Rhapsody & AbSeq systems) can possess the capacity for capturing imaging data of single cells, which can be used for future applications such as high-throughput drug screening on single cells. These single-cell multi-omics workflows can also provide sequencing readouts of single cells. However, there is presently no means to link phenotypical information to corresponding sequencing data for single cells of interest. Provided herein are two approaches to solve this problem.

In a first approach, cells can be labeled with universal antibodies conjugated to an oligonucleotide that has unique combination of short tandem sequences for fluorescent probes to bind to, as well as a polyA tail for the oligo to be captured on a capture bead in a 3' RNA-seq platform. Combinatorial staining or ultra-diluted staining methods can be used to label each cell with a unique tag. Sequential fluorescent imaging can be employed to read out the barcodes, and the unique spatial barcode of each cell can be preserved and linked to gene expression of the cell through sequencing. In some embodiments, sequential fluorescent imaging creates spatial barcodes by imaging that can later be linked to cell label and transcriptomics data (e.g., by pairing fluorescent barcode to sequence barcode of the oligonucleotides). Advantages of this first approach can be that the number of unique cell indices to encode is small (e.g., 10,000), thus requiring less fluorescent probes with less cycles (e.g., 3 probes+7 cycles), and that phenotypic observation of single cells via imaging is performed before bead loading.

In a second approach, rather than labelling cells, unique cell label oligonucleotides present on synthetic particles (e.g. unique cell label oligonucleotides on BD Rhapsody Cell Capture Beads) can be utilized. With this second approach, oligonucleotide probes can be designed that bind to cell labels and conjugate fluorophores to generate different pools of fluorescent probes. During a spatial encoding process, several rounds of probe binding and fluorescent imaging can be conducted sequentially to record the spatial code of a bead paired with a cell (e.g., a cell of an interesting phenotype). After sequencing, phenotypical information of cells can be linked to sequencing data through the predefined cell label-spatial code lookup table. This approach can also be employed with beads pre-loaded onto cartridges. After cartridge manufacturing, beads (e.g., Cell Capture Beads) can be pre-loaded into each cartridge. After beads pre-loading, spatial encoding of beads through sequential fluorescent imaging can be conducted for every cartridge. Since all these processes happen at manufacturing, customers will receive a barcoded cartridge, with every micro-well liked to the spatial code of a pre-loaded bead, which is further linked to the cell label sequence. These cartridges can be employed for single-cell phenotypic and multi-omics studies. Advantages of this approach can include 1) multicolor fluorescent microscopy can be off-loaded to manufacturing process, thus allowing the use of more fluorescent colors; and/or 2) sequential FISH readout can be off-loaded to manufacturing process with no impact on cells.

Spatial fluorescent encoding of cells/beads can be achieved through sequential fluorescent imaging following each round of fluorescent probe binding. Such spatial barcodes can serve as the key to link phenotype data to sequencing data for single cells at high throughput. For both approaches, the encoding capacity can depend on the number of fluorescent probes used (m) and the number of sequential fluorescent imaging cycles (n). Encoding capacity can be $(m+1)^n$. In some embodiments, the encoding capacity is larger than the number of unique cell indices in the first approach. In some embodiments, the encoding capacity is larger than the number of unique cell labels in the second approach. Current solutions that can link spatial information and gene expression are low throughput and often require special instrumentations. The compositions and methods provided herein are compatible with BD Rhapsody & AbSeq workflows with much higher throughput. The novel and inventive methods of correlating phenotypical information with sequencing for single cells provided herein will open potential applications such as high-throughput drug screening for single cell multi-omics workflows (e.g., BD single-cell multi-omics portfolio).

EXAMPLES

Some aspects of the embodiments discussed above are disclosed in further detail in the following examples, which are not in any way intended to limit the scope of the present disclosure.

Example 1

Oligonucleotides for Associating with Protein Binding Reagents

This example demonstrates designing of oligonucleotides that can be conjugated with protein binding reagents. The oligonucleotides can be used to determine protein expression and gene expression simultaneously. The oligonucleotides can also be used for sample indexing to determine cells of the same or different samples.

95mer Oligonucleotide Design

The following method was used to generate candidate oligonucleotide sequences and corresponding primer sequences for simultaneous determination of protein expression and gene expression or sample indexing.

1. Sequence Generation and Elimination

The following process was used to generate candidate oligonucleotide sequences for simultaneous determination of protein expression and gene expression or sample indexing.

Step 1a. Randomly generate a number of candidate sequences (50000 sequences) with the desired length (45 bps).

Step 1b. Append the transcriptional regulator LSRR sequence to the 5' end of the sequences generated and a poly(A) sequence (25 bps) to the 3' end of the sequences generated.

Step 1c. Remove sequences generated and appended that do not have GC contents in the range of 40% to 50%.

Step 1d. Remove remaining sequences with one or more hairpin structures each.

The number of remaining candidate oligonucleotide sequences was 423.

2. Primer Design

The following method was used to design primers for the remaining 423 candidate oligonucleotide sequences.

2.1 N1 Primer: Use the universal N1 sequence: 5'-GTTGTCAAGATGCTACCGTTCAGAG-3' (LSRR sequence; SEQ ID NO. 3) as the N1 primer.

2.2 N2 Primer (for amplifying specific sample index oligonucleotides; e.g., N2 primer in FIGS. 10B-10D):

2.2a. Remove candidate N2 primers that do not start downstream of the N1 sequence.

2.2b. Remove candidate N2 primers that overlap in the last 35 bps of the candidate oligonucleotide sequence.

2.2c. Remove the primer candidates that are aligned to the transcriptome of the species of cells being studied using the oligonucleotides (e.g., the human transcriptome or the mouse transcriptome).

2.2d. Use the ILR2 sequence as the default control (ACACGACGCTCTTCCGATCT; SEQ ID NO. 4) to minimize or avoid primer-primer interactions.

Of the 423 candidate oligonucleotide sequences, N2 primers for 390 candidates were designed.

3. Filtering

The following process was used to filter the remaining 390 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 10A shows a non-limiting exemplary candidate oligonucleotide sequence generated using the method above.

200mer Oligonucleotide Design

The following method was used to generate candidate oligonucleotide sequences and corresponding primer sequences for simultaneous determination of protein expression and gene expression and sample indexing.

1. Sequence Generation and Elimination

The following was used to generate candidate oligonucleotide sequences for simultaneous determination of protein expression and gene expression and sample indexing.

1a. Randomly generate a number of candidate sequences (100000 sequences) with the desired length (128 bps).

1b. Append the transcriptional regulator LSRR sequence and an additional anchor sequence that is non-human, non-mouse to the 5' end of the sequences generated and a poly(A) sequence (25 bps) to the 3' end of the sequences generated.

1c. Remove sequences generated and appended that do not have GC contents in the range of 40% to 50%.

1d. Sort remaining candidate oligonucleotide sequences based on hairpin structure scores.

1e. Select 1000 remaining candidate oligonucleotide sequences with the lowest hairpin scores.

2. Primer Design

The following method was used to design primers for 400 candidate oligonucleotide sequences with the lowest hairpin scores.

2.1 N1 Primer: Use the universal N1 sequence: 5'-GTTGTCAAGATGCTACCGTTCAGAG-3' (LSRR sequence; SEQ ID NO. 3) as the N1 primer.

2.2 N2 Primer (for amplifying specific sample index oligonucleotides; e.g., N2 primer in FIGS. 10B and 10C):

2.2a. Remove candidate N2 primers that do not start 23 nts downstream of the N1 sequence (The anchor sequence was universal across all candidate oligonucleotide sequences).

2.2b. Remove candidate N2 primers that overlap in the last 100 bps of the target sequence. The resulting primer candidates can be between the 48th nucleotide and 100th nucleotide of the target sequence.

2.2c. Remove the primer candidates that are aligned to the transcriptome of the species of cells being studied using the oligonucleotides (e.g., the human transcriptome or the mouse transcriptome).

2.2d. Use the ILR2 sequence, 5'-ACACGACGCTCTTCCGATCT-3' (SEQ ID NO. 4) as the default control to minimize or avoid primer-primer interactions.

2.2e. Remove N2 primer candidates that overlap in the last 100 bps of the target sequence.

Of the 400 candidate oligonucleotide sequences, N2 primers for 392 candidates were designed.

3. Filtering

The following was used to filter the remaining 392 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 10B shows a non-limiting exemplary candidate oligonucleotide sequence generated using the method above. The nested N2 primer shown in FIG. 10B can bind to the antibody or sample specific sequence for targeted amplification. FIG. 10C shows the same non-limiting exemplary candidate oligonucleotide sequence with a nested universal N2 primer that corresponds to the anchor sequence for targeted amplification. FIG. 10D shows the same non-limiting exemplary candidate oligonucleotide sequence with a N2 primer for one step targeted amplification.

Altogether, these data indicate that oligonucleotide sequences of different lengths can be designed for simultaneous determination of protein expression and gene expression or sample indexing. The oligonucleotide sequences can include a universal primer sequence, an antibody specific oligonucleotide sequence or a sample indexing sequence, and a poly(A) sequence.

Example 2

Oligonucleotide-Associated Antibody Workflow

This example demonstrates a workflow of using an oligonucleotide-conjugated antibody for determining the expression profile of a protein target.

Figure 11:
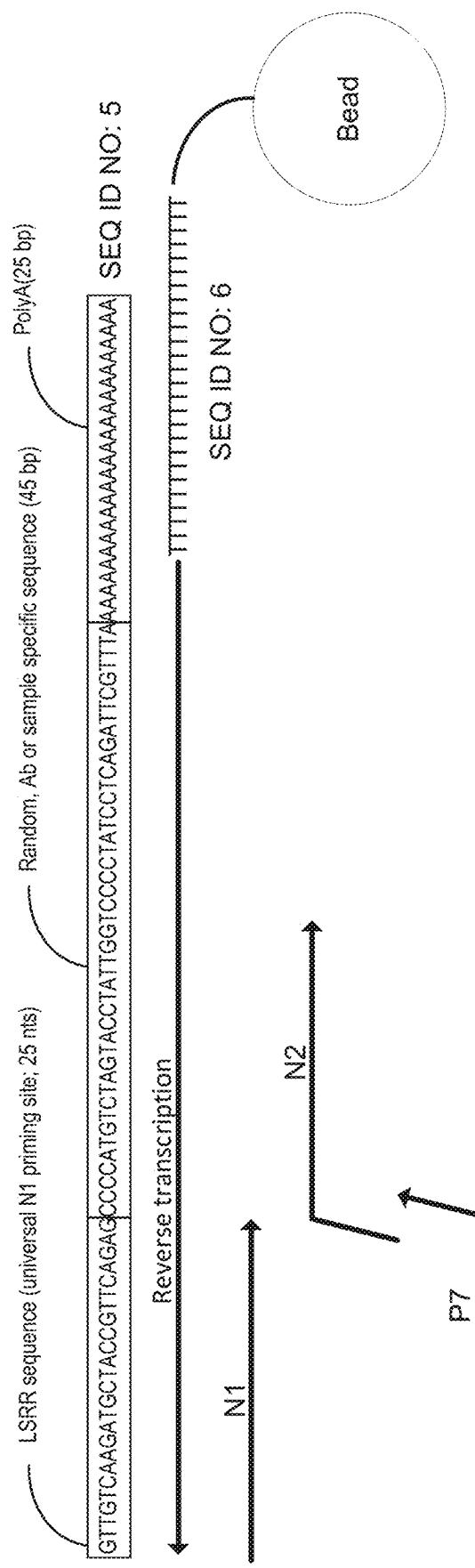
FIG. 11 shows a schematic illustration of a non-limiting exemplary oligonucleotide sequence for determining protein expression and gene expression simultaneously and for sample indexing.

Frozen cells (e.g., frozen peripheral blood mononuclear cells (PBMCs)) of a subject are thawed. The thawed cells are stained with an oligonucleotide-conjugated antibody (e.g., an anti-CD4 antibody at 0.06 µg/100 µl (1:333 dilution of an oligonucleotide-conjugated antibody stock)) at a temperature for a duration (e.g., room temperature for 20 minutes). The oligonucleotide-conjugated antibody is conjugated with 1, 2, or 3 oligonucleotides ("antibody oligonucleotides"). The sequence of the antibody oligonucleotide is shown in FIG. 11. The cells are washed to remove unbound oligonucleotide-conjugated antibody. The cells are optionally stained with Calcein AM (BD (Franklin Lake, New Jersey)) and Draq7™ (Abcam (Cambridge, United Kingdom)) for sorting with flow cytometry to obtain cells of interest (e.g., live cells). The cells are optionally washed to remove excess Calcein AM and Draq7™. Single cells stained with Calcein AM (live cells) and not Draq7™ (cells that are not dead or permeabilized) are sorted, using flow cytometry, into a BD Rhapsody™ cartridge.

Of the wells containing a single cell and a bead, the single cells in the wells (e.g., 3500 live cells) are lysed in a lysis buffer (e.g., a lysis buffer with 5 mM DTT). The mRNA expression profile of a target (e.g., CD4) is determined using BD Rhapsody™ beads. The protein expression profile of a target (e.g., CD4) is determined using BD Rhapsody™ beads and the antibody oligonucleotides. Briefly, the mRNA molecules are released after cell lysis. The Rhapsody™ beads are associated with barcodes (e.g., stochastic barcodes) each containing a molecular label, a cell label, and an oligo(dT) region. The poly(A) regions of the mRNA molecules released from the lysed cells hybridize to the poly(T) regions of the stochastic barcodes. The poly(dA) regions of the antibody oligonucleotides hybridize to the oligo(dT) regions of the barcodes. The mRNA molecules were reverse transcribed using the barcodes. The antibody oligonucleotides are replicated using the barcodes. The reverse transcription and replication optionally occur in one sample aliquot at the same time.

The reverse transcribed products and replicated products are PCR amplified using primers for determining mRNA expression profiles of genes of interest, using N1 primers, and the protein expression profile of a target, using the antibody oligonucleotide N1 primer. For example, the reverse transcribe products and replicated products can be PCR amplified for 15 cycles at 60 degrees annealing temperature using primers for determining the mRNA expression profiles of 488 blood panel genes, using blood panel N1 primers, and the expression profile of CD4 protein, using the antibody oligonucleotide N1 primer ("PCR 1"). Excess barcodes are optionally removed with Ampure cleanup. The products from PCR 1 are optionally divided into two aliquots, one aliquot for determining the mRNA expression profiles of the genes of interest, using the N2 primers for the genes of interest, and one aliquot for determining the protein expression profile of the target of interest, using the antibody oligonucleotide N2 primer ("PCR 2"). Both aliquots are PCR amplified (e.g., for 15 cycles at 60 degrees annealing temperature). The protein expression of the target in the cells are determined based on the antibody oligonucleotides as illustrated in FIG. 11 ("PCR 2"). Sequencing data is obtained and analyzed after sequencing adaptor addition ("PCR 3"), such as sequencing adaptor ligation. Cell types are determined based on the mRNA expression profiles of the genes of interest.

Altogether, this example describes using an oligonucleotide-Conjugated antibody for determining the protein expression profile of a target of interest. This example further describes that the protein expression profile of the target of interest and the mRNA expression profiles of genes of interest can be determine simultaneously.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims

What is claimed is:

1. A method of labeling a plurality of cells with cell indexing oligonucleotides, comprising:
    (a) associating cells in each first partition of a plurality of first partitions with a cellular component-binding reagent of a plurality of cellular component-binding reagents,
    wherein each of the cells comprises one or more cellular component targets, wherein the cellular component-binding reagent is associated with a first indexing oligonucleotide with a first cell indexing subsequence, wherein cellular component-binding reagents in each first partition of the plurality of partitions are associated with first indexing oligonucleotides with the same first cell indexing subsequences, and the first cell indexing subsequences are different between at least two first partitions, and wherein the cellular component-binding reagent is capable of specifically binding to the one or more cellular component targets,
    thereby generating cells associated with the first cell indexing subsequence, in each first partition of the plurality of first partitions, via the cellular component-binding reagent associated with the first indexing oligonucleotide with the first cell indexing subsequence, wherein the cells in at least two first partitions of the plurality of first partitions are associated with first cell indexing subsequences that are different between the at least two first partitions;
    (b) pooling the cells associated with the cellular component-binding reagents in the plurality of first partitions;
    (c) distributing the pooled cells into a plurality of second partitions;
    (d) associating the distributed cells in each second partition of the plurality of second partitions with a second indexing oligonucleotide of a plurality of second indexing oligonucleotides with a second cell indexing subsequence, wherein the second indexing oligonucleotides of the plurality of second indexing oligonucleotides in at least two second partitions of the plurality of second partitions comprise second cell indexing subsequences that are different between the at least two second partitions,
    thereby generating cells associated with the second cell indexing subsequence, in each second partition of the plurality of second partitions, wherein the cells in two second partitions of the plurality of second partitions are associated with different second cell indexing subsequences;
    (e) generating cells associated with the cellular component-binding reagent in each second partition of the plurality of second partitions associated with a cell indexing oligonucleotide,
    wherein a cell indexing sequence of the cell indexing oligonucleotide comprises:
        the first cell indexing subsequence; and
        the second cell indexing subsequence of the second cell indexing oligonucleotide associated with the second partition of the plurality of second partitions, via the cellular component-binding reagent associated with the first indexing oligonucleotide with the first cell indexing subsequence associated with each of the cells in the second partition;
    (f) pooling the cells associated with the cellular component-binding reagents in the plurality of second partitions;
    (g) performing steps (c), (d), (e), and (f) n times, wherein n is a positive integer greater than 1,
    thereby generating a plurality of cells associated with unique cell indexing oligonucleotides, each unique cell indexing oligonucleotide comprising:
        n cell indexing subsequences; and
        a target sequence comprising a sequence complementary to a capture sequence of a stochastic label configured to hybridize to the target sequence, wherein the stochastic label comprises a target binding region comprising the capture sequence, wherein the target binding region is configured to hybridize to a nucleic acid target of a cell of the plurality of cells,
    wherein different cells of the plurality of cells are associated with cell indexing oligonucleotides comprising different n cell indexing subsequences;
    (h) partitioning the plurality of cells associated with the unique cell indexing oligonucleotides to a plurality of third partitions on a substrate, wherein each third partition of the plurality of third partitions is a distinct spatial location on the substrate and comprises at most a single cell from the plurality of cells associated with the unique cell indexing oligonucleotides;
    (i) determining a spatial index of the unique cell indexing oligonucleotides in the plurality of third partitions using n pluralities of probes by sequentially hybridizing and imaging the n pluralities of probes annealing to the n cell indexing subsequences, wherein the spatial index identifies a distinct spatial location of each of the plurality of third partitions on the substrate.

2. The method of claim 1, wherein the nth indexing oligonucleotide comprises an (n−1)th linker sequence and the target sequence.

3. The method of claim 2, wherein the target sequence comprises a poly(A) sequence.

4. The method of claim 1, wherein the n pluralities of probes comprise one or more detectable moieties, wherein the imaging comprises detecting the one or more detectable moieties.

5. A method of generating a spatial index, comprising the steps of:
    partitioning a plurality of synthetic particles comprising stochastic labels that comprise unique cell indexing oligonucleotides to a plurality of partitions in a substrate, wherein each partition of the plurality of partitions is a distinct spatial location on the substrate and comprises a unique cell indexing oligonucleotide,
    wherein the unique cell indexing oligonucleotide comprises a cell indexing sequence comprising a series of n cell indexing subsequences that represent n distinct positions along the cell indexing sequence, wherein n is an integer greater than 1,
    wherein each of the plurality of stochastic labels comprises:
        a cellular label comprising the cell indexing sequence;
        a molecular label, wherein molecular label sequences of at least two stochastic labels of the plurality of stochastic labels comprise different molecule label sequences; and
a target nucleic acid binding region; and
in each partition of the plurality of partitions:
(a) contacting the unique cell indexing oligonucleotide with a plurality of probes,
wherein one or more of the probes of the plurality of probes comprise a detectable moiety, or precursor thereof, wherein at least one of the plurality of probes selectively anneal to cell indexing subsequences with complementary sequences, wherein the at least one probe that selectively anneals to a cell indexing subsequence anneals to at most one of the n distinct positions along the cell indexing sequence;
(b) removing unannealed probes;
(c) imaging the unique cell indexing oligonucleotide, wherein imaging comprises detecting a signal of the detectable moiety at the distinct spatial location on the substrate;
(d) removing the annealed probes and/or the detectable moieties thereof; and
(e) repeating the steps (a)-(d) for a total of n cycles, wherein in each cycle, each probe that selectively anneals to a cell indexing subsequence anneals to a different position of the n distinct positions along the cell indexing sequence than the position of the cell indexing subsequence along the cell indexing sequence to which the at least one probe selectively annealed in any preceding cycle, whereby a spatial index is generated for the unique cell indexing oligonucleotide,
wherein the spatial index comprises a series of: one or more signals; and/or one or more absences of a signal, detected in the n cycles, wherein the sum of the number of the one or more signals and the number of the one or more absences of a signal is n, wherein the spatial index identifies the distinct spatial location on the substrate of each of the plurality of partitions.

6. The method of claim 5, wherein in each cycle of the n cycles, the plurality of probes comprises p unique probes, wherein unique probes selectively anneal to different cell indexing subsequences, and wherein p is an integer greater than 1.

7. The method of claim 6, wherein
m probes of the p unique probes comprise a detectable moiety, or precursor thereof, wherein m is an integer greater than 1, and wherein m is p−1.

8. The method of claim 5, wherein the cell indexing oligonucleotide is associated with a synthetic particle.

9. The method of claim 8, wherein the synthetic particle comprises a plurality of stochastic labels, wherein the stochastic labels are oligonucleotides, and wherein a stochastic label comprises the cell indexing sequence.

10. The method of claim 5, wherein the method comprises generating a spatial index of a plurality of unique cell indexing oligonucleotides.

11. The method of claim 10, wherein the method comprises generating a spatial index of at least 96 unique cell indexing oligonucleotides.

12. The method of claim 5, wherein each of two or more partitions of the plurality of partitions comprises at most a single cell and/or at most a single bead.

13. The method of claim 12, wherein
(i) the single cell is associated with the unique cell indexing oligonucleotide, wherein the unique cell indexing oligonucleotide associated with cells in different partitions comprise different cell indexing sequences, and/or
(ii) the single bead is associated with the unique cell indexing oligonucleotide, wherein the unique cell indexing oligonucleotide associated with beads in different partitions comprise different cell indexing sequences.

14. The method of claim 1, wherein the nth indexing oligonucleotide comprises the target sequence.

15. The method of claim 14, wherein the sequence complementary to the capture sequence of the stochastic label comprises a poly(A) sequence.

16. The method of claim 14, further comprising:
stochastically labeling the cell indexing oligonucleotides and nucleic acid target molecules in the third partition using a plurality of stochastic labels to generate a plurality of stochastically labeled cell indexing oligonucleotides and a plurality of stochastically labeled nucleic acid target molecules,
wherein the stochastic labels comprise a cellular label, wherein the stochastic labels associated with the same cell comprise the same cellular label, and wherein the stochastic labels associated with different cells comprise different cellular labels;
obtaining the sequencing data of the plurality of stochastically labeled cell indexing oligonucleotides and the plurality of stochastically labeled nucleic acid target molecules,
wherein obtaining the sequencing data of stochastically labeled cell indexing oligonucleotides comprises sequencing at least a portion of the cellular label and at least a portion of a cell indexing sequence; and
determining the spatial location of each nucleic acid target molecule by associating the cellular label of the third partition and the cell indexing sequence of the third partition, wherein the spatial location comprises the identity of the third partition from which the nucleic acid target molecule originated.

17. The method of claim 1, further comprising obtaining phenotypic data for one or more single cells in the plurality of third partitions by making one or more phenotypic measurements of the one or more single cells that are each isolated in a third partition of the plurality of third partitions, wherein the phenotypic data is associated with a location of the third partition within a substrate comprising the plurality of third partitions.

18. The method of claim 5, wherein the spatial index comprises a series of: one or more signals; and one or more absences of a signal, detected in the n cycles.

19. The method of claim 17, wherein obtaining phenotypic data comprises imaging the one or more single cells in the plurality of third partitions.

20. The method of claim 17, wherein the phenotypic data comprises:
(A) measurement of one or more of the localization, expression intensity, and persistence of expression of the one or more cellular component targets, wherein the one or more cellular component targets comprise one or more endogenous proteins;
(B) measurement of cell death, and wherein the cell death is evaluated by detecting apoptosis markers;
(C) measurement of a dynamic behavior of the one or more single cells as a function of time; and/or
(D) measurement of cellular activation, cellular inhibition, cellular interaction, protein expression, protein secretion, metabolite secretion, changes in lipid profiles, microvesicle secretion, exosome secretion, microparticle secretion, changes in cellular mass, cellular proliferation, changes in cellular morphology, motility, cell death, cell cytotoxicity, cell lysis, cell membrane polarization, establishment of a synapse, dynamic trafficking of proteins, granule polarization, calcium activation, metabolic changes, small molecule secretion, proton secretion, or any combination thereof.

21. The method of claim 1, wherein the sequence complementary to the capture sequence of the stochastic label comprises a poly(A) sequence.

22. A method of generating a spatial index of a plurality of cells associated with cell indexing oligonucleotides, comprising:
  generating a plurality of cells associated with unique cell indexing oligonucleotides by n rounds of split-pool synthesis, wherein n is an integer greater than 1, wherein each cell is associated with a unique cell indexing oligonucleotide via a cellular component-binding reagent, wherein each cell indexing oligonucleotide comprises:
    a cell indexing sequence comprising n cell indexing subsequences; and
    a target sequence comprising a sequence complementary to a capture sequence of a stochastic label configured to hybridize to the target sequence, wherein the stochastic label comprises a target binding region comprising the capture sequence, wherein the target binding region is configured to hybridize to a nucleic acid target of a cell of the plurality of cells, wherein n is greater than 1, and wherein each round of split-pool synthesis provides a cell indexing subsequence of the n cell indexing subsequences,
    wherein the cell indexing sequence of a cell indexing oligonucleotide associated with a cell of the plurality of cells is different from the cell indexing sequence of cell indexing oligonucleotides associated with different cells of the plurality of cells;
  partitioning the plurality of cells associated with the unique cell indexing oligonucleotides to a plurality of partitions on a substrate, wherein each partition of the plurality of partitions is a distinct spatial location on the substrate and comprises at most a single cell from the plurality of cells associated with the unique cell indexing oligonucleotides; and
  generating a spatial index of the unique cell indexing oligonucleotides in the plurality of partitions using n pluralities of probes by sequentially hybridizing and imaging the n pluralities of probes annealing to the n cell indexing subsequences, wherein the spatial index identifies a distinct spatial location of the plurality of partitions on the substrate.

23. The method of claim 22, wherein in each round of the n rounds of split-pool synthesis:
  (i) the plurality of cells are distributed into a plurality of second partitions;
  (ii) in each second partition of the plurality of second partitions, the distributed plurality of cells are associated with an indexing oligonucleotide comprising the cell indexing subsequence via the cellular component-binding reagent, wherein the indexing oligonucleotides in different second partitions comprise different cell indexing subsequences; and
  (iii) the distributed plurality of cells that are associated with the indexing oligonucleotide are pooled.

24. The method of claim 23, wherein the nth indexing oligonucleotide comprises the target sequence.

25. The method of claim 22, wherein the target sequence comprises a poly(A) sequence.

26. The method of claim 22, further comprising:
  stochastically labeling the unique cell indexing oligonucleotides associated with the partitioned plurality of cells using a plurality of the stochastic labels to generate a plurality of stochastically labeled cell indexing oligonucleotides, wherein each of the stochastic labels comprises a cellular label, wherein the stochastic labels associated with the same cell comprise the same cellular label, and wherein the stochastic labels associated with different cells comprise different cellular labels;
  obtaining sequencing data of at least a portion of the cellular label and at least a portion of the cell indexing sequence associated with the same stochastically labeled unique cell indexing oligonucleotide; and
  determining the distinct spatial location on the substrate to which a cell associated with the same stochastically labeled unique cell indexing oligonucleotide was partitioned, based on the at least a portion of the cellular label, the at least a portion of the cell indexing sequence, and the spatial index.

27. The method of claim 5, wherein the unique cell indexing oligonucleotide comprises a target sequence comprising a sequence complementary to a capture sequence of a stochastic label configured to hybridize to the target sequence.

28. The method of claim 16, further comprising obtaining phenotypic data for one or more single cells in the plurality of third partitions by making one or more phenotypic measurements of the one or more single cells that are each isolated in a third partition of the plurality of third partitions, wherein the phenotypic data is associated with a location of the third partition within a substrate comprising the plurality of third partitions.

29. The method of claim 28, further comprising:
  conducting agent exposure, wherein agent exposure comprises exposing a plurality of the one or more single cells to one or more agents, wherein at least two of the plurality of the one or more single cells are exposed to different agents and/or different concentrations of the same agent, wherein the obtained phenotypic data comprises one or more phenotypic effects of the agent exposure, wherein obtaining phenotypic data comprises imaging the one or more single cells in the plurality of third partitions; and
  associating the sequencing data with the spatial index and the obtained phenotypic data.

30. The method of claim 27, wherein the sequence complementary to the capture sequence of the stochastic label comprises a poly(A) sequence.

* * * * *